US008263354B2

(12) United States Patent
O'Connor et al.

(10) Patent No.: US 8,263,354 B2
(45) Date of Patent: *Sep. 11, 2012

(54) METHODS FOR ASSESSING CANCER FOR INCREASED SENSITIVITY TO 10-PROPARGYL-10-DEAZAAMINOPTERIN

(75) Inventors: Owen A. O'Connor, Scarsdale, NY (US); Francis M. Sirotnak, Hampton Bays, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 97 days.

This patent is subject to a terminal disclaimer.

(21) Appl. No.: 12/815,321

(22) Filed: Jun. 14, 2010

(65) Prior Publication Data

US 2011/0111436 A1 May 12, 2011

Related U.S. Application Data

(63) Continuation-in-part of application No. 12/637,254, filed on Dec. 14, 2009, now Pat. No. 8,168,404, which is a continuation of application No. 11/953,031, filed on Dec. 8, 2007, now abandoned, which is a continuation-in-part of application No. 11/568,254, filed as application No. PCT/US2005/019170 on May 31, 2005, now Pat. No. 7,939,530.

(60) Provisional application No. 60/521,593, filed on May 30, 2004.

(51) Int. Cl.
*G01N 33/574* (2006.01)
(52) U.S. Cl. ..................................... 435/7.23
(58) Field of Classification Search .......... None
See application file for complete search history.

(56) References Cited

U.S. PATENT DOCUMENTS

| | | | |
|---|---|---|---|
| 4,393,064 | A | 7/1983 | Degraw et al. |
| 4,433,147 | A | 2/1984 | Degraw et al. |
| 4,652,533 | A | 3/1987 | Jolley |
| 4,843,155 | A | 6/1989 | Chomczynski |
| 5,354,751 | A | 10/1994 | DeGraw et al. |
| 5,981,592 | A | 11/1999 | Wechter et al. |
| 6,028,071 | A | 2/2000 | Sirotnak et al. |
| 6,323,205 | B1 | 11/2001 | Sirotnak et al. |
| 6,410,696 | B1 | 6/2002 | Davalian et al. |
| 2005/0267117 | A1 | 12/2005 | O'Connor et al. |

FOREIGN PATENT DOCUMENTS

| | | |
|---|---|---|
| WO | 98/02163 | 1/1998 |
| WO | 2005/117891 A1 | 12/2005 |
| WO | 2005/117892 A1 | 12/2005 |

OTHER PUBLICATIONS

Weidmann, E et al. "Diagnosis and actual therapy strategies in peripheral T-Cell lymphomas: summary of an international meeting." Annals of Oncology 2004, pp. 369-374, vol. 15.
Weinstein, Gerald D. "Diagnosis and Treatment: Drugs Five Years Later: Methotrexate" Annals of Internal Medicine, 1977, pp. 199-204, vol. 86.
Willemze, Rein et al., "WHO-EORTC classification for cutaneous lymphomas", Blood (www.bloodjournal.org), May 15, 2005, pp. 3768-3785, vol. 105, No. 10, The American Society of Hematology.
Wright, Joel et al., "Further studies on the interaction of nonpolyglutamatable aminopterin analogs with dihydrofolate reductase and the reduced folate carrier as determinants of in vitro antitumor activity", Biochemical Pharmacology, 2003, pp. 1427-1433, vol. 65, Elsevier.
Akutsu, M et al. "Schedule-dependent synergism and antagonism between methotrexate and cytarabine against human leukemia cell lines in vitro." Leukemia. Mar. 12, 2002. pp. 1808-1817. vol. 16.
Allos Therapeutics, Inc. "Allos Therapeutics Reports Interim Response and Safety Data from Pivotal Phase 2 Propel Trial." May 15, 2008 (Press Release).
Allos Therapeutics, Inc. "Results Reported at the American Society of Hematology Annual Meeting Affirm Impressive Activity of Allos Therapeutics' Novel Antifolate PDX in Patients with Peripheral T-Cell Lymphoma." Dec. 11, 2006 (Press Release).
Assaraf, Yehuda. "Molecular Basis of Anitfolate Resistance." Cancer Metastasis Rev., 2007. pp. 153-181, vol. 26, Springer.
Ausubel, Frederick et al. "Current Protocols in Molecular Biology." 1987. Current Protocols. vol. 2, pp. 16.8-16.8.5, 16.9.1-16.9.6, 16.10. 1-16.10.8, 16.11.1-16.11.7.
Au et al., Aggressive subcutaneous panniculitis-like T-cell lymphoma: complete remission with fludarabine, mitoxantrone and dexamethasone, British Journal of Dermatology, 2000, vol. 143, pp. 408-410.
Awar, Omar et al. "Treatment of Transformed Mycosis Fungoides with Intermittent Low-Dose Gemcitabine." Oncology Sep. 23, 2007, pp. 103-135, vol. 73, Department of Internal Medicine.
Azzoli, Christopher et al. "A Phase 1 Study of Pralatrexate in Combination with Paclitaxel or Docetaxel in Patients with Advance Solid Tumors." Clin. Cancer Res. May 1, 2007 pp. 2692-2698, vol. 13, No. 9.
Barberio, E et al. "Transformed mycosis fungoides: clinicopathological features and outcome." British Journal of Dermatology, 2007, pp. 284-289, vol. 157, British Association of Dermatologists.
Barredo, Julio et al. "Differences in Constitutive and Post-Methotrexate Folylpolyglutamate Synthetase Activity in B-Lineage and T-Lineage Leukemia." Blood, Jul. 15, 1994, pp. 564-569, vol. 84, No. 2.
Bekkenk, Marcel et al. "Peripheral T-Cell Lymphomas Unspecified Presenting in the Skin: Analysis of Prognostic Factors in a Group 82 Patients." Blood Sep. 13, 2003, pp. 2213-2219, vol. 102, No. 6, The American Society of Hematology.

(Continued)

*Primary Examiner* — Sheela J Huff
(74) *Attorney, Agent, or Firm* — Larson & Anderson, LLC

(57) ABSTRACT

Sensitivity of a patient's cancer to treatment with 10-propargyl-10-deazaaminopterin is assessed and patients are selected for treatment of cancer with 10-propargyl-10-deazaaminopterin, by determining the amount of a selected polypeptide expressed by the cancer and comparing the amount with the amount of the selected polypeptide expressed by a reference cancer. The polypeptide includes a member of a folate pathway polypeptide within a cell and may include at least one of reduced folate carrier-1 enzyme (RFC-1), dihydrofolate reductase (DHFR), folylpoly-gamma-glutamate synthetase (FPGS), thymidylate synthase (TS), γ-glutamyl hydrolase (GGH), and glycinamide ribonucleotide formyltransferase (GARFT).

7 Claims, 5 Drawing Sheets

OTHER PUBLICATIONS

Burg, Gunter et al. "WHO/EORTC classification of cutaneous lymphomas 2005: histological and molecular aspects." Journal of Cutaneous Pathology, 2005, pp. 647-674, vol. 32, Blackwell Munksgaard.

Burg, Gunter et al. "Cutaneous Lymphomas Current and Future Concepts." J Egypt wom. Dermatol. Soc., 2007, pp. 1-23, vol. 4, No. 1.

Cadman, Ed et al. "Mechanism of Synergistic Cell Killing when Methotrexate Precedes Cytosine Arabinoside." J. Clin. Invest. 1979. pp. 788-797. vol. 64.

Chau, I et al. "Gemcitibine and its combinations in the treatment of malignant lymphoma." Clinical Lymphoma. 2002. pp. 97-104. vol. 3, No. 11.

Cheson, Bruce et al. "Report of an International Workshop to Standardize Response Criteria for Non-Hodgkin's Lymphoma's." 1999, pp. 1244-1253, vol. 117, No. 4, Journal of Clinical Oncology.

Connors, Joseph et al. "Lymphoma of the Skin." Hematology, 2002, pp. 263-282, American Society of Hematology.

Degraw, et al. "Synthesis and Antitumor Activity of 10-Propargyl-10-deazaaminopterin." Journal of Medical Chemistry. 1993. pp. 2228-2231. vol. 36.

Degraw, J. et al. "Synthesis and Antitumor Activity of 10-Alkyl-10-deazaaminopterins. A Convenient Synthesis of 10-Deazaaminopterin." J. Med. Chem. 1982, pp. 1227-1230, vol. 25, American Chemical Society.

Degraw, Joseph et al. "New Analogs of Methotrexate in Cancer and Arthritis." Current Medicinal Chemistry, 1995, pp. 630-653, vol. 2, Bentham Science Publishers B.V.

Diamandidou, Eleni et al. "Transformation of Mycosis Fungoides/Sezary Syndrome: Clinical Characteristics and Prognosis." Blood, 1998, pp. 1150-1159, vol. 92, American Society of Hematology (From www.bloodjournal.org by on Jul. 21, 2008).

Diddens, Heyke et al. "Patterns of Cross-Resistance to the Antigolate Drugs Trimetrexate, Metoprine, Homofolate, and CB3717 in Human Lymphoma and Osteosarcoma Cells Resistant to Methotrexate." Cancer Research, Nov. 1983, pp. 5286-5292, vol. 43.

Dmitrovsky, Ethan et al. "Cytologic Transformation in Cutaneous T Cell Lymphoma: A Clinicopathologic Entity Associated With Poor Prognosis." Journal of Clinical Oncology, Feb. 1987, pp. 208-215, vol. 5, No. 2, The American Society of Clinical Oncology.

Fotoohi, Kambiz et al. "Disparate mechanisms of Antifolate resistance provoked by methotrexate and its ,metabolite 7-hydroxymethotrexate in leukemia cells: Implications for efficacy of methotrexate therapy." Blood, Aug. 12, 2004, pp. 1-32, American Society of Hematology.

Fouchard et al., Cutaneous T cell lymphomas: mycosis fungoides, Sezary syndrome and HTLV associated adult T cell leukemia (ATL) in Mali, West Africa: a clinical, pathological and immunovirological study of 14 cases and a review of the African ATL cases, Leukemia, 1998, vol. 12, pp. 578-585 (Abstract attached.).

Fry, David et al. "Biological and biochemical properties of new anticancer folate antagonists." Cancer and Metastasis Reviews, 1987, pp. 251-270, vol. 5, Martinus Nijoff Publishers, Boston.

Fury, Matthew et al. "A phase I clinical pharmacologic study of pralatrexate in combination with probenecid in adults with advanced solid tumors." Cancer Chemother Pharmacol. 2006, pp. 671-677, vol. 57, Springer-Verlag.

Galpin, Amy et al. "Differences in Folylpolyglutamate Synthetase and Dihydrofolate Reductase Expression in Human B-Lineage versus T-Lineage Leukemic Lymphoblasts: Mechanisms for Lineage Differences in Methotrexate Polyglutamylation and Cytotoxicity." Molecular Pharmacology, 1997, pp. 155-163, vol. 52, The American Society for Pharmacology and Experimental Therapuetics.

Gangjee, Aleem et al. "Effect of Bridge Region Variation on Antifolate and Antitumor Activity of Classical 5-Substituted 2,4-Diaminofuro [2,3-d] pyrimidines." J. Med. Chem. 1995, pp. 3798-3805, vol. 38, American Chemical Society.

Girardi, Michael et al. "The Pathogenesis of Mycosis Fungoides." The New England Journal of Medicine, May 6, 2004, pp. 1978-1988, vol. 350, No. 19, Massachusetts Medical Society.

Gisselbrecht, Christian et al. "Prognostic Significance of T-Cell Phenotype in Aggressive Non-Hodgkin's Lymphomas." Blood, Jul. 1, 1998, pp. 76-82, vol. 92, No. 1, The American Society of Hematology.

Grenzebach, J et al. "Favorable outcome for children and adolescents with T-cell lymphoblastic lymphoma with an intensive ALL-type therapy without local radiotherapy." Ann Hematol., 2001, pp. B73-B76, vol. 80, Springer-Verlag.

Hallermann, Christian et al. "Regulatory T-Cell phenotype in association with large cell transformation of mycosis fungoides." European Journal of Haematology, 2007, pp. 260-263, vol. 78, Blackwell Munksgaard.

Haynes, Harley et al. "Therapy of Mycosis Fungoides." Progress in Germatology, Mar. 1968, pp. 1-5, vol. 3, Dermatology Foundation.

Holm, Jan et al."High and Low Affinity Binding of Folate to Proteins in Serum of Pregnant Women." Biochimica et Biophysica Acta, 1980, pp. 539-545, vol. 629, Elsevier/ North-Holland Biomedical Press.

Howard, Michael et al. "Mycosis Fungoides: Classic Disease and Variant Presentations." 2000, pp. 91-99, vol. 19, No. 2, Departments of Pathology and Dermatology.

Hoovis, ML et al. "Enhancement of the Antiproliferative Action of 1-β-D-Arabinofuranosylcytosine by Methotrexate in Murine Leukemic Cells (L5178Y)." Cancer Research. 1973. pp. 521-525. vol. 33.

Huennekens, F et al. "The Methotrexate Story: A Paradigm for Development of Cancer Chemotherapeutic Agents." Advan. Enzyme Regul. 1994, pp. 397-419, vol. 34, Elsevier Science Ltd.

Janeway-Travers. "Immunobiology: the immune system in health and disease" 1996, 2nd edition, Garland Pub pp. 1:1-1-1:32.

Kamarashev, Jivko et al. "Mycosis fungoides—analysis of the duration of disease stages in patients who progress and the time point of high-grade transformations" International Journal of Dermatology, 2007, pp. 930-935, vol. 46, The International Society of Dermatology.

Khokhar, Nushima et al. "Experimental Therapeutices with a New 10-Deazaaminopterin in Human Mesothelioma: Further Improving Efficacy through Structural Design, Pharmacologic Modulation at the Level of MRP ATPases, and Combined Therapy with Platinums." Clinical Cancer Research. 2001. pp. 3199-3205. vol. 7.

Krug, Lee et al. "10-propargy1-10-deazaaminopterin: an antifolate with activity in patients with previously treated non-small cell lung cancer." Clinical Cancer Research: An official journal of the American Association for Cancer Research. 2003. pp. 2072-2078. vol. 9, No. 6.

Krug, Lee et al. "Phase II Trial of Pralatrexate (10-Propargyl-10-deazaaminopterin, PDX) in Patients with Unrealistically Malignant Pleural Mesothelioma." Journal of Thoracic Oncology, Apr. 2007, pp. 317-320, vol. 2, No. 4.

Krug, Lee et al. "Phase I and Pharmacokinetic Study of 10-Propargyl-10-deazaaminopterin, a New Antifolate." Clinical Cancer Research, Sep. 2000, pp. 3493-3498, vol. 6.

Liang et al., Intensive chemotherapy for peripheral T-cell lymphomas., Hematological Oncology, 1992, vol. 10, pp. 155-161, (Abstract attached.).

Leclerc, Guy et al. "Analysis of folylpoly-y-glutamate synthetase gene expression in human B-precursor ALL and T-lineage ALL cells." BMC Cancer, May 2006, pp. 1-12, vol. 6, No. 132, BioMed Central.

Longo-Sorbello, Giuseppe et al. "Current understanding of methotrexate pharmacology and efficacy in acute leukemias. Use of newer antifolate in clinical trials." Hematologica, 2001, pp. 121-127, vol. 86, Trends in Hematology.

Lundin, Jeanette et al. "Therapy for Mycosis Fungoides." Current Treatment Option in Oncology, 2004, pp. 203-214, vol. 5, Current Science Inc.

Matsuo et al. "Association between polymorphisms of folate-and methionine-metabolizing enzymes and susceptibility to malignant lymphoma" Blood, 2001, pp. 3205-3209, vol. 97, No. 10.

Mercadal, S. et al. "Intensive chemotherapy (high-dose CHOP/ESHAP regimen) followed by autologous stem0cell transplantation in previously untreated patients with peripheral T-cell lymphoma." Annals of Oncology 2008, pp. 958-963, vol. 19, Oxford University.

McDonald, Charles et al. "Cutaneous uses of the antiproliferative drugs." American Society for Clinical Pharmacology and Therapeutics, American Society for Pharmacology and Experimental Therapeutics, Nov. 1974, pp. 1-8, vol. 16, No. 5, The C.V. Mosby Company.

Moccio, D.M et al. "Similar Specificity of Membrane Transport for Folate Analogues and Their Metabolites by Murine and Human Tumor Cells: A Clinically Directed Laboratory Study." Cancer Research, Jan. 1984, pp. 352-357, vol. 44.

Molina, Julian et al. "Pralatrexate, a dihydrofolate reductase inhibitor for the potential treatment of several malignancies." IDrugs, 2008, pp. 508-521, vol. 11, No. 7, Drug Profile.

Methotrexate Injection, USP. Mayne, 2005, pp. 1-26.

Nair, M. et al. "Synthesis and Biological Evaluation of Poly-y-glutamyl Metabolites of 10-Deazaaminopterin and 10-Ethyl-10-deazaaminopterin." J. Med Chem. 1988, pp. 181-185, American Chemical Society.

www.nccn.org "Non-Hodgkins's Lymphomas" V.3.2008, Apr. 10, 2008, National Comprehensive Cancer Network.

O'Connor, Owen. "Developing new drugs for the Treatment of lymphoma." European Journal of Haematology, 2005, pp. 150-158, vol. 75 (Supp 66), Blackwell Munksgaard.

O'Connor, Owen et al. "A Phase '2-1-2' Study of Two Different Doses and Schedules of Pralatrexate, A High Affinity Substrate for the Reduced Folate Carrier (rfc-1), in Patients with Relapsed or Refactory Lymphoma Reveals Marked Activity in T-Cell Malignancies." AACR, 2007.

O'Connor, Owen et al. "Pralatrexate (PDX) Produces Durable Complete Remissions in Patients with Chemotherapy Resistant Precursor and Peripheral T-Cell Lymphomas: Results of the MSKCC Phase I/II Experience." Blood, 2006, pp. 1-2, vol. 108, American Society of Hematology, Abstract 400.

O'Connor, Owen et al. "Pralatrexate (10-propargyl-10-deazaaminopterin (PRX)), a Novel Antifolate, Effects Durable Complete Remissions (CR) in Patients with a Diversity of Drug Resistant T-Cell Lymphomas with Minimal Toxicity." Blood, 2005, pp. 1-2, vol. 106, American Society of Hematology, Abstract 2678.

O'Connor, Owen et al. "Pralatrexate, a novel class of antifol with high affinity for the reduced folate carrier type 1, produces marked complete and durable remissions in a diversity of chemotherapy refactory cases of T-cell lymphoma." Journal Compilation, 2007, pp. 425-428, vol. 139, Black well Publishing Ltd.

O'Connor, Owen. "Pralatrexate: an emerging new agent with activity in T-cell lymphomas." Current Opinion in Oncology, 2006, pp. 591-597, vol. 18, Lippincott Williams & Wilkins.

O'Connor, Owen et al. "Pralatrexate (PDX) Produces Durable Complete Remissions in Patients with Chemotherapy Resistant Precursor and Peripheral T-Cell Lymphomas: Results of the MSKCC Phase I/II Experience." Dec. 2006, Power Point Presentation, ASH.

Olsen, Elise et al. "Revisions to the staging and classification of mycosis fungoides and Sezary syndrome: a proposal of the International Society for Cutaneous Lymphomas (ISCL) and the cutaneous lymphoma task force of the European Orginization of Research and Treatment of Cancer (EORTC)." Blood, Sep. 15, 2007, pp. 1713-1722, vol. 110, No. 6, The American Society if Hematology.

Paulli, Marco et al. "Cutaneous T-cell Lymphoma (including rare subtypes). Current concepts. II." Haematologica, Nov. 2004, pp. 1372-1388, vol. 89, Malignant Lymphomas.

Prochazkova, Martina et al. "Large Cell Transformation of mycosis fungoides: tetraploidization within skin tumor large cells." Cancer Genetics and Cytogenetics 2005, pp. 1-6, vol. 163.

Quereux, Gaelle et al. "Prospective Multicancer Study of Pegylated Liposomal Doxorubicin Treatment in Patients With Advanced or Refractory Mycosis Fungoides or Sezary Syndrome." Arch Dermatology 2008, pp. 727-733, vol. 144, No. 6.

Rezania, Dorna et al. "The Diagnosis, Management, and Role of Hematopoietic Stem Cell Transplantation in Aggressive Peripheral T-Cell Neoplasms." Cancer Control, Apr. 2007, pp. 151-159, vol. 14, No. 2.

Rizvi, Mujahid et al. "T-cell non-hodgkin lymphoma." Blood, Feb. 15, 2006, pp. 1255-1264, vol. 107, No. 4, The American Society of Hematology.

Rodriguez-Abreu, Delvys et al. "Peripheral T-cell Lymphomas, unspecified (or not otherwise specified): a review." Hematol Oncol. 2008 pp. 8-20, vol. 26.

Rosen, Steven et al. "Primary Cutaneous T-Cell Lymphomas." 2006, pp. 323-330, American Society of Hematology.

Rots, Marianne et al. "Role of Folylpolyglutamate Synthetase and Folylpolyglutamate Hydrolase in Methotrexate Accumulation and Polyglutamylation in Childhood Leukemia." Blood, 1999, pp. 1677-1683, vol. 93, The American Society of Hematology.

Rots, M. et al. "mRna expression levels of methotrexate resistance-related proteins in childhood leukima as determined by a standardized competitive template-based RT-PCR method." Leukemia, 2000, pp. 2166-2175, vol. 14, MacMillan Publishers Ltd.

Rumberger, B et al. "Differing Specificities for 4-Aminofolate Analogues of Folypolyglutamyl Synthetase from Tumors and Proliferative Intestinal Epithelium of the Mouse with Significance for Selective Antitumor Action." Cancer Research, Aug. 1, 1990, pp. 4639-4643, vol. 50.

Salhany, Kevin et al. "Transformation of Cutaneous T Cell Lymphoma to Large Cell Lymphoma." American Journal of Pathology, Aug. 2, 1988, pp. 265-277, vol. 132, No. 2, American Association of Pathologists.

Sambrook, Joesph et al. "Molecular Cloning." A Labratory Manual. 1989. Cold Spring Harbor. Second Edition.

Samuels, Lawrence et al. "Similar Differential for Total Polyglutamylation and Cytotoxicity among Various Folate Analogues in Human and Murine Tumor Cells in Vitro." Cancer Research, Apr. 1985, pp. 1488-1495, vol. 45, Presented in part at the 74th Annual Meeting of the American Association for Cancer Research.

Samuels, L et al. "Hydrolytic Cleavage of Methotrexate γ-Polyglutamates by Folylpolyglutamyl Hydrolase Derived from Various Tumors and Normal Tissues of the Mouse." Cancer Research, May 1986, pp. 2230-2235, vol. 46.

Sarris, A et al. "Trimetrexate in Relapsed T-Cell Lymphoma With Skin Involvement." Journal of Clinical Oncology, Jun. 15, 2002, pp. 2876-2880, vol. 20, No. 12, The American Society of Clinical Oncology.

Savage, K. et al. "Characterization of peripheral T-cell lymphomas in a single North American institution by the WHO classification." Annals of Oncology 2004 pp. 1467-1475, vol. 15.

Savage, Kerry "Aggressive Peripheral T-Cell Lymphomas (Specified and Unspecified Types)". Hematology, 2005, pp. 267-277, American Society of Hematology.

Scott, Eugene et al. "Therapy of Mycosis Fungoides Lymphoma." Skin Cancer Panel,1968, pp. 553-557, J.B. Lippincott Company.

Siegel, Richard et al., "Primary Cutaneous T-Cell Lymphoma: Review and Current Concepts", Journal of Clinical Oncology, Aug. 15, 2000, pp. 2908-2925, vol. 18, No. 15, American Society of Clincial Oncology.

Sirotnak, F.M. et al. "Co-administration of Probenecid, an Inhibitor of a cMOAT/MRP-like Plasma Membrane ATPase, Greatly Enhanced the Efficacy of a New 10-Deazaaminopterin against Human Solid Tumors in Vivo." Clinical Cancer Research. 2000. pp. 3705-3712. vol. 6.

Sirotnak, Francis et al. "Analogs of tetrahydrofolate directed at folate-dependent purine biosynthetic enzymes. Characteristics of mediated entry and transport-related resistance in L1210 cells for 5,10-dideazatetrahydrofolate and two 10-alkyl derivatives", Biochemical Pharmacology, 1988, pp. 4775-4777, vol. 37, No. 24, Pergamon Press plc., Great Britain.

Sirotnak, Francis et al., "Stereospecificity at Carbon 6 of Formyltetrahydrofolate as a Competitive Inhibitor of Transport and Cytotoxicity of Methotrexate in Vitro", Biochemical Pharmacology, 1979, pp. 2993-2997, vol. 28, Pergamon Press Ltd., Great Britain.

Sirotnak, F. et al., "New folate analogs of the 10-deaza-aminopterin series Basis for Structural design and biochemical and pharmacologic properties", Cancer Chemotherapy Pharmacology, 1984, pp. 18-25, vol. 12, Springer-Verlag.

Sirotnak, F. et al., "Markedly Improved Efficacy of Edatrexate Compared to Methotrexate in a High-Dose Regimen with Leucovorin Rescue against Metastatic Murine Solid Tumors", Cancer Research, Feb. 1, 1993, pp. 587-591, vol. 53.

Sirotnak, F. et al., "A new analogue of 10-deazaaminopterin with markedly enhanced curative effects against human tumor xenografts in mice", Cancer Chemotherapy Pharmacology, 1998, pp. 313-318, vol. 42, Springer-Verlag.

Skibola, Christine et al., "Genetic susceptibility to lymphoma", Haematologica/The Hematology Journal, 2007, pp. 960-969, vol. 92, No. 7.

Skibola, Christine et al., "Polymorphisms and haplotypes in folate-metabolizing genes and risk of non-Hodgkin lymphoma", Blood, 2004, pp. 2155-2162, vol. 104, www.bloodjournal.org.

Slater, D.N., "The new World Health Organization-European Organization for Research and Treatment of Cancer classification for cutaneous lymphomas: a practical marriage of two giants", British Journal of Dermatology, 2005, pp. 874-880, vol. 153, British Association of Dermatologists.

Takimoto, Chris, "New Antifolates: Pharmacology and Clinical Applications", Oncologist, 1996, pp. 68-81, vol. 1, www.TheOncologist.com.

Toner, Lorraine et al., The Schedule-Dependent Effects of the Novel Antifolate Pralatrexate and Gemcitabine are Superior to Methotrexate and Cytarabine in Models of Human Non-Hodgkin's Lymphoma, Clin Cancer Res, Feb. 1, 2006, pp. 924-932, vol. 12, No. 3, www.aacrjournals.org.

Ueda, Takanori et al. "Inhibitory Action of 10-Deazaaminopterins and Their Polyglutamates on Human Thy,idylate Synthase." Molecular Pharmacology, 1986, pp. 149-153, vol. 30, The American Society for Pharmacology and Experimental Therapeutics.

Vergier, Beatrice et al. "Transformation of mycosis fungoides: clinicopathological and prognostic features of 45 cases." Blood, Apr. 1, 2000, pp. 2212-2218, vol. 95, No. 6.

Vonderheid, Eric et al. "Treatment Planning in cutaneous T-Cell Lymphoma." Dermatologic Therapy 2003, pp. 276-282, vol. 16.

Vrhovac, Radovan et al. "A novel antifolate 10-propargyl-10-deazaaminopterin (PDX) displays synergistic effects with gemcitabine in non-Hodgkin's lymphoma models in vitro and in vivo." 45th Annual Meeting of the American Society of Hematology. Nov. 16, 2003. p. 288b. vol. 102, No. 11.

Wang E S et al. "Activity of a novel anti-folate (PDX, 10 propargyl-10-deazaaminopterin) against human lymphoma is superior to methotrexate and correlates with tumor RFC-1 gene expression." Leukemia and Lymphoma. Jun. 1, 2003. pp. 1027-1035. vol. 44, No. 6.

Wang et al."PDX, a Novel Antifolate with Potent in Vitro and in Vivo Activity in Non-Hodgkin's Lymphoma." Developmental Hematology and the Program for Molecular Pharmacology and Experimental Therapeutics. Abstract 2565, 2001 p. 612a.

SEQUENCE LISTING

<160> NUMBER OF SEQ ID NOS: 18

<210> SEQ ID NO 1
<211> LENGTH: 2839
<212> TYPE: DNA
<213> ORGANISM: Homo sapiens

<400> SEQUENCE: 1

| | | | | | |
|---|---|---|---|---|---|
| gtagtcccgg | agtccgcgtg | cgcggggccg | ggtccgggag | ccccagggca | gccgccccgc | 60 |
| cgagtcgcag | gcacagcgtc | accttcgtcc | cctccggagc | tgcacgtggc | ctgagcagga | 120 |
| tggtgccctc | cagcccagcg | gtggagaagc | aggtgcccgt | ggaacctggg | cctgaccccg | 180 |
| agctccggtc | ctggcggcac | ctcgtgtgct | acctttgctt | ctacggcttc | atggcgcaga | 240 |
| tacggccagg | ggagagcttc | atcaccccct | acctcctggg | gcccgacaag | aacttcacgc | 300 |
| gggagcaggt | cacgaacgag | atcacgccgg | tgctgtcgta | ctcctacctg | gccgtgctgg | 360 |
| tgcccgtgtt | cctgctcacc | gactacctgc | gctacacgcc | ggtgctgctg | ctgcaggggc | 420 |
| tcagcttcgt | gtcggtgtgg | ctgctgctgc | tgctgggcca | ctcggtggcg | cacatgcagc | 480 |
| tcatggagct | cttctacagc | gtcaccatgg | ccgcgcgcat | cgcctattcc | tcctacatct | 540 |
| tctctctcgt | gcggccccgc | cgctaccagc | gtgtggccgg | ctactcgcgc | gctgcggtgc | 600 |
| tgctgggcgt | gttcaccagc | tccgtgctgg | gccagctgct | ggtcactgtg | ggccgagtct | 660 |
| ccttctccac | gctcaactac | atctcgctgg | ccttcctcac | cttcagcgtg | gtcctcgccc | 720 |
| tcttcctgaa | gcgccccaag | cgcagcctct | tcttcaaccg | cgacgaccgg | gggcggtgcg | 780 |
| aaacctcggc | ttcggagctg | gagcgcatga | atcctggccc | aggcgggaag | ctgggacacg | 840 |
| ccctgcgggt | ggcctgtggg | gactcagtgc | tggcgcggat | gctgcgggag | ctgggggaca | 900 |
| gcctgcggcg | gccgcagctg | cgcctgtggt | ccctctggtg | ggtcttcaac | tcggccggct | 960 |
| actacctggt | ggtctactac | gtgcacatcc | tgtggaacga | ggtggacccc | accaccaaca | 1020 |
| gtgcgcgggt | ctacaacggc | gcggcagatg | ctgcctccac | gctgctgggc | gccatcacgt | 1080 |
| ccttcgccgc | gggcttcgtg | aagatccgct | gggcgcgctg | gtccaagctg | ctcatcgcgg | 1140 |
| gcgtcacggc | cacgcaggcg | gggctggtct | tccttctggc | gcacacgcgc | cacccgagca | 1200 |
| gcatctggct | gtgctatgcg | gccttcgtgc | tgttccgcgg | ctcctaccag | ttcctcgtgc | 1260 |
| ccatcgccac | ctttcagatt | gcatcttctc | tgtctaaaga | gctctgtgcc | ctggtcttcg | 1320 |
| gggtcaacac | gttctttgcc | accatcgtca | agaccatcat | cactttcatt | gtctcggacg | 1380 |
| tgcggggcct | gggcctcccg | gtccgcaagc | agttccagtt | atactccgtg | tacttcctga | 1440 |
| tcctgtccat | catctacttc | ttgggggcca | tgctggatgg | cctgcggcac | tgccagcggg | 1500 |
| gccaccaccc | gcggcagccc | ccggcccagg | gcctgaggag | tgccgcggag | gagaaggcag | 1560 |
| cacaggcact | gagcgtgcag | gacaagggcc | tcggaggcct | gcagccagcc | cagagcccgc | 1620 |
| cgctttcccc | agaagacagc | ctgggggctg | tggggccagc | ctccctggag | cagagacaga | 1680 |
| gcgacccata | cctggcccag | gccccggccc | cgcaggcagc | tgaattcctg | agcccagtga | 1740 |
| caacccttc | cccctgcact | ctgtgctccg | cccaagcctc | aggccctgag | gctgcagatg | 1800 |
| agacttgtcc | ccagctggct | gtccatcctc | ctggtgtcag | caagctgggt | ttgcagtgtc | 1860 |
| ttccaagcga | cggtgttcag | aatgtgaacc | agtgactctc | gggcgcccct | gtggtaactt | 1920 |
| tgcaggcggc | cctcagtgca | tccccacgac | ccctgcctcg | agggccgcct | gccttagcaa | 1980 |
| tgggggcctc | cgcttatcct | gctagcaggc | cccctaggat | tcccctgcc | ctgtgccgca | 2040 |

-continued

```
ctctggcggt ggccacagcg tgctggcgac actcagggca gctgcctggc catgctgtcc      2100
ctgcactgtg ccccgcgggc tttgttgctg aagaggtgg gtggtgggct tctgcgtcca       2160
ccaggcctca ctggctcatg ccccttgggg ggcttgagac aaatcctttc tgccccccag      2220
ggctagtgaa gtggcctctt ggataccagc tcagggaca ctggccccac aggagttgtg      2280
agccctctag gcagggtgg gagccgggac cctcaggtgt agctgagctg tgacattgct      2340
ggtcatcctt ggtgctcttg ctttttttgaa agatgctttt ttttttttta actgacgtag     2400
aatgaagaac tgcatgtggc ttctctgtct ctgtggaaaa gccatctcag gttggcggca     2460
gacacattgt catcagaggg gagcagcggc tctggtcctc ggagctggtt cctctctccc     2520
accctaaggg cagccctcca tggtcctgtc tgtccttctg aagtgtgtcc atcctgacct     2580
gcgggtcctc agctgctccc acacttgtgc cagcccggag gggactggtc ccggtcaccg     2640
cggacgtgct ggccttggta tgtgccaggc ttgcctgggc tgggcagcct tggggggct      2700 gcctttgtgg tgggcgctgg ggaagtacgt cccagcggcc tcagggtcta aggagcgcta     2760
gtgccttgcc cacaggtgcg ggaccatctg atgtgatgtg aatactcttc ccacatacat     2820
taaacacact taagtgaga                                                   2839

<210> SEQ ID NO 2
<211> LENGTH: 2839
<212> TYPE: DNA
<213> ORGANISM: Homo sapiens
<220> FEATURE:
<221> NAME/KEY: CDS
<222> LOCATION: (120)..(1895)

<400> SEQUENCE: 2
gtagtcccgg agtccgcgtg cgcggggccg ggtccgggag ccccagggca gccgccccgc       60
cgagtcgcag gcacagcgtc accttcgtcc cctccggagc tgcacgtggc ctgagcagg      119 atg gtg ccc tcc agc cca gcg gtg gag aag cag gtg ccc gtg gaa cct       167
Met Val Pro Ser Ser Pro Ala Val Glu Lys Gln Val Pro Val Glu Pro
1               5                  10                  15 ggg cct gac ccc gag ctc cgg tcc tgg cgg cac ctc gtg tgc tac ctt       215
Gly Pro Asp Pro Glu Leu Arg Ser Trp Arg His Leu Val Cys Tyr Leu
            20                  25                  30 tgc ttc tac ggc ttc atg gcg cag ata cgg cca ggg gag agc ttc atc       263
Cys Phe Tyr Gly Phe Met Ala Gln Ile Arg Pro Gly Glu Ser Phe Ile
        35                  40                  45 acc ccc tac ctc ctg ggg ccc gac aag aac ttc acg cgg gag cag gtc       311
Thr Pro Tyr Leu Leu Gly Pro Asp Lys Asn Phe Thr Arg Glu Gln Val
    50                  55                  60 acg aac gag atc acg ccg gtg ctg tcg tac tcc tac ctg gcc gtg ctg       359
Thr Asn Glu Ile Thr Pro Val Leu Ser Tyr Ser Tyr Leu Ala Val Leu
65                  70                  75                  80 gtg ccc gtg ttc ctg ctc acc gac tac ctg cgc tac acg ccg gtg ctg       407
Val Pro Val Phe Leu Leu Thr Asp Tyr Leu Arg Tyr Thr Pro Val Leu
                85                  90                  95 ctg ctg cag ggg ctc agc ttc gtg tcg gtg tgg ctg ctg ctg ctg           455
Leu Leu Gln Gly Leu Ser Phe Val Ser Val Trp Leu Leu Leu Leu
            100                 105                 110 ggc cac tcg gtg gcg cac atg cag ctc atg gag ctc ttc tac agc gtc       503
Gly His Ser Val Ala His Met Gln Leu Met Glu Leu Phe Tyr Ser Val
        115                 120                 125 acc atg gcc gcg cgc atc gcc tat tcc tcc tac atc ttc tct ctc gtg       551
Thr Met Ala Ala Arg Ile Ala Tyr Ser Ser Tyr Ile Phe Ser Leu Val
    130                 135                 140 cgg ccc gcg cgc tac cag cgt gtg gcc ggc tac tcg cgc gct gcg gtg       599
```

```
          Arg Pro Ala Arg Tyr Gln Arg Val Ala Gly Tyr Ser Arg Ala Ala Val
          145                 150                 155                 160 ctg ctg ggc gtg ttc acc agc tcc gtg ctg ggc cag ctg ctg gtc act        647
Leu Leu Gly Val Phe Thr Ser Ser Val Leu Gly Gln Leu Leu Val Thr
                    165                 170                 175 gtg ggc cga gtc tcc ttc tcc acg ctc aac tac atc tcg ctg gcc ttc        695
Val Gly Arg Val Ser Phe Ser Thr Leu Asn Tyr Ile Ser Leu Ala Phe
            180                 185                 190 ctc acc ttc agc gtg gtc ctc gcc ctc ttc ctg aag cgc ccc aag cgc        743
Leu Thr Phe Ser Val Val Leu Ala Leu Phe Leu Lys Arg Pro Lys Arg
        195                 200                 205 agc ctc ttc ttc aac cgc gac gac cgg ggg cgg tgc gaa acc tcg gct        791
Ser Leu Phe Phe Asn Arg Asp Asp Arg Gly Arg Cys Glu Thr Ser Ala
    210                 215                 220 tcg gag ctg gag cgc atg aat cct ggc cca ggc ggg aag ctg gga cac        839
Ser Glu Leu Glu Arg Met Asn Pro Gly Pro Gly Gly Lys Leu Gly His
225                 230                 235                 240 gcc ctg cgg gtg gcc tgt ggg gac tca gtg ctg gcg cgg atg ctg cgg        887
Ala Leu Arg Val Ala Cys Gly Asp Ser Val Leu Ala Arg Met Leu Arg
                245                 250                 255 gag ctg ggg gac agc ctg cgg cgg ccg cag ctg cgc ctg tgg tcc ctc        935
Glu Leu Gly Asp Ser Leu Arg Arg Pro Gln Leu Arg Leu Trp Ser Leu
            260                 265                 270 tgg tgg gtc ttc aac tcg gcc ggc tac tac ctg gtg gtc tac tac gtg        983
Trp Trp Val Phe Asn Ser Ala Gly Tyr Tyr Leu Val Val Tyr Tyr Val
        275                 280                 285 cac atc ctg tgg aac gag gtg gac ccc acc acc aac agt gcg cgg gtc       1031
His Ile Leu Trp Asn Glu Val Asp Pro Thr Thr Asn Ser Ala Arg Val
    290                 295                 300 tac aac ggc gcg gca gat gct gcc tcc acg ctg ctg ggc gcc atc acg       1079
Tyr Asn Gly Ala Ala Asp Ala Ala Ser Thr Leu Leu Gly Ala Ile Thr
305                 310                 315                 320 tcc ttc gcc gcg ggc ttc gtg aag atc cgc tgg gcg cgc tgg tcc aag       1127
Ser Phe Ala Ala Gly Phe Val Lys Ile Arg Trp Ala Arg Trp Ser Lys
                325                 330                 335 ctg ctc atc gcg ggc gtc acg gcc acg cag gcg ggg ctg gtc ttc ctt       1175
Leu Leu Ile Ala Gly Val Thr Ala Thr Gln Ala Gly Leu Val Phe Leu
            340                 345                 350 ctg gcg cac acg cgc cac ccg agc agc atc tgg ctg tgc tat gcg gcc       1223
Leu Ala His Thr Arg His Pro Ser Ser Ile Trp Leu Cys Tyr Ala Ala
        355                 360                 365 ttc gtg ctg ttc cgc ggc tcc tac cag ttc ctc gtg ccc atc gcc acc       1271
Phe Val Leu Phe Arg Gly Ser Tyr Gln Phe Leu Val Pro Ile Ala Thr
    370                 375                 380 ttt cag att gca tct tct ctg tct aaa gag ctc tgt gcc ctg gtc ttc       1319
Phe Gln Ile Ala Ser Ser Leu Ser Lys Glu Leu Cys Ala Leu Val Phe
385                 390                 395                 400 ggg gtc aac acg ttc ttt gcc acc atc gtc aag acc atc atc act ttc       1367
Gly Val Asn Thr Phe Phe Ala Thr Ile Val Lys Thr Ile Ile Thr Phe
                405                 410                 415 att gtc tcg gac gtg cgg ggc ctg ggc ctc ccg gtc cgc aag cag ttc       1415
Ile Val Ser Asp Val Arg Gly Leu Gly Leu Pro Val Arg Lys Gln Phe
            420                 425                 430 cag tta tac tcc gtg tac ttc ctg atc ctg tcc atc atc tac ttc ttg       1463
Gln Leu Tyr Ser Val Tyr Phe Leu Ile Leu Ser Ile Ile Tyr Phe Leu
        435                 440                 445 ggg gcc atg ctg gat ggc ctg cgg cac tgc cag cgg ggc cac cac ccg       1511
Gly Ala Met Leu Asp Gly Leu Arg His Cys Gln Arg Gly His His Pro
    450                 455                 460 cgg cag ccc ccg gcc cag ggc ctg agg agt gcc gcg gag gag aag gca       1559
```

```
Arg Gln Pro Pro Ala Gln Gly Leu Arg Ser Ala Ala Glu Lys Ala
465                 470                 475                 480 gca cag gca ctg agc gtg cag gac aag ggc ctc gga ggc ctg cag cca      1607
Ala Gln Ala Leu Ser Val Gln Asp Lys Gly Leu Gly Gly Leu Gln Pro
                485                 490                 495 gcc cag agc ccg ccg ctt tcc cca gaa gac agc ctg ggg gct gtg ggg      1655
Ala Gln Ser Pro Pro Leu Ser Pro Glu Asp Ser Leu Gly Ala Val Gly
            500                 505                 510 cca gcc tcc ctg gag cag aga cag agc gac cca tac ctg gcc cag gcc      1703
Pro Ala Ser Leu Glu Gln Arg Gln Ser Asp Pro Tyr Leu Ala Gln Ala
                515                 520                 525 ccg gcc ccg cag gca gct gaa ttc ctg agc cca gtg aca acc cct tcc      1751
Pro Ala Pro Gln Ala Ala Glu Phe Leu Ser Pro Val Thr Thr Pro Ser
        530                 535                 540 ccc tgc act ctg tgc tcc gcc caa gcc tca ggc cct gag gct gca gat      1799
Pro Cys Thr Leu Cys Ser Ala Gln Ala Ser Gly Pro Glu Ala Ala Asp
545                 550                 555                 560 gag act tgt ccc cag ctg gct gtc cat cct cct ggt gtc agc aag ctg      1847
Glu Thr Cys Pro Gln Leu Ala Val His Pro Pro Gly Val Ser Lys Leu
                565                 570                 575 ggt ttg cag tgt ctt cca agc gac ggt gtt cag aat gtg aac cag tga      1895
Gly Leu Gln Cys Leu Pro Ser Asp Gly Val Gln Asn Val Asn Gln
            580                 585                 590 ctctcgggcg ccctgtggt aactttgcag gcggccctca gtgcatcccc acgacccctg      1955
cctcgagggc cgcctgcctt agcaatgggg gcctccgctt atcctgctag caggcccct      2015 aggattcccc ctgccctgtg ccgcactctg gcggtggcca cagcgtgctg cgacactca      2075 gggcagctgc ctggccatgc tgtccctgca ctgtgccccg cgggctttgt tgctggaaga      2135
ggtgggtggt gggcttctgc gtccaccagg cctcactggc tcatgcccct tgggggctt      2195 gagacaaatc ctttctgccc cccagggcta gtgaagtggc ctcttggata ccagctcagg      2255
ggacactggc cccacaggag ttgtgagccc tctaggcag gtgggagcc gggaccctca      2315 ggtgtagctg agctgtgaca ttgctggtca tccttggtgc tcttgctttt ttgaaagatg      2375 ctttttttt ttttaactga cgtagaatga agaactgcat gtggcttctc tgtctctgtg      2435
gaaaagccat ctcaggttgg cggcagacac attgtcatca gaggggagca gcggctctgg      2495
tcctcggagc tggttcctct ctcccaccct aagggcagcc ctccatggtc ctgtctgtcc      2555
ttctgaagtg tgtccatcct gacctgcggg tcctcagctg ctcccacact tgtgccagcc      2615
cggaggggac tggtccccggt caccgcggac gtgctggcct tggtatgtgc caggcttgcc      2675
tgggctgggc agccttgggg gggctgcctt tgtggtgggc gctgggaag tacgtcccag      2735 cggcctcagg gtctaaggag cgctagtgcc ttgcccacag gtgcgggacc atctgatgtg      2795
atgtgaatac tcttcccaca tacattaaac acacttaagt gaga                      2839
```

<210> SEQ ID NO 3
<211> LENGTH: 591
<212> TYPE: PRT
<213> ORGANISM: Homo sapiens

<400> SEQUENCE: 3

```
Met Val Pro Ser Ser Pro Ala Val Glu Lys Gln Val Pro Val Glu Pro
1               5                   10                  15

Gly Pro Asp Pro Glu Leu Arg Ser Trp Arg His Leu Val Cys Tyr Leu
                20                  25                  30

Cys Phe Tyr Gly Phe Met Ala Gln Ile Arg Pro Gly Glu Ser Phe Ile
            35                  40                  45
```

```
Thr Pro Tyr Leu Leu Gly Pro Asp Lys Asn Phe Thr Arg Glu Gln Val
 50                  55                  60

Thr Asn Glu Ile Thr Pro Val Leu Ser Tyr Ser Tyr Leu Ala Val Leu
 65                  70                  75                  80

Val Pro Val Phe Leu Leu Thr Asp Tyr Leu Arg Tyr Thr Pro Val Leu
                 85                  90                  95

Leu Leu Gln Gly Leu Ser Phe Val Ser Val Trp Leu Leu Leu Leu
                100                 105                 110

Gly His Ser Val Ala His Met Gln Leu Met Glu Leu Phe Tyr Ser Val
            115                 120                 125

Thr Met Ala Ala Arg Ile Ala Tyr Ser Ser Tyr Ile Phe Ser Leu Val
    130                 135                 140

Arg Pro Ala Arg Tyr Gln Arg Val Ala Gly Tyr Ser Arg Ala Ala Val
145                 150                 155                 160

Leu Leu Gly Val Phe Thr Ser Val Leu Gly Gln Leu Leu Val Thr
                165                 170                 175

Val Gly Arg Val Ser Phe Ser Thr Leu Asn Tyr Ile Ser Leu Ala Phe
            180                 185                 190

Leu Thr Phe Ser Val Val Leu Ala Leu Phe Leu Lys Arg Pro Lys Arg
    195                 200                 205

Ser Leu Phe Phe Asn Arg Asp Asp Arg Gly Arg Cys Glu Thr Ser Ala
210                 215                 220

Ser Glu Leu Glu Arg Met Asn Pro Gly Pro Gly Lys Leu Gly His
225                 230                 235                 240

Ala Leu Arg Val Ala Cys Gly Asp Ser Val Leu Ala Arg Met Leu Arg
                245                 250                 255

Glu Leu Gly Asp Ser Leu Arg Arg Pro Gln Leu Arg Leu Trp Ser Leu
            260                 265                 270

Trp Trp Val Phe Asn Ser Ala Gly Tyr Tyr Leu Val Val Tyr Tyr Val
    275                 280                 285

His Ile Leu Trp Asn Glu Val Asp Pro Thr Thr Asn Ser Ala Arg Val
290                 295                 300

Tyr Asn Gly Ala Ala Asp Ala Ala Ser Thr Leu Leu Gly Ala Ile Thr
305                 310                 315                 320

Ser Phe Ala Ala Gly Phe Val Lys Ile Arg Trp Ala Arg Trp Ser Lys
                325                 330                 335

Leu Leu Ile Ala Gly Val Thr Ala Thr Gln Ala Gly Leu Val Phe Leu
            340                 345                 350

Leu Ala His Thr Arg His Pro Ser Ile Trp Leu Cys Tyr Ala Ala
    355                 360                 365

Phe Val Leu Phe Arg Gly Ser Tyr Gln Phe Leu Val Pro Ile Ala Thr
370                 375                 380

Phe Gln Ile Ala Ser Ser Leu Ser Lys Glu Leu Cys Ala Leu Val Phe
385                 390                 395                 400

Gly Val Asn Thr Phe Phe Ala Thr Ile Val Lys Thr Ile Ile Thr Phe
                405                 410                 415

Ile Val Ser Asp Val Arg Gly Leu Gly Leu Pro Val Arg Lys Gln Phe
            420                 425                 430

Gln Leu Tyr Ser Val Tyr Phe Leu Ile Leu Ser Ile Ile Tyr Phe Leu
    435                 440                 445

Gly Ala Met Leu Asp Gly Leu Arg His Cys Gln Arg Gly His His Pro
450                 455                 460

Arg Gln Pro Pro Ala Gln Gly Leu Arg Ser Ala Ala Glu Glu Lys Ala
465                 470                 475                 480
```

```
Ala Gln Ala Leu Ser Val Gln Asp Lys Gly Leu Gly Gly Leu Gln Pro
                485                 490                 495

Ala Gln Ser Pro Pro Leu Ser Pro Glu Asp Ser Leu Gly Ala Val Gly
            500                 505                 510

Pro Ala Ser Leu Glu Gln Arg Gln Ser Asp Pro Tyr Leu Ala Gln Ala
        515                 520                 525

Pro Ala Pro Gln Ala Ala Glu Phe Leu Ser Pro Val Thr Thr Pro Ser
    530                 535                 540

Pro Cys Thr Leu Cys Ser Ala Gln Ala Ser Gly Pro Glu Ala Ala Asp
545                 550                 555                 560

Glu Thr Cys Pro Gln Leu Ala Val His Pro Pro Gly Val Ser Lys Leu
                565                 570                 575

Gly Leu Gln Cys Leu Pro Ser Asp Gly Val Gln Asn Val Asn Gln
            580                 585                 590

<210> SEQ ID NO 4
<211> LENGTH: 3932
<212> TYPE: DNA
<213> ORGANISM: Homo sapiens

<400> SEQUENCE: 4
tcccagacag aacctactat gtgcggcggc agctggggcg ggaaggcggg agctgggggc      60
gctgggggcg ctgcggccgc tgcggccgct gcagccgctg cagcgccagg tccacctgg     120 tcggctgcac ctgtggagga ggaggtggat ttcaggcttc ccgtagactg aagaatcgg     180 ctcaaaaccg cttgcctcgc aggggctgag ctggaggcag cgaggccgcc cgacgcaggc     240
ttccggcgag acatggcagg caaggatgg cagcccggcg gcagggcctg gcgaggagcg     300
cgagcccgcg gccgcagttc ccaggcgtct gcgggcgcga gcacgccgcg accctgcgtg     360
cgccggggcg gggggggcggg gcctcgcctg cacaaatggg gacgagggg gcggggcggc     420 cacaatttcg cgccaaactt gaccgcgcgt tctgctgtaa cgagcgggct cggaggtcct     480
cccgctgctg tcatggttgg ttcgctaaac tgcatcgtcg ctgtgtccca gaacatgggc     540
atcggcaaga acgggaccct gccctggcca ccgctcagga tgaattcag atatttccag     600 agaatgacca aacctcttc agtagaaggt aaacagaatc tggtgattat gggtaagaag     660
acctggttct ccattcctga gaagaatcga cctttaaagg gtagaattaa tttagttctc     720
agcagagaac tcaaggaacc tccacaagga gctcattttc tttccagaag tctagatgat     780
gccttaaaac ttactgaaca accagaatta gcaaataaag tagacatggt ctggatagtt     840
ggtggcagtt ctgttatataa ggaagccatg aatcacccag ccatcttaa actatttgtg     900 acaaggatca tgcaagactt tgaaagtgac acgttttttc cagaaattga tttggagaaa     960
tataaacttc tgccagaata cccaggtgtt ctctctgatg tccaggagga gaaaggcatt    1020
aagtacaaat ttgaagtata tgagaagaat gattaatatg aaggtgtttt ctagtttaag    1080
ttgttccccc tccctctgaa aaaagtatgt atttttacat tagaaaaggt ttttgttga     1140 ctttagatct ataattattt ctaagcaact agttttttatt ccccactact cttgtctcta    1200
tcagatacca tttatgagac attcttgcta taactaagtg cttctccaag accccaactg    1260
agtccccagc acctgctaca gtgagctgcc attccacacc catcacatgt ggcactcttg    1320
ccagtccttg acattgtcgg cttttcaca tgttggtaat atttattaaa gatgaagatc    1380 cacatacccct tcaactgagc agtttcacta gtggaaatac caaaagcttc ctacgtgtat    1440
atccagaggt ttgtagataa atgttgccac cttgtttgta acagtgaaaa attgaaaaca    1500
```

```
acctggaagt ccagtgatgg gaaaatgagt atgtttctgt cttagattgg ggaacccaaa    1560
gcagattgca agactgaaat ttcagtgaaa gcagtgtatt tgctaggtca taccagaaat    1620
catcaattga ggtacggaga aactgaactg agaaggtaag aaaagcaatt taaagtcagc    1680
gagcaggttc tcattgataa caagctccat actgctgaga tacagggaaa tggagggggg    1740
aaagctggag tatttgatcc cgcccccctcc ttggttgtca gctccctgtc ctgtgtgtgg    1800
gcggaacata gtccagctgc tctatagcaa gtctcaggtg tttgcagtaa aagctgctg    1860 gcatgcacgg gaacagtgaa tgccaaacac ttaaagcaat tcgatgttta agtatgtaag    1920 ttctttttt tttagacagc gtttcgctct tgttgcccag gctagcatgc aatggtgtga    1980
cctcggctta ctgcaacctc cgccttccca gattcaagcg attctcctgc ctcaggctcc    2040
caagtagcta ggaccaggtg cgcgccacca cgcccggcta ttttttgtat tttgtatttt    2100
tagtagagat ggggtttcac catgttggtc aggctagtct cgaactcgtg accgcaagcg    2160
attcacccac ctcagcctcc caaagtgctg ggattaccgg cttgagccac cacacccggc    2220
acatcttcat tcttttatg tagtaaaaag tataaggcca cacatggttt atttgaagta    2280
ttttataatt taaaaaaata cagaagcagg aaaaccaatt ataagttcaa gtgagggatg    2340
atggttgctt gaaccaaagg gttgcatgta gtaagaaatt gtgatttaag atatattta    2400 aagttataag tagcaggata ttctgatgga gttttgacttt ggttttgggc ccagggagtt    2460
tcagatgcct ttgagaaatg aatgaagtag agagaaaata aaagaaaaac cagccaggca    2520
cagtggctca cacctgtaat cccagcgctt gggaggcta aggcaggcag atcacttgag    2580
accagcttgg gcaacatggc aaagccccat ctctacaaaa aacacaaaaa ttagctgggc    2640
attgtggcgc acacctgtat tcccatctag tcaggaagct gagatggaag aattaattga    2700
gcccacgagt tcaaggctgc agtgagtcgt gattgtgcca ctgcactcca gccggggtga    2760
cagaagagac cttgtctcga aaggaatct gaaaacaatg gaaccatgcc ttcataattc    2820
tagaaagtta ttttcaactg ataaatctat attcacccaa ataatcaagg gtgaaggtaa    2880
aataatacat ttttagacaa gcaaagactc aggggttacc tccatgtgcc cttttaggg    2940 aagctgttgg agaaaatact ccagcaaaat gaaggagtac acaaaccaga gaatgacatg    3000
aatccagcaa ataggatcca acacaggcaa tattccagct atggagctag ctttaaaaag    3060
gaacagtaaa aatattaatc ggttagctgg gtggaatggc ccatgcctgt agtcccagct    3120
actcaggagg ctcagcagca ggacgacttg agcccaagag ttccagacca gcctggccac    3180
cttagtgaga tcccttctct taaaaataat aacttattgc cagatttggg gcatttggaa    3240
agaagttcat tgaagataaa gcaaagtaa aaaaaaaaa aaaaaaaaca aggggaaagg    3300
gttggttagg caatcattct agggcagaaa gaagtacagg ataggaagag cataatacac    3360
tgtttttctc aacaaggagc agtatgtaca cagtcataat gatgtgactg cttagcccct    3420
aaatatggta actactctgg gacaatatgg gaggaaaagt gaagattgtg atggtgtaag    3480
agctaaatcc tcatctgtca tatccagaaa tcactatata atatataata atgaaatgac    3540
taagttatgt gaggaaaaaa acagaagaca ttgctaaaag agttaaaagt cattgctctg    3600
gagaattagg agggatgggg caggggactg ttaggatgca ttataaactg aaaagccttt    3660
ttaaaatttt atgtattaat atatgcattc acttgaaaaa ctaaaaaaaa acaataattt    3720
ggaaaaaccc atgaaggtaa ctaacggaag gaaaaactaa gagaatgaaa agtatttgcc    3780
tctggaaaga acaactggca ggactgttgt tttcattgta agacttttgg agccatttaa    3840
ttgtacttaa ccatttcat ctatttcttt aataagaaca attccatctt aataaagagt    3900
```

```
tacacttgtt aataagtaaa aaaaaaaaaa aa                                     3932

<210> SEQ ID NO 5
<211> LENGTH: 3932
<212> TYPE: DNA
<213> ORGANISM: Homo sapiens
<220> FEATURE:
<221> NAME/KEY: CDS
<222> LOCATION: (493)..(1056)

<400> SEQUENCE: 5
tcccagacag aacctactat gtgcggcggc agctggggcg ggaaggcggg agctgggggc        60
gctgggggcg ctgcggccgc tgcggccgct gcagccgctg cagcgccagg gtccacctgg       120
tcggctgcac ctgtggagga ggaggtggat ttcaggcttc ccgtagactg gaagaatcgg       180
ctcaaaaccg cttgcctcgc aggggctgag ctggaggcag cgaggccgcc cgacgcaggc       240
ttccggcgag acatggcagg caaggatgg cagcccggcg gcagggcctg gcgaggagcg        300
cgagcccgcg gccgcagttc ccaggcgtct gcgggcgcga gcacgccgcg accctgcgtg       360
cgccggggcg ggggggcggg gcctcgcctg cacaaatggg gacgaggggg gcggggcggc       420
cacaatttcg cgccaaactt gaccgcgcgt tctgctgtaa cgagcgggct cggaggtcct       480
cccgctgctg tc atg gtt ggt tcg cta aac tgc atc gtc gct gtg tcc cag      531
              Met Val Gly Ser Leu Asn Cys Ile Val Ala Val Ser Gln
              1               5                   10 aac atg ggc atc ggc aag aac ggg gac ctg ccc tgg cca ccg ctc agg        579
Asn Met Gly Ile Gly Lys Asn Gly Asp Leu Pro Trp Pro Pro Leu Arg
    15                  20                  25 aat gaa ttc aga tat ttc cag aga atg acc aca acc tct tca gta gaa        627
Asn Glu Phe Arg Tyr Phe Gln Arg Met Thr Thr Thr Ser Ser Val Glu
30                  35                  40                  45 ggt aaa cag aat ctg gtg att atg ggt aag aag acc tgg ttc tcc att        675
Gly Lys Gln Asn Leu Val Ile Met Gly Lys Lys Thr Trp Phe Ser Ile
                50                  55                  60 cct gag aag aat cga cct tta aag ggt aga att aat tta gtt ctc agc        723
Pro Glu Lys Asn Arg Pro Leu Lys Gly Arg Ile Asn Leu Val Leu Ser
            65                  70                  75 aga gaa ctc aag gaa cct cca caa gga gct cat ttt ctt tcc aga agt        771
Arg Glu Leu Lys Glu Pro Pro Gln Gly Ala His Phe Leu Ser Arg Ser
        80                  85                  90 cta gat gat gcc tta aaa ctt act gaa caa cca gaa tta gca aat aaa        819
Leu Asp Asp Ala Leu Lys Leu Thr Glu Gln Pro Glu Leu Ala Asn Lys
    95                  100                 105 gta gac atg gtc tgg ata gtt ggt ggc agt tct gtt tat aag gaa gcc        867
Val Asp Met Val Trp Ile Val Gly Gly Ser Ser Val Tyr Lys Glu Ala
110                 115                 120                 125 atg aat cac cca ggc cat ctt aaa cta ttt gtg aca agg atc atg caa        915
Met Asn His Pro Gly His Leu Lys Leu Phe Val Thr Arg Ile Met Gln
                130                 135                 140 gac ttt gaa agt gac acg ttt ttt cca gaa att gat ttg gag aaa tat        963
Asp Phe Glu Ser Asp Thr Phe Phe Pro Glu Ile Asp Leu Glu Lys Tyr
            145                 150                 155 aaa ctt ctg cca gaa tac cca ggt gtt ctc tct gat gtc cag gag gag       1011
Lys Leu Leu Pro Glu Tyr Pro Gly Val Leu Ser Asp Val Gln Glu Glu
        160                 165                 170 aaa ggc att aag tac aaa ttt gaa gta tat gag aag aat gat taa         1056
Lys Gly Ile Lys Tyr Lys Phe Glu Val Tyr Glu Lys Asn Asp
    175                 180                 185 tatgaaggtg ttttctagtt taagttgttc ccctccctc tgaaaaagt atgtatttt       1116 acattagaaa aggtttttg ttgactttag atctataatt atttctaagc aactagtttt      1176
```

```
tattccccac tactcttgtc tctatcagat accatttatg agacattctt gctataacta   1236
agtgcttctc caagacccca actgagtccc cagcacctgc tacagtgagc tgccattcca   1296
cacccatcac atgtggcact cttgccagtc cttgacattg tcgggctttt cacatgttgg   1356
taatatttat taaagatgaa gatccacata cccttcaact gagcagtttc actagtggaa   1416
ataccaaaag cttcctacgt gtatatccag aggtttgtag ataaatgttg ccaccttgtt   1476
tgtaacagtg aaaaattgaa acaacctgg aagtccagtg atgggaaaat gagtatgttt    1536
ctgtcttaga ttggggaacc caaagcagat tgcaagactg aaatttcagt gaaagcagtg   1596
tatttgctag gtcataccag aaatcatcaa ttgaggtacg gagaaactga actgagaagg   1656
taagaaaagc aatttaaagt cagcgagcag gttctcattg ataacaagct ccatactgct   1716
gagatacagg gaaatggagg ggggaaagct ggagtattga tcccgccccc ctccttggtt   1776
gtcagctccc tgtcctgtgt gtgggcggaa catagtccag ctgctctata gcaagtctca   1836
ggtgtttgca gtaagaagct gctggcatgc acgggaacag tgaatgccaa acacttaaag   1896
caattcgatg tttaagtatg taagttcttt tttttttaga cagcgtttcg ctcttgttgc   1956
ccaggctagc atgcaatggt gtgacctcgg cttactgcaa cctccgcctt cccagattca   2016
agcgattctc ctgcctcagg ctcccaagta gctaggacca ggtgcgcgcc accacgcccg   2076
gctaattttt gtattttgta tttttagtag agatgggggtt tcaccatgtt ggtcaggcta   2136
gtctcgaact cgtgaccgca agcgattcac ccacctcagc ctcccaaagt gctgggatta   2196
ccggcttgag ccaccacacc cggcacatct tcattctttt tatgtagtaa aaagtataag   2256
gccacacatg gtttatttga agtatttat aatttaaaaa aatacagaag caggaaaacc    2316
aattataagt tcaagtgagg gatgatggtt gcttgaacca aagggttgca tgtagtaaga   2376
aattgtgatt taagatatat tttaaagtta taagtagcag gatattctga tggagtttga   2436
ctttggtttt ggggcccaggg agtttcagat gcctttgaga aatgaatgaa gtagagagaa   2496
aataaaagaa aaaccagcca ggcacagtgg ctcacacctg taatcccagc gctttgggag   2556
gctaaggcag gcagatcact tgagaccagc ttgggcaaca tggcaaagcc ccatctctac   2616
aaaaaacaca aaaattagct gggcattgtg gcgcacacct gtattcccat ctagtcagga   2676
agctgagatg gaagaattaa ttgagcccac gagttcaagg ctgcagtgag tcgtgattgt   2736
gccactgcac tccagccggg gtgacagaag agaccttgtc tcgaaaagga atctgaaaac   2796
aatggaacca tgccttcata attctagaaa gttattttca actgataaat ctatattcac   2856
ccaaataatc aagggtgaag gtaaaataat acattttag acaagcaaag actcaggggt    2916
tacctccatg tgccctttt agggaagctg ttggagaaaa tactccagca aaatgaagga    2976
gtacacaaac cagagaatga catgaatcca gcaaatagga tccaacacag gcaatattcc   3036
agctatggag ctagctttaa aaaggaacag taaaaatatt aatcggttag ctgggtggaa   3096
tggcccatgc ctgtagtccc agctactcag gaggctcagc agcaggacga cttgagccca   3156
agagttccag accagcctgg ccaccttagt gagatcccctt ctcttaaaaa taataactta  3216
ttgccagatt tggggcattt ggaaagaagt tcattgaaga taaagcaaaa gtaaaaaaaa   3276
aaaaaaaaaa aacaagggga aagggttggt taggcaatca ttctagggca gaaagaagta   3336
caggatagga agagcataat acactgtttt tctcaacaag gagcagtatg tacacagtca   3396
taatgatgtg actgcttagc ccctaaaatat ggtaactact ctgggacaat atgggaggaa  3456
aagtgaagat tgtgatggtg taagagctaa atcctcatct gtcatatcca gaaatcacta   3516
tataatatat aataatgaaa tgactaagtt atgtgaggaa aaaaacagaa gacattgcta   3576
```

-continued

| | |
|---|---|
| aaagagttaa aagtcattgc tctggagaat taggagggat ggggcagggg actgttagga | 3636 |
| tgcattataa actgaaaagc cttttttaaaa ttttatgtat taatatatgc attcacttga | 3696 |
| aaaactaaaa aaaaacaata atttggaaaa acccatgaag gtaactaacg gaaggaaaaa | 3756 |
| ctaagagaat gaaaagtatt tgcctctgga agaacaact ggcaggactg ttgttttcat | 3816 |
| tgtaagactt ttggagccat ttaattgtac ttaaccattt tcatctattt ctttaataag | 3876 |
| aacaattcca tcttaataaa gagttacact tgttaataag taaaaaaaaa aaaaaa | 3932 |

<210> SEQ ID NO 6
<211> LENGTH: 187
<212> TYPE: PRT
<213> ORGANISM: Homo sapiens

<400> SEQUENCE: 6

Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185

<210> SEQ ID NO 7
<211> LENGTH: 1536
<212> TYPE: DNA
<213> ORGANISM: Homo sapiens

<400> SEQUENCE: 7

| | |
|---|---|
| ggggggggggg ggaccacttg gcctgcctcc gtcccgccgc gccacttggc ctgcctccgt | 60 |
| cccgccgcgc cacttcgcct gcctccgtcc cccgcccgcc gcgccatgcc tgtggccggc | 120 |
| tcggagctgc cgcgccggcc cttgcccccc gccgcacagg agcgggacgc cgagccgcgt | 180 |
| ccgccgcacg gggagctgca gtacctgggg cagatccaac acatcctccg ctgcggcgtc | 240 |
| aggaaggacg accgcacggg caccggcacc ctgtcggtat tcggcatgca ggcgcgctac | 300 |
| agcctgagag atgaattccc tctgctgaca accaaacgtg tgttctggaa gggtgttttg | 360 |
| gaggagttgc tgtggtttat caagggatcc acaaatgcta aagagctgtc ttccaaggga | 420 |
| gtgaaaatct gggatgccaa tggatcccga gacttttgg acagcctggg attctccacc | 480 |

```
agagaagaag gggacttggg cccagtttat ggcttccagt ggaggcattt tggggcagaa    540
tacagagata tggaatcaga ttattcagga cagggagttg accaactgca aagagtgatt    600
gacaccatca aaaccaaccc tgacgacaga agaatcatca tgtgcgcttg aatccaaga     660 gatcttcctc tgatggcgct gcctccatgc catgccctct gccagttcta tgtggtgaac    720
agtgagctgt cctgccagct gtaccagaga tcgggagaca tgggcctcgg tgtgcctttc    780
aacatcgcca gctacgccct gctcacgtac atgattgcgc acatcacggg cctgaagcca    840
ggtgacttta tacacacttt gggagatgca catatttacc tgaatcacat cgagccactg    900
aaaattcagc ttcagcgaga acccagacct ttcccaaagc tcaggattct tcgaaaagtt    960
gagaaaattg atgacttcaa agctgaagac tttcagattg aagggtacaa tccgcatcca   1020
actattaaaa tggaaatggc tgtttagggt gctttcaaag gagcttgaag gatattgtca   1080
gtctttaggg gttgggctgg atgccgaggt aaagttctt tttgctctaa agaaaaagg    1140 aactaggtca aaaatctgtc cgtgacctat cagttattaa ttttttaagga tgttgccact   1200 ggcaaatgta actgtgccag ttcttttccat aataaaaggc tttgagttaa ctcactgagg   1260
gtatctgaca atgctgaggt tatgaacaaa gtgaggagaa tgaaatgtat gtgctcttag   1320
caaaaacatg tatgtgcatt tcaatcccac gtacttataa agaaggttgg tgaatttcac   1380
aagctatttt tggaatattt ttagaatatt ttaagaattt cacaagctat tccctcaaat   1440
ctgagggagc tgagtaacac catcgatcat gatgtagagt gtggttatga actttatagt   1500
tgttttatat gttgctataa taaagaagtg ttctgc                             1536

<210> SEQ ID NO 8
<211> LENGTH: 1536
<212> TYPE: DNA
<213> ORGANISM: Homo sapiens
<220> FEATURE:
<221> NAME/KEY: CDS
<222> LOCATION: (106)..(1047)

<400> SEQUENCE: 8
gggggggggg ggaccacttg gcctgcctcc gtcccgccgc gccacttggc ctgcctccgt     60
cccgccgcgc cacttcgcct gcctccgtcc ccgcccgcc gcgcc atg cct gtg gcc    117
                                              Met Pro Val Ala
                                              1 ggc tcg gag ctg ccg cgc cgg ccc ttg ccc ccc gcc gca cag gag cgg    165
Gly Ser Glu Leu Pro Arg Arg Pro Leu Pro Pro Ala Ala Gln Glu Arg
5                   10                  15                  20 gac gcc gag ccg cgt ccg ccg cac ggg gag ctg cag tac ctg ggg cag    213
Asp Ala Glu Pro Arg Pro Pro His Gly Glu Leu Gln Tyr Leu Gly Gln
                25                  30                  35 atc caa cac atc ctc cgc tgc ggc gtc agg aag gac gac cgc acg ggc    261
Ile Gln His Ile Leu Arg Cys Gly Val Arg Lys Asp Asp Arg Thr Gly
            40                  45                  50 acc ggc acc ctg tcg gta ttc ggc atg cag gcg cgc tac agc ctg aga    309
Thr Gly Thr Leu Ser Val Phe Gly Met Gln Ala Arg Tyr Ser Leu Arg
        55                  60                  65 gat gaa ttc cct ctg ctg aca acc aaa cgt gtg ttc tgg aag ggt gtt    357
Asp Glu Phe Pro Leu Leu Thr Thr Lys Arg Val Phe Trp Lys Gly Val
    70                  75                  80 ttg gag gag ttg ctg tgg ttt atc aag gga tcc aca aat gct aaa gag    405
Leu Glu Glu Leu Leu Trp Phe Ile Lys Gly Ser Thr Asn Ala Lys Glu
85                  90                  95                 100 ctg tct tcc aag gga gtg aaa atc tgg gat gcc aat gga tcc cga gac    453
Leu Ser Ser Lys Gly Val Lys Ile Trp Asp Ala Asn Gly Ser Arg Asp
```

```
                  105                 110                 115
ttt ttg gac agc ctg gga ttc tcc acc aga gaa gaa ggg gac ttg ggc    501
Phe Leu Asp Ser Leu Gly Phe Ser Thr Arg Glu Glu Gly Asp Leu Gly
        120                 125                 130 cca gtt tat ggc ttc cag tgg agg cat ttt ggg gca gaa tac aga gat    549
Pro Val Tyr Gly Phe Gln Trp Arg His Phe Gly Ala Glu Tyr Arg Asp
    135                 140                 145 atg gaa tca gat tat tca gga cag gga gtt gac caa ctg caa aga gtg    597
Met Glu Ser Asp Tyr Ser Gly Gln Gly Val Asp Gln Leu Gln Arg Val
150                 155                 160 att gac acc atc aaa acc aac cct gac gac aga aga atc atc atg tgc    645
Ile Asp Thr Ile Lys Thr Asn Pro Asp Asp Arg Arg Ile Ile Met Cys
165                 170                 175                 180 gct tgg aat cca aga gat ctt cct ctg atg gcg ctg cct cca tgc cat    693
Ala Trp Asn Pro Arg Asp Leu Pro Leu Met Ala Leu Pro Pro Cys His
                185                 190                 195 gcc ctc tgc cag ttc tat gtg gtg aac agt gag ctg tcc tgc cag ctg    741
Ala Leu Cys Gln Phe Tyr Val Val Asn Ser Glu Leu Ser Cys Gln Leu
            200                 205                 210 tac cag aga tcg gga gac atg ggc ctc ggt gtg cct ttc aac atc gcc    789
Tyr Gln Arg Ser Gly Asp Met Gly Leu Gly Val Pro Phe Asn Ile Ala
        215                 220                 225 agc tac gcc ctg ctc acg tac atg att gcg cac atc acg ggc ctg aag    837
Ser Tyr Ala Leu Leu Thr Tyr Met Ile Ala His Ile Thr Gly Leu Lys
    230                 235                 240 cca ggt gac ttt ata cac act ttg gga gat gca cat att tac ctg aat    885
Pro Gly Asp Phe Ile His Thr Leu Gly Asp Ala His Ile Tyr Leu Asn
245                 250                 255                 260 cac atc gag cca ctg aaa att cag ctt cag cga gaa ccc aga cct ttc    933
His Ile Glu Pro Leu Lys Ile Gln Leu Gln Arg Glu Pro Arg Pro Phe
                265                 270                 275 cca aag ctc agg att ctt cga aaa gtt gag aaa att gat gac ttc aaa    981
Pro Lys Leu Arg Ile Leu Arg Lys Val Glu Lys Ile Asp Asp Phe Lys
            280                 285                 290 gct gaa gac ttt cag att gaa ggg tac aat ccg cat cca act att aaa   1029
Ala Glu Asp Phe Gln Ile Glu Gly Tyr Asn Pro His Pro Thr Ile Lys
        295                 300                 305 atg gaa atg gct gtt tag ggtgctttca aaggagcttg aaggatattg           1077
Met Glu Met Ala Val
        310 tcagtcttta ggggttgggc tggatgccga ggtaaaagtt cttttgctc taaaagaaaa   1137 aggaactagg tcaaaaatct gtccgtgacc tatcagttat taattttaa ggatgttgcc   1197 actggcaaat gtaactgtgc cagttctttc cataataaaa ggctttgagt taactcactg   1257 agggtatctg acaatgctga ggttatgaac aaagtgagga gaatgaaatg tatgtgctct   1317 tagcaaaaac atgtatgtgc atttcaatcc cacgtactta taaagaaggt tggtgaattt   1377 cacaagctat ttttggaata ttttagaat attttaagaa tttcacaagc tattccctca   1437 aatctgaggg agctgagtaa caccatcgat catgatgtag agtgtggtta tgaactttat   1497 agttgtttta tatgttgcta taataaagaa gtgttctgc                         1536

<210> SEQ ID NO 9
<211> LENGTH: 313
<212> TYPE: PRT
<213> ORGANISM: Homo sapiens

<400> SEQUENCE: 9

Met Pro Val Ala Gly Ser Glu Leu Pro Arg Arg Pro Leu Pro Pro Ala
1               5                   10                  15
```

Ala Gln Glu Arg Asp Ala Glu Pro Arg Pro His Gly Glu Leu Gln
            20                  25                  30

Tyr Leu Gly Gln Ile Gln His Ile Leu Arg Cys Gly Val Arg Lys Asp
        35                  40                  45

Asp Arg Thr Gly Thr Gly Thr Leu Ser Val Phe Gly Met Gln Ala Arg
50                  55                  60

Tyr Ser Leu Arg Asp Glu Phe Pro Leu Leu Thr Thr Lys Arg Val Phe
65                  70                  75                  80

Trp Lys Gly Val Leu Glu Glu Leu Leu Trp Phe Ile Lys Gly Ser Thr
                85                  90                  95

Asn Ala Lys Glu Leu Ser Ser Lys Gly Val Lys Ile Trp Asp Ala Asn
            100                 105                 110

Gly Ser Arg Asp Phe Leu Asp Ser Leu Gly Phe Ser Thr Arg Glu Glu
        115                 120                 125

Gly Asp Leu Gly Pro Val Tyr Gly Phe Gln Trp Arg His Phe Gly Ala
130                 135                 140

Glu Tyr Arg Asp Met Glu Ser Asp Tyr Ser Gly Gln Gly Val Asp Gln
145                 150                 155                 160

Leu Gln Arg Val Ile Asp Thr Ile Lys Thr Asn Pro Asp Asp Arg Arg
                165                 170                 175

Ile Ile Met Cys Ala Trp Asn Pro Arg Asp Leu Pro Leu Met Ala Leu
            180                 185                 190

Pro Pro Cys His Ala Leu Cys Gln Phe Tyr Val Val Asn Ser Glu Leu
        195                 200                 205

Ser Cys Gln Leu Tyr Gln Arg Ser Gly Asp Met Gly Leu Gly Val Pro
210                 215                 220

Phe Asn Ile Ala Ser Tyr Ala Leu Leu Thr Tyr Met Ile Ala His Ile
225                 230                 235                 240

Thr Gly Leu Lys Pro Gly Asp Phe Ile His Thr Leu Gly Asp Ala His
                245                 250                 255

Ile Tyr Leu Asn His Ile Glu Pro Leu Lys Ile Gln Leu Gln Arg Glu
            260                 265                 270

Pro Arg Pro Phe Pro Lys Leu Arg Ile Leu Arg Lys Val Glu Lys Ile
        275                 280                 285

Asp Asp Phe Lys Ala Glu Asp Phe Gln Ile Glu Gly Tyr Asn Pro His
290                 295                 300

Pro Thr Ile Lys Met Glu Met Ala Val
305                 310

<210> SEQ ID NO 10
<211> LENGTH: 1280
<212> TYPE: DNA
<213> ORGANISM: Homo sapiens

<400> SEQUENCE: 10
tgccgcagcc cccgcccgcc cgcagagctt ttgaaaggcg gcgggaggcg gcgagcgcca      60
tggccagtcc gggctgcctg ctgtgcgtgc tgggcctgct actctgcggg gcggcgagcc     120
tcgagctgtc tagaccccac ggcgacaccg ccaagaagcc catcatcgga atattaatgc     180
aaaaatgccg taataaagtc atgaaaaact atggaagata ctatattgct gcgtcctatg     240
taaagtactt ggagtctgca ggtgcgagag ttgtaccagt aaggctggat cttacagaga     300
aagactatga atactttttc aaatctatta tggaatcct tttccctgga ggaagtgttg     360
acctcagacg ctcagattat gctaaagtgg ccaaatatat ttataacttg tccatacaga     420

-continued

```
gttttgatga tggagactat tttcctgtgt ggggcacatg ccttggattt gaagagcttt    480
cactgctgat tagtggagag tgcttattaa ctgccacaga tactgttgac gtggcaatgc    540
cgctgaactt cactggaggt caattgcaca gcagaatgtt ccagaatttt cctactgagt    600
tgttgctgtc attagcagta gaacctctga ctgccaattt ccataagtgg agcctctccg    660
tgaagaattt tacaatgaat gaaaagttaa agaagttttt caatgtctta actacaaata    720
cagatggcaa gattgagttt atttcaacaa tggaaggata taagtatcca gtatatggtg    780
tccagtggca tccagagaaa gcaccttatg agtggaagaa tttggatggc atttcccatg    840
cacctaatgc tgtgaaaacc gcattttatt tagcagagtt ttttgttaat gaagctcgga    900
aaaacaacca tcattttaaa tctgaatctg aagaggagaa agcattgatt tatcagttca    960
gtccaattta tactgaaaat atttcttcat ttcagcaatg ttacatattt gattgaaagt   1020
cttcaatttg ttaacagagc aaatttgaat aattccatga ttaaactgtt agaataactt   1080
gctactcatg gcaagattag gaagtcacag attcttttct ataatgtgcc tggctctgat   1140
tcttcattat gtatgtgact atttatataa cattagataa ttaaatagtg agacataaat   1200
agagtgcttt ttcatggaaa agccttctta tatctgaaga ttgaaaaata aatttactga   1260
aatacaaaaa aaaaaaaaaa                                               1280
```

<210> SEQ ID NO 11
<211> LENGTH: 1280
<212> TYPE: DNA
<213> ORGANISM: Homo sapiens
<220> FEATURE:
<221> NAME/KEY: CDS
<222> LOCATION: (60)..(1016)

<400> SEQUENCE: 11

```
tgccgcagcc cccgcccgcc cgcagagctt ttgaaaggcg gcgggaggcg gcgagcgcc          59 atg gcc agt ccg ggc tgc ctg ctg tgc gtg ctg ggc ctg cta ctc tgc         107
Met Ala Ser Pro Gly Cys Leu Leu Cys Val Leu Gly Leu Leu Leu Cys
1               5                  10                  15 ggg gcg gcg agc ctc gag ctg tct aga ccc cac ggc gac acc gcc aag         155
Gly Ala Ala Ser Leu Glu Leu Ser Arg Pro His Gly Asp Thr Ala Lys
            20                  25                  30 aag ccc atc atc gga ata tta atg caa aaa tgc cgt aat aaa gtc atg         203
Lys Pro Ile Ile Gly Ile Leu Met Gln Lys Cys Arg Asn Lys Val Met
        35                  40                  45 aaa aac tat gga aga tac tat att gct gcg tcc tat gta aag tac ttg         251
Lys Asn Tyr Gly Arg Tyr Tyr Ile Ala Ala Ser Tyr Val Lys Tyr Leu
    50                  55                  60 gag tct gca ggt gcg aga gtt gta cca gta agg ctg gat ctt aca gag         299
Glu Ser Ala Gly Ala Arg Val Val Pro Val Arg Leu Asp Leu Thr Glu
65                  70                  75                  80 aaa gac tat gaa ata ctt ttc aaa tct att aat gga atc ctt ttc cct         347
Lys Asp Tyr Glu Ile Leu Phe Lys Ser Ile Asn Gly Ile Leu Phe Pro
                85                  90                  95 gga gga agt gtt gac ctc aga cgc tca gat tat gct aaa gtg gcc aaa         395
Gly Gly Ser Val Asp Leu Arg Arg Ser Asp Tyr Ala Lys Val Ala Lys
            100                 105                 110 ata ttt tat aac ttg tcc ata cag agt ttt gat gat gga gac tat ttt         443
Ile Phe Tyr Asn Leu Ser Ile Gln Ser Phe Asp Asp Gly Asp Tyr Phe
        115                 120                 125 cct gtg tgg ggc aca tgc ctt gga ttt gaa gag ctt tca ctg ctg att         491
Pro Val Trp Gly Thr Cys Leu Gly Phe Glu Glu Leu Ser Leu Leu Ile
    130                 135                 140 agt gga gag tgc tta tta act gcc aca gat act gtt gac gtg gca atg         539
Ser Gly Glu Cys Leu Leu Thr Ala Thr Asp Thr Val Asp Val Ala Met
```

```
Ser Gly Glu Cys Leu Leu Thr Ala Thr Asp Thr Val Asp Val Ala Met
145                 150                 155                 160 ccg ctg aac ttc act gga ggt caa ttg cac agc aga atg ttc cag aat    587
Pro Leu Asn Phe Thr Gly Gly Gln Leu His Ser Arg Met Phe Gln Asn
                165                 170                 175 ttt cct act gag ttg ttg ctg tca tta gca gta gaa cct ctg act gcc    635
Phe Pro Thr Glu Leu Leu Leu Ser Leu Ala Val Glu Pro Leu Thr Ala
            180                 185                 190 aat ttc cat aag tgg agc ctc tcc gtg aag aat ttt aca atg aat gaa    683
Asn Phe His Lys Trp Ser Leu Ser Val Lys Asn Phe Thr Met Asn Glu
        195                 200                 205 aag tta aag aag ttt ttc aat gtc tta act aca aat aca gat ggc aag    731
Lys Leu Lys Lys Phe Phe Asn Val Leu Thr Thr Asn Thr Asp Gly Lys
    210                 215                 220 att gag ttt att tca aca atg gaa gga tat aag tat cca gta tat ggt    779
Ile Glu Phe Ile Ser Thr Met Glu Gly Tyr Lys Tyr Pro Val Tyr Gly
225                 230                 235                 240 gtc cag tgg cat cca gag aaa gca cct tat gag tgg aag aat ttg gat    827
Val Gln Trp His Pro Glu Lys Ala Pro Tyr Glu Trp Lys Asn Leu Asp
                245                 250                 255 ggc att tcc cat gca cct aat gct gtg aaa acc gca ttt tat tta gca    875
Gly Ile Ser His Ala Pro Asn Ala Val Lys Thr Ala Phe Tyr Leu Ala
            260                 265                 270 gag ttt ttt gtt aat gaa gct cgg aaa aac aac cat cat ttt aaa tct    923
Glu Phe Phe Val Asn Glu Ala Arg Lys Asn Asn His His Phe Lys Ser
        275                 280                 285 gaa tct gaa gag gag aaa gca ttg att tat cag ttc agt cca att tat    971
Glu Ser Glu Glu Glu Lys Ala Leu Ile Tyr Gln Phe Ser Pro Ile Tyr
    290                 295                 300 act gga aat att tct tca ttt cag caa tgt tac ata ttt gat tga       1016
Thr Gly Asn Ile Ser Ser Phe Gln Gln Cys Tyr Ile Phe Asp
305                 310                 315 aagtcttcaa tttgttaaca gagcaaattt gaataattcc atgattaaac tgttagaata  1076
acttgctact catggcaaga ttaggaagtc acagattctt ttctataatg tgcctggctc  1136
tgattcttca ttatgtatgt gactatttat ataacattag ataattaaat agtgagacat  1196
aaatagagtg cttttcatg gaaaagcctt cttatatctg aagattgaaa ataaattta    1256 ctgaaataca aaaaaaaaaa aaaa                                         1280

<210> SEQ ID NO 12
<211> LENGTH: 318
<212> TYPE: PRT
<213> ORGANISM: Homo sapiens

<400> SEQUENCE: 12

Met Ala Ser Pro Gly Cys Leu Leu Cys Val Leu Gly Leu Leu Leu Cys
1               5                   10                  15

Gly Ala Ala Ser Leu Glu Leu Ser Arg Pro His Gly Asp Thr Ala Lys
            20                  25                  30

Lys Pro Ile Ile Gly Ile Leu Met Gln Lys Cys Arg Asn Lys Val Met
        35                  40                  45

Lys Asn Tyr Gly Arg Tyr Tyr Ile Ala Ala Ser Tyr Val Lys Tyr Leu
    50                  55                  60

Glu Ser Ala Gly Ala Arg Val Val Pro Val Arg Leu Asp Leu Thr Glu
65                  70                  75                  80

Lys Asp Tyr Glu Ile Leu Phe Lys Ser Ile Asn Gly Ile Leu Phe Pro
                85                  90                  95

Gly Gly Ser Val Asp Leu Arg Arg Ser Asp Tyr Ala Lys Val Ala Lys
```

```
                   100                 105                 110
Ile Phe Tyr Asn Leu Ser Ile Gln Ser Phe Asp Asp Gly Asp Tyr Phe
            115                 120                 125

Pro Val Trp Gly Thr Cys Leu Gly Phe Glu Glu Leu Ser Leu Leu Ile
        130                 135                 140

Ser Gly Glu Cys Leu Leu Thr Ala Thr Asp Thr Val Asp Val Ala Met
145                 150                 155                 160

Pro Leu Asn Phe Thr Gly Gly Gln Leu His Ser Arg Met Phe Gln Asn
                165                 170                 175

Phe Pro Thr Glu Leu Leu Leu Ser Leu Ala Val Glu Pro Leu Thr Ala
            180                 185                 190

Asn Phe His Lys Trp Ser Leu Ser Val Lys Asn Phe Thr Met Asn Glu
        195                 200                 205

Lys Leu Lys Lys Phe Phe Asn Val Leu Thr Thr Asn Thr Asp Gly Lys
    210                 215                 220

Ile Glu Phe Ile Ser Thr Met Glu Gly Tyr Lys Tyr Pro Val Tyr Gly
225                 230                 235                 240

Val Gln Trp His Pro Glu Lys Ala Pro Tyr Glu Trp Lys Asn Leu Asp
                245                 250                 255

Gly Ile Ser His Ala Pro Asn Ala Val Lys Thr Ala Phe Tyr Leu Ala
            260                 265                 270

Glu Phe Phe Val Asn Glu Ala Arg Lys Asn Asn His His Phe Lys Ser
        275                 280                 285

Glu Ser Glu Glu Glu Lys Ala Leu Ile Tyr Gln Phe Ser Pro Ile Tyr
    290                 295                 300

Thr Gly Asn Ile Ser Ser Phe Gln Gln Cys Tyr Ile Phe Asp
305                 310                 315

<210> SEQ ID NO 13
<211> LENGTH: 2158
<212> TYPE: DNA
<213> ORGANISM: Homo sapiens

<400> SEQUENCE: 13
gcgcggcata acgacccagg tcgcggcgcg gcggggcttg agcgcgtggc cggtgccgca    60
ggagccgagc atggagtacc aggatgccgt gcgcatgctc aatacccgtgc agaccaatgc   120 cggctacctg gagcaggtga agcgccagcg gggtgaccct cagacacagt tggaagccat   180
ggaactgtac ctggcacgga gtgggctgca ggtggaggac ttggaccggc tgaacatcat   240
ccacgtcact gggacgaagg ggaagggctc cacctgtgcc ttcacggaat gtatcctccg   300
aagctatggc ctgaagacgg gattctttag ctctccccac ctggtgcagg ttcgggagcg   360
gatccgcatc aatgggcagc ccatcagtcc tgagctcttc accaagtact tctggcgcct   420
ctaccaccgg ctggaggaga ccaaggatgg cagctgtgtc tccatgcccc cctacttccg   480
cttcctgaca ctcatggcct tccacgtctt cctccaagag aaggtggacc tggcagtggt   540
ggaggtgggc attggcgggg cttatgactg caccaacatc atcaggaagc tgtggtgtg   600 cggagtctcc tctcttggca tcgaccacac cagcctcctg ggggatacgg tggagaagat   660
cgcatggcag aaaggggggca tctttaagca aggtgtccct gccttcactg tgctccaacc   720
tgaaggtccc ctggcagtgc tgaggaccg agcccagcag atctcatgtc ctctataacct   780 gtgtccgatg ctggaggccc tcgaggaagg ggggccgccg ctgaccctgg gctggagggg   840
ggagcaccag cggtccaacg ccgccttggc cttgcagctg gcccactgct ggctgcagcg   900
gcaggaccgc catggtgctg gggagccaaa ggcatccagg ccagggctcc tgtggcagct   960
```

```
gcccctggca cctgtgttcc agcccacatc ccacatgcgg ctcgggcttc ggaacacgga    1020
gtggccgggc cggacgcagg tgctgcggcg cgggcccctc acctggtacc tggacggtgc    1080
gcacaccgcc agcagcgcgc aggcctgcgt gcgctggttc cgccaggcgc tgcagggccg    1140
cgagaggccg agcggtggcc ccgaggttcg agtcttgctc ttcaatgcta ccggggaccg    1200
ggacccggcg ccctgctga agctgctgca gccctgccag tttgactatg ccgtcttctg    1260
ccctaacctg acagaggtgt catccacagg caacgcagac caacagaact tcacagtgac    1320
actggaccag gtcctgctcc gctgcctgga acaccagcag cactggaacc acctggacga    1380
agagcaggcc agcccggacc tctggagtgc ccccagccca gagcccggtg ggtccgcatc    1440
cctgcttctg cgcccccacc caccccacac ctgcagtgcc agctcccctcg tcttcagctg    1500 catttcacat gccttgcaat ggatcagcca aggccgagac cccatcttcc agccacctag    1560
tcccccaaag ggcctcctca cccaccctgt ggctcacagt ggggccagca tactccgtga    1620
ggctgctgcc atccatgtgc tagtcactgg cagcctgcac ctggtgggtg gtgtcctgaa    1680
gctgctggag cccgcactgt cccagtagcc aaggcccggg gttggaggtg ggagcttccc    1740
acacctgcct gcgttctccc catgaactta catactaggg gccttttgtt tttggctttc    1800
ctggttctgt ctagactggc ctaggggcca gggctttggg atgggaggcc gggagaggat    1860
gtctttttta aggctctgtg ccttggtctc tccttcctct tggctgagat agcagagggg    1920
ctccccgggt ctctcactgt tgcagtggcc tggccgttca gcctgtctcc cccaacaccc    1980
cgcctgcctc ctggctcagg cccagcttat tgtgtgcgct gcctggccag gccctgggtc    2040
ttgccatgtg ctgggtggta gatttcctcc tcccagtgcc ttctgggaag ggagagggcc    2100
tctgcctggg acactgcggg acagagggtg gctggagtga attaaagcct ttgtttttt     2158
```

<210> SEQ ID NO 14
<211> LENGTH: 2158
<212> TYPE: DNA
<213> ORGANISM: Homo sapiens
<220> FEATURE:
<221> NAME/KEY: CDS
<222> LOCATION: (71)..(1708)

<400> SEQUENCE: 14

```
gcgcggcata acgacccagg tcgcggcgcg gcggggcttg agcgcgtggc cggtgccgca    60
ggagccgagc atg gag tac cag gat gcc gtg cgc atg ctc aat acc ctg       109
            Met Glu Tyr Gln Asp Ala Val Arg Met Leu Asn Thr Leu
            1               5                   10 cag acc aat gcc ggc tac ctg gag cag gtg aag cgc cag cgg ggt gac      157
Gln Thr Asn Ala Gly Tyr Leu Glu Gln Val Lys Arg Gln Arg Gly Asp
 15                  20                  25 cct cag aca cag ttg gaa gcc atg gaa ctg tac ctg gca cgg agt ggg      205
Pro Gln Thr Gln Leu Glu Ala Met Glu Leu Tyr Leu Ala Arg Ser Gly
 30              35                  40                  45 ctg cag gtg gag gac ttg gac cgg ctg aac atc atc cac gtc act ggg      253
Leu Gln Val Glu Asp Leu Asp Arg Leu Asn Ile Ile His Val Thr Gly
                 50                  55                  60 acg aag ggg aag ggc tcc acc tgt gcc ttc acg gaa tgt atc ctc cga      301
Thr Lys Gly Lys Gly Ser Thr Cys Ala Phe Thr Glu Cys Ile Leu Arg
             65                  70                  75 agc tat ggc ctg aag acg gga ttc ttt agc tct ccc cac ctg gtg cag      349
Ser Tyr Gly Leu Lys Thr Gly Phe Phe Ser Ser Pro His Leu Val Gln
         80                  85                  90 gtt cgg gag cgg atc cgc atc aat ggg cag ccc atc agt cct gag ctc      397
Val Arg Glu Arg Ile Arg Ile Asn Gly Gln Pro Ile Ser Pro Glu Leu
```

```
                    95                  100                 105
ttc acc aag tac ttc tgg cgc ctc tac cac cgg ctg gag gag acc aag      445
Phe Thr Lys Tyr Phe Trp Arg Leu Tyr His Arg Leu Glu Glu Thr Lys
110                 115                 120                 125 gat ggc agc tgt gtc tcc atg ccc ccc tac ttc cgc ttc ctg aca ctc      493
Asp Gly Ser Cys Val Ser Met Pro Pro Tyr Phe Arg Phe Leu Thr Leu
                130                 135                 140 atg gcc ttc cac gtc ttc ctc caa gag aag gtg gac ctg gca gtg gtg      541
Met Ala Phe His Val Phe Leu Gln Glu Lys Val Asp Leu Ala Val Val
            145                 150                 155 gag gtg ggc att ggc ggg gct tat gac tgc acc aac atc atc agg aag      589
Glu Val Gly Ile Gly Gly Ala Tyr Asp Cys Thr Asn Ile Ile Arg Lys
        160                 165                 170 cct gtg gtg tgc gga gtc tcc tct ctt ggc atc gac cac acc agc ctc      637
Pro Val Val Cys Gly Val Ser Ser Leu Gly Ile Asp His Thr Ser Leu
    175                 180                 185 ctg ggg gat acg gtg gag aag atc gca tgg cag aaa ggg ggc atc ttt      685
Leu Gly Asp Thr Val Glu Lys Ile Ala Trp Gln Lys Gly Gly Ile Phe
190                 195                 200                 205 aag caa ggt gtc cct gcc ttc act gtg ctc caa cct gaa ggt ccc ctg      733
Lys Gln Gly Val Pro Ala Phe Thr Val Leu Gln Pro Glu Gly Pro Leu
                210                 215                 220 gca gtg ctg agg gac cga gcc cag cag atc tca tgt cct cta tac ctg      781
Ala Val Leu Arg Asp Arg Ala Gln Gln Ile Ser Cys Pro Leu Tyr Leu
            225                 230                 235 tgt ccg atg ctg gag gcc ctc gag gaa ggg ggg ccg ccg ctg acc ctg      829
Cys Pro Met Leu Glu Ala Leu Glu Glu Gly Gly Pro Pro Leu Thr Leu
        240                 245                 250 ggc ctg gag ggg gag cac cag cgg tcc aac gcc gcc ttg gcc ttg cag      877
Gly Leu Glu Gly Glu His Gln Arg Ser Asn Ala Ala Leu Ala Leu Gln
    255                 260                 265 ctg gcc cac tgc tgg ctg cag cgg cag gac cgc cat ggt gct ggg gag      925
Leu Ala His Cys Trp Leu Gln Arg Gln Asp Arg His Gly Ala Gly Glu
270                 275                 280                 285 cca aag gca tcc agg cca ggg ctc ctg tgg cag ctg ccc ctg gca cct      973
Pro Lys Ala Ser Arg Pro Gly Leu Leu Trp Gln Leu Pro Leu Ala Pro
                290                 295                 300 gtg ttc cag ccc aca tcc cac atg cgg ctc ggg ctt cgg aac acg gag     1021
Val Phe Gln Pro Thr Ser His Met Arg Leu Gly Leu Arg Asn Thr Glu
            305                 310                 315 tgg ccg ggc cgg acg cag gtg ctg cgg cgc ggg ccc ctc acc tgg tac     1069
Trp Pro Gly Arg Thr Gln Val Leu Arg Arg Gly Pro Leu Thr Trp Tyr
        320                 325                 330 ctg gac ggt gcg cac acc gcc agc agc gcg cag gcc tgc gtg cgc tgg     1117
Leu Asp Gly Ala His Thr Ala Ser Ser Ala Gln Ala Cys Val Arg Trp
    335                 340                 345 ttc cgc cag gcg ctg cag ggc cgc gag agg ccg agc ggt ggc ccc gag     1165
Phe Arg Gln Ala Leu Gln Gly Arg Glu Arg Pro Ser Gly Gly Pro Glu
350                 355                 360                 365 gtt cga gtc ttg ctc ttc aat gct acc ggg gac cgg gac ccg gcg gcc     1213
Val Arg Val Leu Leu Phe Asn Ala Thr Gly Asp Arg Asp Pro Ala Ala
                370                 375                 380 ctg ctg aag ctg ctg cag ccc tgc cag ttt gac tat gcc gtc ttc tgc     1261
Leu Leu Lys Leu Leu Gln Pro Cys Gln Phe Asp Tyr Ala Val Phe Cys
            385                 390                 395 cct aac ctg aca gag gtg tca tcc aca ggc aac gca gac caa cag aac     1309
Pro Asn Leu Thr Glu Val Ser Ser Thr Gly Asn Ala Asp Gln Gln Asn
        400                 405                 410 ttc aca gtg aca ctg gac cag gtc ctg ctc cgc tgc ctg gaa cac cag     1357
Phe Thr Val Thr Leu Asp Gln Val Leu Leu Arg Cys Leu Glu His Gln
```

```
                415                 420                 425
cag cac tgg aac cac ctg gac gaa gag cag gcc agc ccg gac ctc tgg          1405
Gln His Trp Asn His Leu Asp Glu Glu Gln Ala Ser Pro Asp Leu Trp
430                 435                 440                 445 agt gcc ccc agc cca gag ccc ggt ggg tcc gca tcc ctg ctt ctg gcg          1453
Ser Ala Pro Ser Pro Glu Pro Gly Gly Ser Ala Ser Leu Leu Leu Ala
                    450                 455                 460 ccc cac cca ccc cac acc tgc agt gcc agc tcc ctc gtc ttc agc tgc          1501
Pro His Pro Pro His Thr Cys Ser Ala Ser Ser Leu Val Phe Ser Cys
                465                 470                 475 att tca cat gcc ttg caa tgg atc agc caa ggc cga gac ccc atc ttc          1549
Ile Ser His Ala Leu Gln Trp Ile Ser Gln Gly Arg Asp Pro Ile Phe
            480                 485                 490 cag cca cct agt ccc cca aag ggc ctc ctc acc cac cct gtg gct cac          1597
Gln Pro Pro Ser Pro Pro Lys Gly Leu Leu Thr His Pro Val Ala His
        495                 500                 505 agt ggg gcc agc ata ctc cgt gag gct gct gcc atc cat gtg cta gtc          1645
Ser Gly Ala Ser Ile Leu Arg Glu Ala Ala Ala Ile His Val Leu Val
    510                 515                 520                 525 act ggc agc ctg cac ctg gtg ggt ggt gtc ctg aag ctg ctg gag ccc          1693
Thr Gly Ser Leu His Leu Val Gly Gly Val Leu Lys Leu Leu Glu Pro
                    530                 535                 540 gca ctg tcc cag tag ccaaggcccg gggttggagg tgggagcttc ccacacctgc          1748
Ala Leu Ser Gln
            545 ctgcgttctc cccatgaact tacatactag gtgccttttg tttttggctt tcctggttct        1808 gtctagactg gcctaggggc cagggctttg ggatgggagg ccgggagagg atgtcttttt        1868 taaggctctg tgccttggtc tctccttcct cttggctgag atagcagagg ggctccccgg        1928 gtctctcact gttgcagtgg cctggccgtt cagcctgtct cccccaacac cccgcctgcc        1988 tcctggctca ggcccagctt attgtgtgcg ctgcctggcc aggccctggg tcttgccatg        2048 tgctgggtgg tagatttcct cctcccagtg ccttctggga aggagaggg cctctgcctg         2108 ggacactgcg ggacagaggg tggctggagt gaattaaagc ctttgttttt                   2158
```

<210> SEQ ID NO 15
<211> LENGTH: 545
<212> TYPE: PRT
<213> ORGANISM: Homo sapiens

<400> SEQUENCE: 15

```
Met Glu Tyr Gln Asp Ala Val Arg Met Leu Asn Thr Leu Gln Thr Asn
1               5                   10                  15

Ala Gly Tyr Leu Glu Gln Val Lys Arg Gln Arg Gly Asp Pro Gln Thr
            20                  25                  30

Gln Leu Glu Ala Met Glu Leu Tyr Leu Ala Arg Ser Gly Leu Gln Val
        35                  40                  45

Glu Asp Leu Asp Arg Leu Asn Ile Ile His Val Thr Gly Thr Lys Gly
    50                  55                  60

Lys Gly Ser Thr Cys Ala Phe Thr Glu Cys Ile Leu Arg Ser Tyr Gly
65                  70                  75                  80

Leu Lys Thr Gly Phe Phe Ser Ser Pro His Leu Val Gln Val Arg Glu
                85                  90                  95

Arg Ile Arg Ile Asn Gly Gln Pro Ile Ser Pro Glu Leu Phe Thr Lys
            100                 105                 110

Tyr Phe Trp Arg Leu Tyr His Arg Leu Glu Glu Thr Lys Asp Gly Ser
        115                 120                 125
```

```
Cys Val Ser Met Pro Pro Tyr Phe Arg Phe Leu Thr Leu Met Ala Phe
    130                 135                 140

His Val Phe Leu Gln Glu Lys Val Asp Leu Ala Val Val Glu Val Gly
145                 150                 155                 160

Ile Gly Gly Ala Tyr Asp Cys Thr Asn Ile Ile Arg Lys Pro Val Val
                165                 170                 175

Cys Gly Val Ser Ser Leu Gly Ile Asp His Thr Ser Leu Leu Gly Asp
            180                 185                 190

Thr Val Glu Lys Ile Ala Trp Gln Lys Gly Ile Phe Lys Gln Gly
        195                 200                 205

Val Pro Ala Phe Thr Val Leu Gln Pro Glu Gly Pro Leu Ala Val Leu
210                 215                 220

Arg Asp Arg Ala Gln Gln Ile Ser Cys Pro Leu Tyr Leu Cys Pro Met
225                 230                 235                 240

Leu Glu Ala Leu Glu Glu Gly Gly Pro Pro Leu Thr Leu Gly Leu Glu
                245                 250                 255

Gly Glu His Gln Arg Ser Asn Ala Ala Leu Ala Leu Gln Leu Ala His
                260                 265                 270

Cys Trp Leu Gln Arg Gln Asp Arg His Gly Ala Gly Glu Pro Lys Ala
        275                 280                 285

Ser Arg Pro Gly Leu Leu Trp Gln Leu Pro Leu Ala Pro Val Phe Gln
290                 295                 300

Pro Thr Ser His Met Arg Leu Gly Leu Arg Asn Thr Glu Trp Pro Gly
305                 310                 315                 320

Arg Thr Gln Val Leu Arg Arg Gly Pro Leu Thr Trp Tyr Leu Asp Gly
                325                 330                 335

Ala His Thr Ala Ser Ser Ala Gln Ala Cys Val Arg Trp Phe Arg Gln
                340                 345                 350

Ala Leu Gln Gly Arg Glu Arg Pro Ser Gly Gly Pro Glu Val Arg Val
                355                 360                 365

Leu Leu Phe Asn Ala Thr Gly Asp Arg Asp Pro Ala Ala Leu Leu Lys
        370                 375                 380

Leu Leu Gln Pro Cys Gln Phe Asp Tyr Ala Val Phe Cys Pro Asn Leu
385                 390                 395                 400

Thr Glu Val Ser Ser Thr Gly Asn Ala Asp Gln Gln Asn Phe Thr Val
                405                 410                 415

Thr Leu Asp Gln Val Leu Leu Arg Cys Leu Glu His Gln Gln His Trp
        420                 425                 430

Asn His Leu Asp Glu Glu Gln Ala Ser Pro Asp Leu Trp Ser Ala Pro
                435                 440                 445

Ser Pro Glu Pro Gly Gly Ser Ala Ser Leu Leu Ala Pro His Pro
450                 455                 460

Pro His Thr Cys Ser Ala Ser Ser Leu Val Phe Ser Cys Ile Ser His
465                 470                 475                 480

Ala Leu Gln Trp Ile Ser Gln Gly Arg Asp Pro Ile Phe Gln Pro Pro
                485                 490                 495

Ser Pro Pro Lys Gly Leu Leu Thr His Pro Val Ala His Ser Gly Ala
                500                 505                 510

Ser Ile Leu Arg Glu Ala Ala Ile His Val Leu Thr Gly Ser
                515                 520                 525

Leu His Leu Val Gly Gly Val Leu Lys Leu Glu Pro Ala Leu Ser
        530                 535                 540

Gln
545
```

<210> SEQ ID NO 16
<211> LENGTH: 3291
<212> TYPE: DNA
<213> ORGANISM: Homo sapiens

<400> SEQUENCE: 16

| | | | | | |
|---|---|---|---|---|---|
| accgggcaag | cgggaaccag | gtggccaccc | ggtgtcggtt | tcattttcct | ttggaatttc | 60 |
| tgctttacag | acagaacaat | ggcagcccga | gtacttataa | ttggcagtgg | aggaagggaa | 120 |
| catacgctgg | cctggaaact | tgcacagtct | catcatgtca | aacaagtgtt | ggttgcccca | 180 |
| ggaaacgcag | gcactgcctg | ctctgaaaag | atttcaaata | ccgccatctc | aatcagtgac | 240 |
| cacactgccc | ttgctcaatt | ctgcaaagag | aagaaaattg | aatttgtagt | tgttggacca | 300 |
| gaagcacctc | tggctgctgg | gattgttggg | aacctgaggt | ctgcaggagt | gcaatgcttt | 360 |
| ggcccaacag | cagaagcggc | tcagttagag | tccagcaaaa | ggtttgccaa | agagtttatg | 420 |
| gacagacatg | gaatcccaac | cgcacaatgg | aaggctttca | ccaaacctga | gaagcctgc | 480 |
| agcttcattt | tgagtgcaga | cttccctgct | ttggttgtga | aggccagtgg | tcttgcagct | 540 |
| ggaaaagggg | tgattgttgc | aaagagcaaa | gaagaggcct | gcaaagctgt | acaagagatc | 600 |
| atgcaggaga | aagcctttgg | ggcagctgga | gaaacaattg | tcattgaaga | acttcttgac | 660 |
| ggagaagagg | tgtcgtgtct | gtgtttcact | gatggcaaga | ctgtggcccc | catgcccca | 720 |
| gcacaggacc | ataagcgatt | actggaggga | gatggtggcc | taacacaggg | gggaatggga | 780 |
| gcctattgtc | cagccctca | ggtttctaat | gatctattac | taaaaattaa | agatactgtt | 840 |
| cttcagagga | cagtggatgg | catgcagcaa | gagggtactc | catatacagg | tattctctat | 900 |
| gctggaataa | tgctgaccaa | gaatggccca | aaagttctag | agtttaattg | ccgttttggt | 960 |
| gatccagagt | gccaagtaat | cctcccactt | cttaaaagtg | atctttatga | agtgattcag | 1020 |
| tccaccttag | atggactgct | ctgcacatct | ctgcctgttt | ggctagaaaa | ccacaccgcc | 1080 |
| ctaactgttg | tcatggcaag | taaaggttat | cctggagact | acaccaaggg | tgtagagata | 1140 |
| acagggtttc | ctgaggctca | agctctagga | ctggaggtgt | tccatgcagg | cactgccctc | 1200 |
| aaaaatggca | aagtagtaac | tcatgggggt | agagttcttg | cagtcacagc | catccgggaa | 1260 |
| aatctctat | cagcccttga | ggaagccaag | aaaggactag | ctgctataaa | gtttgaggga | 1320 |
| gcaatttata | ggaaagacgt | cggctttcgt | gccatagctt | tcctccagca | gcccaggagt | 1380 |
| ttgacttaca | aggaatctgg | agtagatatc | gcagctggaa | atatgctggt | caagaaaatt | 1440 |
| cagcctttag | caaaagccac | ttccagatca | ggctgtaaag | ttgatcttgg | aggttttgct | 1500 |
| ggtcttttg | atttaaaagc | agctggtttc | aaagatcccc | ttctggcctc | tggaacagat | 1560 |
| ggcgttggaa | ctaaactaaa | gattgcccag | ctatgcaata | aacatgatac | cattggtcaa | 1620 |
| gatttggtag | caatgtgtgt | taatgatatt | ctggcacaag | gagcagagcc | cctcttcttc | 1680 |
| cttgattact | tttcctgtgg | aaaacttgac | ctcagtgtaa | ctgaagctgt | tgttgctgga | 1740 |
| attgctaaag | cttgtggaaa | agctggatgt | gctctccttg | gaggtgaaac | agcagaaatg | 1800 |
| cctgacatgt | atccccctgg | agagtatgac | ctagctgggt | ttgccgttgg | tgccatggag | 1860 |
| cgagatcaga | aactccctca | cctggaaaga | atcactgagg | gtgatgttgt | tgttggaata | 1920 |
| gcttcatctg | gtcttcatag | caatggattt | agccttgtga | ggaaatcgt | tgcaaaatct | 1980 |
| tccctccagt | actcctctcc | agcacctgat | ggttgtggtg | accagacttt | agggggactta | 2040 |
| cttctcacgc | ctaccagaat | ctacagccat | tcactgttac | ctgtcctacg | ttcaggacat | 2100 |
| gtcaaagcct | tgcccatat | tactggtgga | ggattactag | agaacatccc | cagagtcctc | 2160 |

-continued

```
cctgagaaac ttggggtaga tttagatgcc cagacctgga ggatcccag ggttttctca      2220 tggttgcagc aggaaggaca cctctctgag gaagagatgg ccagaacatt taactgtggg      2280
gttggcgctg tccttgtggt atcaaaggag cagacagagc agattctgag ggatatccag      2340
cagcacaagg aagaagcctg ggtgattggc agtgtggttg cacgagctga aggttcccca      2400
cgtgtgaaag tcaagaatct gattgaaagc atgcaaataa atgggtcagt gttgaagaat      2460
ggctccctga caaatcattt ctcttttgaa aaaaaaagg ccagagtggc tgtcttaata      2520
tctggaacag gatcgaacct gcaagcactt atagacagta ctcgggaacc aaatagctct      2580
gcacaaattg atattgttat ctccaacaaa gccgcagtag ctgggttaga taaagcggaa      2640
agagctggta ttcccactag agtaattaat cataaactgt ataaaaatcg tgtagaattt      2700
gacagtgcaa ttgacctagt ccttgaagag ttctccatag acatagtctg tcttgcagga      2760
ttcatgagaa ttcttttctgg cccctttgtc aaaagtgga atggaaaaat gctcaatatc      2820
cacccatcct tgctcccttc ttttaagggt tcaaatgccc atgagcaagc cctggaaacc      2880
ggagtcacag ttactgggtg cactgtacac tttgtagctg aagatgtgga tgctggacag      2940
attattttgc aagaagctgt tcccgtgaag aggggtgata ctgtcgcaac tctttctgaa      3000
agagtaaaat tagcagaaca taaaatattt cctgcagccc ttcagctggt ggccagtgga      3060
actgtacagc ttgagaaaaa tggcaagatc tgttgggtta agaggaatg aagccttta      3120 attcagaaat ggggccagtt tagaaagaat tatttgctgt ttgcatggtg gttttttatc      3180
atggacttgg cccaaaagaa aaactgctaa aagacaaaaa agacctcacc cttacttcat      3240 ctatttttt aataaataga gactcactaa aaaaaaaaaa aaaaaaaaa a               3291
```

<210> SEQ ID NO 17
<211> LENGTH: 3291
<212> TYPE: DNA
<213> ORGANISM: Homo sapiens
<220> FEATURE:
<221> NAME/KEY: CDS
<222> LOCATION: (79)..(3111)

<400> SEQUENCE: 17

```
accgggcaag cgggaaccag gtggccaccc ggtgtcggtt tcattttcct ttggaatttc       60
tgctttacag acagaaca atg gca gcc cga gta ctt ata att ggc agt gga        111
                    Met Ala Ala Arg Val Leu Ile Ile Gly Ser Gly
                    1               5                   10 gga agg gaa cat acg ctg gcc tgg aaa ctt gca cag tct cat cat gtc        159
Gly Arg Glu His Thr Leu Ala Trp Lys Leu Ala Gln Ser His His Val
            15                  20                  25 aaa caa gtg ttg gtt gcc cca gga aac gca ggc act gcc tgc tct gaa        207
Lys Gln Val Leu Val Ala Pro Gly Asn Ala Gly Thr Ala Cys Ser Glu
        30                  35                  40 aag att tca aat acc gcc atc tca atc agt gac cac act gcc ctt gct        255
Lys Ile Ser Asn Thr Ala Ile Ser Ile Ser Asp His Thr Ala Leu Ala
    45                  50                  55 caa ttc tgc aaa gag aag aaa att gaa ttt gta gtt gtt gga cca gaa        303
Gln Phe Cys Lys Glu Lys Lys Ile Glu Phe Val Val Val Gly Pro Glu
60                  65                  70                  75 gca cct ctg gct gct ggg att gtt ggg aac ctg agg tct gca gga gtg        351
Ala Pro Leu Ala Ala Gly Ile Val Gly Asn Leu Arg Ser Ala Gly Val
                80                  85                  90 caa tgc ttt ggc cca aca gca gaa gcg gct cag tta gag tcc agc aaa        399
Gln Cys Phe Gly Pro Thr Ala Glu Ala Ala Gln Leu Glu Ser Ser Lys
            95                  100                 105
```

```
agg ttt gcc aaa gag ttt atg gac aga cat gga atc cca acc gca caa    447
Arg Phe Ala Lys Glu Phe Met Asp Arg His Gly Ile Pro Thr Ala Gln
        110                 115                 120 tgg aag gct ttc acc aaa cct gaa gaa gcc tgc agc ttc att ttg agt    495
Trp Lys Ala Phe Thr Lys Pro Glu Glu Ala Cys Ser Phe Ile Leu Ser
    125                 130                 135 gca gac ttc cct gct ttg gtt gtg aag gcc agt ggt ctt gca gct gga    543
Ala Asp Phe Pro Ala Leu Val Val Lys Ala Ser Gly Leu Ala Ala Gly
140                 145                 150                 155 aaa ggg gtg att gtt gca aag agc aaa gaa gag gcc tgc aaa gct gta    591
Lys Gly Val Ile Val Ala Lys Ser Lys Glu Glu Ala Cys Lys Ala Val
                160                 165                 170 caa gag atc atg cag gag aaa gcc ttt ggg gca gct gga gaa aca att    639
Gln Glu Ile Met Gln Glu Lys Ala Phe Gly Ala Ala Gly Glu Thr Ile
            175                 180                 185 gtc att gaa gaa ctt ctt gac gga gaa gag gtg tcg tgt ctg tgt ttc    687
Val Ile Glu Glu Leu Leu Asp Gly Glu Glu Val Ser Cys Leu Cys Phe
        190                 195                 200 act gat ggc aag act gtg gcc ccc atg ccc cca gca cag gac cat aag    735
Thr Asp Gly Lys Thr Val Ala Pro Met Pro Pro Ala Gln Asp His Lys
    205                 210                 215 cga tta ctg gag gga gat ggt ggc cct aac aca ggg gga atg gga gcc    783
Arg Leu Leu Glu Gly Asp Gly Gly Pro Asn Thr Gly Gly Met Gly Ala
220                 225                 230                 235 tat tgt cca gcc cct cag gtt tct aat gat cta tta cta aaa att aaa    831
Tyr Cys Pro Ala Pro Gln Val Ser Asn Asp Leu Leu Leu Lys Ile Lys
                240                 245                 250 gat act gtt ctt cag agg aca gtg gat ggc atg cag caa gag ggt act    879
Asp Thr Val Leu Gln Arg Thr Val Asp Gly Met Gln Gln Glu Gly Thr
            255                 260                 265 cca tat aca ggt att ctc tat gct gga ata atg ctg acc aag aat ggc    927
Pro Tyr Thr Gly Ile Leu Tyr Ala Gly Ile Met Leu Thr Lys Asn Gly
        270                 275                 280 cca aaa gtt cta gag ttt aat tgc cgt ttt ggt gat cca gag tgc caa    975
Pro Lys Val Leu Glu Phe Asn Cys Arg Phe Gly Asp Pro Glu Cys Gln
    285                 290                 295 gta atc ctc cca ctt ctt aaa agt gat ctt tat gaa gtg att cag tcc   1023
Val Ile Leu Pro Leu Leu Lys Ser Asp Leu Tyr Glu Val Ile Gln Ser
300                 305                 310                 315 acc tta gat gga ctg ctc tgc aca tct ctg cct gtt tgg cta gaa aac   1071
Thr Leu Asp Gly Leu Leu Cys Thr Ser Leu Pro Val Trp Leu Glu Asn
                320                 325                 330 cac acc gcc cta act gtt gtc atg gca agt aaa ggt tat cct gga gac   1119
His Thr Ala Leu Thr Val Val Met Ala Ser Lys Gly Tyr Pro Gly Asp
            335                 340                 345 tac acc aag ggt gta gag ata aca ggg ttt cct gag gct caa gct cta   1167
Tyr Thr Lys Gly Val Glu Ile Thr Gly Phe Pro Glu Ala Gln Ala Leu
        350                 355                 360 gga ctg gag gtg ttc cat gca ggc act gcc ctc aaa aat ggc aaa gta   1215
Gly Leu Glu Val Phe His Ala Gly Thr Ala Leu Lys Asn Gly Lys Val
    365                 370                 375 gta act cat ggg ggt aga gtt ctt gca gtc aca gcc atc cgg gaa aat   1263
Val Thr His Gly Gly Arg Val Leu Ala Val Thr Ala Ile Arg Glu Asn
380                 385                 390                 395 ctc ata tca gcc ctt gag gaa gcc aag aaa gga cta gct gct ata aag   1311
Leu Ile Ser Ala Leu Glu Glu Ala Lys Lys Gly Leu Ala Ala Ile Lys
                400                 405                 410 ttt gag gga gca att tat agg aaa gac gtc ggc ttt cgt gcc ata gct   1359
Phe Glu Gly Ala Ile Tyr Arg Lys Asp Val Gly Phe Arg Ala Ile Ala
            415                 420                 425
```

```
ttc ctc cag cag ccc agg agt ttg act tac aag gaa tct gga gta gat    1407
Phe Leu Gln Gln Pro Arg Ser Leu Thr Tyr Lys Glu Ser Gly Val Asp
        430                 435                 440 atc gca gct gga aat atg ctg gtc aag aaa att cag cct tta gca aaa    1455
Ile Ala Ala Gly Asn Met Leu Val Lys Lys Ile Gln Pro Leu Ala Lys
445                 450                 455 gcc act tcc aga tca ggc tgt aaa gtt gat ctt gga ggt ttt gct ggt    1503
Ala Thr Ser Arg Ser Gly Cys Lys Val Asp Leu Gly Gly Phe Ala Gly
460                 465                 470                 475 ctt ttt gat tta aaa gca gct ggt ttc aaa gat ccc ctt ctg gcc tct    1551
Leu Phe Asp Leu Lys Ala Ala Gly Phe Lys Asp Pro Leu Leu Ala Ser
                480                 485                 490 gga aca gat ggc gtt gga act aaa cta aag att gcc cag cta tgc aat    1599
Gly Thr Asp Gly Val Gly Thr Lys Leu Lys Ile Ala Gln Leu Cys Asn
495                 500                 505 aaa cat gat acc att ggt caa gat ttg gta gca atg tgt gtt aat gat    1647
Lys His Asp Thr Ile Gly Gln Asp Leu Val Ala Met Cys Val Asn Asp
        510                 515                 520 att ctg gca caa gga gca gag ccc ctc ttc ttc ctt gat tac ttt tcc    1695
Ile Leu Ala Gln Gly Ala Glu Pro Leu Phe Phe Leu Asp Tyr Phe Ser
525                 530                 535 tgt gga aaa ctt gac ctc agt gta act gaa gct gtt gtt gct gga att    1743
Cys Gly Lys Leu Asp Leu Ser Val Thr Glu Ala Val Val Ala Gly Ile
540                 545                 550                 555 gct aaa gct tgt gga aaa gct gga tgt gct ctc ctt gga ggt gaa aca    1791
Ala Lys Ala Cys Gly Lys Ala Gly Cys Ala Leu Leu Gly Gly Glu Thr
                560                 565                 570 gca gaa atg cct gac atg tat ccc cct gga gag tat gac cta gct ggg    1839
Ala Glu Met Pro Asp Met Tyr Pro Pro Gly Glu Tyr Asp Leu Ala Gly
                575                 580                 585 ttt gcc gtt ggt gcc atg gag cga gat cag aaa ctc cct cac ctg gaa    1887
Phe Ala Val Gly Ala Met Glu Arg Asp Gln Lys Leu Pro His Leu Glu
        590                 595                 600 aga atc act gag ggt gat gtt gtt gtt gga ata gct tca tct ggt ctt    1935
Arg Ile Thr Glu Gly Asp Val Val Val Gly Ile Ala Ser Ser Gly Leu
605                 610                 615 cat agc aat gga ttt agc ctt gtg agg aaa atc gtt gca aaa tct tcc    1983
His Ser Asn Gly Phe Ser Leu Val Arg Lys Ile Val Ala Lys Ser Ser
620                 625                 630                 635 ctc cag tac tcc tct cca gca cct gat ggt tgt ggt gac cag act tta    2031
Leu Gln Tyr Ser Ser Pro Ala Pro Asp Gly Cys Gly Asp Gln Thr Leu
                640                 645                 650 ggg gac tta ctt ctc acg cct acc aga atc tac agc cat tca ctg tta    2079
Gly Asp Leu Leu Leu Thr Pro Thr Arg Ile Tyr Ser His Ser Leu Leu
            655                 660                 665 cct gtc cta cgt tca gga cat gtc aaa gcc ttt gcc cat att act ggt    2127
Pro Val Leu Arg Ser Gly His Val Lys Ala Phe Ala His Ile Thr Gly
            670                 675                 680 gga gga tta cta gag aac atc ccc aga gtc ctc cct gag aaa ctt ggg    2175
Gly Gly Leu Leu Glu Asn Ile Pro Arg Val Leu Pro Glu Lys Leu Gly
        685                 690                 695 gta gat tta gat gcc cag acc tgg agg atc ccc agg gtt ttc tca tgg    2223
Val Asp Leu Asp Ala Gln Thr Trp Arg Ile Pro Arg Val Phe Ser Trp
700                 705                 710                 715 ttg cag cag gaa gga cac ctc tct gag gaa gag atg gcc aga aca ttt    2271
Leu Gln Gln Glu Gly His Leu Ser Glu Glu Glu Met Ala Arg Thr Phe
                720                 725                 730 aac tgt ggg gtt ggc gct gtc ctt gtg gta tca aag gag cag aca gag    2319
Asn Cys Gly Val Gly Ala Val Leu Val Val Ser Lys Glu Gln Thr Glu
            735                 740                 745
```

```
cag att ctg agg gat atc cag cag cac aag gaa gaa gcc tgg gtg att    2367
Gln Ile Leu Arg Asp Ile Gln Gln His Lys Glu Glu Ala Trp Val Ile
        750                 755                 760 ggc agt gtg gtt gca cga gct gaa ggt tcc cca cgt gtg aaa gtc aag    2415
Gly Ser Val Val Ala Arg Ala Glu Gly Ser Pro Arg Val Lys Val Lys
765                 770                 775 aat ctg att gaa agc atg caa ata aat ggg tca gtg ttg aag aat ggc    2463
Asn Leu Ile Glu Ser Met Gln Ile Asn Gly Ser Val Leu Lys Asn Gly
    780                 785                 790                 795 tcc ctg aca aat cat ttc tct ttt gaa aaa aag gcc aga gtg gct        2511
Ser Leu Thr Asn His Phe Ser Phe Glu Lys Lys Lys Ala Arg Val Ala
                800                 805                 810 gtc tta ata tct gga aca gga tcg aac ctg caa gca ctt ata gac agt    2559
Val Leu Ile Ser Gly Thr Gly Ser Asn Leu Gln Ala Leu Ile Asp Ser
            815                 820                 825 act cgg gaa cca aat agc tct gca caa att gat att gtt atc tcc aac    2607
Thr Arg Glu Pro Asn Ser Ser Ala Gln Ile Asp Ile Val Ile Ser Asn
        830                 835                 840 aaa gcc gca gta gct ggg tta gat aaa gcg gaa aga gct ggt att ccc    2655
Lys Ala Ala Val Ala Gly Leu Asp Lys Ala Glu Arg Ala Gly Ile Pro
845                 850                 855 act aga gta att aat cat aaa ctg tat aaa aat cgt gta gaa ttt gac    2703
Thr Arg Val Ile Asn His Lys Leu Tyr Lys Asn Arg Val Glu Phe Asp
860                 865                 870                 875 agt gca att gac cta gtc ctt gaa gag ttc tcc ata gac ata gtc tgt    2751
Ser Ala Ile Asp Leu Val Leu Glu Glu Phe Ser Ile Asp Ile Val Cys
                880                 885                 890 ctt gca gga ttc atg aga att ctt tct ggc ccc ttt gtc caa aag tgg    2799
Leu Ala Gly Phe Met Arg Ile Leu Ser Gly Pro Phe Val Gln Lys Trp
            895                 900                 905 aat gga aaa atg ctc aat atc cac cca tcc ttg ctc cct tct ttt aag    2847
Asn Gly Lys Met Leu Asn Ile His Pro Ser Leu Leu Pro Ser Phe Lys
        910                 915                 920 ggt tca aat gcc cat gag caa gcc ctg gaa acc gga gtc aca gtt act    2895
Gly Ser Asn Ala His Glu Gln Ala Leu Glu Thr Gly Val Thr Val Thr
925                 930                 935 ggg tgc act gta cac ttt gta gct gaa gat gtg gat gct gga cag att    2943
Gly Cys Thr Val His Phe Val Ala Glu Asp Val Asp Ala Gly Gln Ile
940                 945                 950                 955 att ttg caa gaa gct gtt ccc gtg aag agg ggt gat act gtc gca act    2991
Ile Leu Gln Glu Ala Val Pro Val Lys Arg Gly Asp Thr Val Ala Thr
                960                 965                 970 ctt tct gaa aga gta aaa tta gca gaa cat aaa ata ttt cct gca gcc    3039
Leu Ser Glu Arg Val Lys Leu Ala Glu His Lys Ile Phe Pro Ala Ala
            975                 980                 985 ctt cag ctg gtg gcc agt gga act gta cag ctt gga gaa  aat ggc aag   3087
Leu Gln Leu Val Ala Ser Gly Thr Val Gln Leu Gly Glu  Asn Gly Lys
        990                 995                 1000 atc tgt tgg gtt aaa gag gaa  tga agccttttaa ttcagaaatg             3131
Ile Cys Trp Val Lys Glu Glu
    1005                1010 gggccagttt agaagaatt atttgctgtt tgcatggtgg tttttatca tggacttggc    3191 ccaaaagaaa aactgctaaa agacaaaaaa gacctcaccc ttacttcatc tattttttta  3251
ataaatagag actcactaaa aaaaaaaaaa aaaaaaaaa                         3291

<210> SEQ ID NO 18
<211> LENGTH: 1010
<212> TYPE: PRT
<213> ORGANISM: Homo sapiens
```

<400> SEQUENCE: 18

```
Met Ala Ala Arg Val Leu Ile Ile Gly Ser Gly Gly Arg Glu His Thr
1               5                   10                  15

Leu Ala Trp Lys Leu Ala Gln Ser His His Val Lys Gln Val Leu Val
            20                  25                  30

Ala Pro Gly Asn Ala Gly Thr Ala Cys Ser Glu Lys Ile Ser Asn Thr
        35                  40                  45

Ala Ile Ser Ile Ser Asp His Thr Ala Leu Ala Gln Phe Cys Lys Glu
    50                  55                  60

Lys Lys Ile Glu Phe Val Val Gly Pro Glu Ala Pro Leu Ala Ala
65                  70                  75                  80

Gly Ile Val Gly Asn Leu Arg Ser Ala Gly Val Gln Cys Phe Gly Pro
                85                  90                  95

Thr Ala Glu Ala Ala Gln Leu Glu Ser Ser Lys Arg Phe Ala Lys Glu
                100                 105                 110

Phe Met Asp Arg His Gly Ile Pro Thr Ala Gln Trp Lys Ala Phe Thr
            115                 120                 125

Lys Pro Glu Glu Ala Cys Ser Phe Ile Leu Ser Ala Asp Phe Pro Ala
130                 135                 140

Leu Val Val Lys Ala Ser Gly Leu Ala Ala Gly Lys Gly Val Ile Val
145                 150                 155                 160

Ala Lys Ser Lys Glu Glu Ala Cys Lys Ala Val Gln Glu Ile Met Gln
                165                 170                 175

Glu Lys Ala Phe Gly Ala Ala Gly Glu Thr Ile Val Ile Glu Glu Leu
            180                 185                 190

Leu Asp Gly Glu Glu Val Ser Cys Leu Cys Phe Thr Asp Gly Lys Thr
            195                 200                 205

Val Ala Pro Met Pro Pro Ala Gln Asp His Lys Arg Leu Leu Glu Gly
210                 215                 220

Asp Gly Gly Pro Asn Thr Gly Gly Met Gly Ala Tyr Cys Pro Ala Pro
225                 230                 235                 240

Gln Val Ser Asn Asp Leu Leu Leu Lys Ile Lys Asp Thr Val Leu Gln
                245                 250                 255

Arg Thr Val Asp Gly Met Gln Gln Glu Gly Thr Pro Tyr Thr Gly Ile
            260                 265                 270

Leu Tyr Ala Gly Ile Met Leu Thr Lys Asn Gly Pro Lys Val Leu Glu
        275                 280                 285

Phe Asn Cys Arg Phe Gly Asp Pro Glu Cys Gln Val Ile Leu Pro Leu
    290                 295                 300

Leu Lys Ser Asp Leu Tyr Glu Val Ile Gln Ser Thr Leu Asp Gly Leu
305                 310                 315                 320

Leu Cys Thr Ser Leu Pro Val Trp Leu Glu Asn His Thr Ala Leu Thr
                325                 330                 335

Val Val Met Ala Ser Lys Gly Tyr Pro Gly Asp Tyr Thr Lys Gly Val
            340                 345                 350

Glu Ile Thr Gly Phe Pro Glu Ala Gln Ala Leu Gly Leu Glu Val Phe
        355                 360                 365

His Ala Gly Thr Ala Leu Lys Asn Gly Lys Val Val Thr His Gly Gly
    370                 375                 380

Arg Val Leu Ala Val Thr Ala Ile Arg Glu Asn Leu Ile Ser Ala Leu
385                 390                 395                 400

Glu Glu Ala Lys Lys Gly Leu Ala Ala Ile Lys Phe Glu Gly Ala Ile
                405                 410                 415
```

```
Tyr Arg Lys Asp Val Gly Phe Arg Ala Ile Ala Phe Leu Gln Gln Pro
            420                 425                 430

Arg Ser Leu Thr Tyr Lys Glu Ser Gly Val Asp Ile Ala Ala Gly Asn
            435                 440                 445

Met Leu Val Lys Lys Ile Gln Pro Leu Ala Lys Ala Thr Ser Arg Ser
            450                 455                 460

Gly Cys Lys Val Asp Leu Gly Phe Ala Gly Leu Phe Asp Leu Lys
465                 470                 475                 480

Ala Ala Gly Phe Lys Asp Pro Leu Leu Ala Ser Gly Thr Asp Gly Val
                485                 490                 495

Gly Thr Lys Leu Lys Ile Ala Gln Leu Cys Asn Lys His Asp Thr Ile
            500                 505                 510

Gly Gln Asp Leu Val Ala Met Cys Val Asn Asp Ile Leu Ala Gln Gly
            515                 520                 525

Ala Glu Pro Leu Phe Phe Leu Asp Tyr Phe Ser Cys Gly Lys Leu Asp
            530                 535                 540

Leu Ser Val Thr Glu Ala Val Val Ala Gly Ile Ala Lys Ala Cys Gly
545                 550                 555                 560

Lys Ala Gly Cys Ala Leu Leu Gly Gly Glu Thr Ala Glu Met Pro Asp
                565                 570                 575

Met Tyr Pro Pro Gly Glu Tyr Asp Leu Ala Gly Phe Ala Val Gly Ala
            580                 585                 590

Met Glu Arg Asp Gln Lys Leu Pro His Leu Glu Arg Ile Thr Glu Gly
            595                 600                 605

Asp Val Val Gly Ile Ala Ser Ser Gly Leu His Ser Asn Gly Phe
610                 615                 620

Ser Leu Val Arg Lys Ile Val Ala Lys Ser Ser Leu Gln Tyr Ser Ser
625                 630                 635                 640

Pro Ala Pro Asp Gly Cys Gly Asp Gln Thr Leu Gly Asp Leu Leu Leu
                645                 650                 655

Thr Pro Thr Arg Ile Tyr Ser His Ser Leu Leu Pro Val Leu Arg Ser
            660                 665                 670

Gly His Val Lys Ala Phe Ala His Ile Thr Gly Gly Gly Leu Leu Glu
            675                 680                 685

Asn Ile Pro Arg Val Leu Pro Glu Lys Leu Gly Val Asp Leu Asp Ala
690                 695                 700

Gln Thr Trp Arg Ile Pro Arg Val Phe Ser Trp Leu Gln Gln Glu Gly
705                 710                 715                 720

His Leu Ser Glu Glu Glu Met Ala Arg Thr Phe Asn Cys Gly Val Gly
                725                 730                 735

Ala Val Leu Val Val Ser Lys Glu Gln Thr Glu Gln Ile Leu Arg Asp
            740                 745                 750

Ile Gln Gln His Lys Glu Glu Ala Trp Val Ile Gly Ser Val Val Ala
            755                 760                 765

Arg Ala Glu Gly Ser Pro Arg Val Lys Val Lys Asn Leu Ile Glu Ser
            770                 775                 780

Met Gln Ile Asn Gly Ser Val Leu Lys Asn Gly Ser Leu Thr Asn His
785                 790                 795                 800

Phe Ser Phe Glu Lys Lys Ala Arg Val Ala Val Leu Ile Ser Gly
                805                 810                 815

Thr Gly Ser Asn Leu Gln Ala Leu Ile Asp Ser Thr Arg Glu Pro Asn
            820                 825                 830

Ser Ser Ala Gln Ile Asp Ile Val Ile Ser Asn Lys Ala Ala Val Ala
            835                 840                 845
```

```
Gly Leu Asp Lys Ala Glu Arg Ala Gly Ile Pro Thr Arg Val Ile Asn
    850                 855                 860

His Lys Leu Tyr Lys Asn Arg Val Glu Phe Asp Ser Ala Ile Asp Leu
865                 870                 875                 880

Val Leu Glu Glu Phe Ser Ile Asp Ile Val Cys Leu Ala Gly Phe Met
                885                 890                 895

Arg Ile Leu Ser Gly Pro Phe Val Gln Lys Trp Asn Gly Lys Met Leu
                900                 905                 910

Asn Ile His Pro Ser Leu Leu Pro Ser Phe Lys Gly Ser Asn Ala His
            915                 920                 925

Glu Gln Ala Leu Glu Thr Gly Val Thr Val Thr Gly Cys Thr Val His
        930                 935                 940

Phe Val Ala Glu Asp Val Asp Ala Gly Gln Ile Ile Leu Gln Glu Ala
945                 950                 955                 960

Val Pro Val Lys Arg Gly Asp Thr Val Ala Thr Leu Ser Glu Arg Val
            965                 970                 975

Lys Leu Ala Glu His Lys Ile Phe Pro Ala Ala Leu Gln Leu Val Ala
                980                 985                 990

Ser Gly Thr Val Gln Leu Gly Glu Asn Gly Lys Ile Cys Trp Val Lys
        995                 1000                1005

Glu Glu
    1010
```

METHODS FOR ASSESSING CANCER FOR INCREASED SENSITIVITY TO 10-PROPARGYL-10-DEAZAAMINOPTERIN

RELATED APPLICATIONS

The instant application claims priority to and is a continuation in part of U.S. Ser. No. 12/637,254, filed Aug. Dec. 14, 2009, entitled "Methods to Treat Cancer with 10-Propargyl-10-Deazaaminopterin and Methods for Assessing Cancer for Increased Sensitivity to 10-Propargyl-10-Deazaaminopterin," which is now issued as U.S. Pat. No. 8,168,404, which is a continuation of U.S. Ser. No. 11/953,031, filed Dec. 8, 2007, entitled "Methods to Treat Cancer with 10-Propargyl-10-Deazaaminopterin and Methods for Assessing Cancer for Increased Sensitivity to 10-Propargyl-10-Deazaaminopterin," now abandoned, which is a continuation in part of U.S. Ser. No. 11/568,254, filed Feb. 20, 2007 now U.S. Pat. No. 7,939,530, entitled "Treatment Of Lymphoma Using 10-Propargyl-10-Deazaaminopterin And Gemcitabine," which claims priority to and is a national phase application of PCT/US2005/019170, now expired, filed May 31, 2005, entitled "Treatment Of Lymphoma Using 10-Propargyl-10-Deazaaminopterin And Gemcitabine," which in turn claims priority from U.S. Ser. No. 60/521,593, filed May 30, 2004, entitled "Method of Treating Lymphoma Using 10-Propargyl-10-Deazaaminopterin," each of which is incorporated herein in their entirety by reference for all that they teach and disclose.

TECHNICAL FIELD

The present invention relates to methods to treat cancer with 10-propargyl-10-deazaaminopterin and methods for assessing cancers and selecting patients for treatment based for increased sensitivity to 10-propargyl-10-deazaaminopterin.

SEQUENCE INCORPORATED BY REFERENCE

Incorporated by reference herein in its entirety is the Sequence Listing co-submitted with the instant application, entitled "MSK79_4.txt", created Jun. 14, 2010, size of 95 kilobytes.

BACKGROUND OF THE INVENTION

10-Propargyl-10-deazaaminopterin (encompassing "10-propargyl-10-dAM," "pralatrexate," "racemic PDX," "(2S)-2-[[4-[(1RS)-1-[(2,4-diaminopteridin-6-yl)methyl]but-3-ynyl]benzoyl]amino]pentanedioic acid," "(2RS)-2-[[4-[(1RS)-1-[(2,4-diaminopteridin-6-yl)methyl]but-3-ynyl]benzoyl]amino]pentanedioic acid," and "PDX"), is a compound which has been tested and found useful in the treatment of cancer. 10-propargyl-10-deazaaminopterin has been approved by the U.S. Food and Drug Administration (FDA) as a treatment for relapsed and refractory peripheral T-cell lymphoma. 10-propargyl-10-deazaaminopterin is also being investigated for use in lymphoma, lung cancer, bladder cancer, and breast cancer.

10-propargyl-10-deazaaminopterin was originally disclosed by DeGraw et al., "Synthesis and Antitumor Activity of 10-Propargyl-10-deazaaminopterin," J. Med. Chem. 36: 2228-2231 (1993).

U.S. Pat. No. 6,028,071 and PCT Publication No. WO 1998/02163, disclose that highly purified 10-propargyl-10-deazaaminopterin compositions when tested in a xenograft model have efficacy against human tumors. Subsequent studies with 10-propargyl-10-deazaaminopterin have shown that it is useful on its own and in combinations with other therapeutic agents. For example, Sirotnak et al., Clinical Cancer Research Vol. 6, 3705-3712 (2000) reports that co-administration of 10-propargyl-10-deazaaminopterin and probenecid, an inhibitor of a cMOAT/MRP-like plasma membrane ATPase, greatly enhances the efficacy of 10-propargyl-10-deazaaminopterin against human solid tumors. 10-propargyl-10-deazaaminopterin and combinations of 10-propargyl-10-deazaaminopterin with platinum based chemotherapeutic agents have been shown to be effective against mesothelioma. (Khokar, et al., Clin. Cancer Res. 7: 3199-3205 (2001). Co-administration with gemcitabine (Gem), for treatment of lymphoma, has been disclosed in WO/2005/117892. Combinations of 10-propargyl-10-deazaaminopterin with taxols are disclosed to be efficacious in U.S. Pat. No. 6,323,205. 10-propargyl-10-deazaaminopterin has also shown to be effective for treatment of T-cell lymphoma, see U.S. Pat. No. 7,622,470. Other studies have shown a method for assessing sensitivity of a lymphoma to treatment with 10-propargyl-10-deazaaminopterin by determining the amount of reduced folate carrier-1 protein (RFC-1) expressed by the sample, wherein a higher level of expressed RFC-1 is indicative of greater sensitivity to 10-propargyl-10-deazaaminopterin, disclosed in PCT Publication No. WO 2005/117892.

10-propargyl-10-deazaaminopterin is known as an antifolate/antimetabolite. Several proteins are implicated in the metabolism of folic acid and as targets of anti-folates such as 10-propargyl-10-deazaaminopterin and methotrexate (MTX) in tumor cells.

One of the continued problems with therapy in cancer patients is individual differences in response to therapies. While advances in development of successful cancer therapies progress, only a subset of patients respond to any particular therapy. With the narrow therapeutic index and the toxic potential of many available cancer therapies, such differential responses potentially contribute to patients undergoing unnecessary, ineffective and even potentially harmful therapy regimens. If a designed therapy could be optimized to treat individual patients, such situations could be reduced or even eliminated. Furthermore, targeted designed therapy may provide more focused, successful patient therapy overall. Accordingly, there is a need to identify particular cancer patients who are expected to have a favorable outcome when administered particular cancer therapies as well as particular cancer patients who may have a favorable outcome using more aggressive and/or alternative cancer therapies, e.g., alternative to previous cancer therapies administered to the patient. It would therefore be beneficial to provide for the diagnosis, staging, prognosis, and monitoring of cancer patients, including, e.g., hematological cancer patients (e.g., multiple myeloma, leukemias, lymphoma, etc.) who would benefit from particular cancer inhibition therapies as well as those who would benefit from a more aggressive and/or alternative cancer inhibition therapy, e.g., alternative to a cancer therapy or therapies the patient has received, thus resulting in appropriate preventative measures. Therefore, a need still exists in the art for improved methods to select patients for treatment with a particular therapeutic, among other needs.

SUMMARY OF THE INVENTION

The present invention relates to a method for assessing the sensitivity of a patient's cancer to treatment with 10-propargyl-10-deazaaminopterin and a method for selecting a patient for treatment of cancer with 10-propargyl-10-deazaaminopterin, by determining the amount of a selected polypeptide expressed by the cancer and comparing the amount with the amount of the selected polypeptide expressed by a reference cancer, wherein the polypeptide includes a member of folate pathway polypeptide within a cell and may include at least one of the following polypeptides: reduced folate carrier-1 enzyme (RFC-1), dihydrofolate reductase (DHFR), folylpoly-gamma-glutamate synthetase (FPGS), thymidylate synthase (TS), γ-glutamyl hydrolase (GGH), and glycinamide ribonucleotide formyltransferase (GARFT).

In one embodiment, the present invention includes a method of selecting a patient for treatment of a cancer with 10-propargyl-10-deazaaminopterin. The method can comprise the following steps, in any order. One step comprises obtaining a sample of the patient's cancer tissue; another step comprises determining the expression level of at least one polypeptide which includes a member of a folate pathway polypeptide within a cell and may include at least one of the following polypeptides: RFC-1, DHFR, FPGS, TS, GGH, and GARFT expressed in the sample; another step includes comparing the determined expression level in the sample with a reference expression level for a member of the folate pathway polypeptide within a cell; and another step includes selecting the patient for treatment 10-propargyl-10-deazaaminopterin where the comparison of the expression level in the sample of the member of the folate pathway polypeptide within the cell and the corresponding reference expression level indicate sensitivity of patient's cancer tissue to 10-propargyl-10-deazaaminopterin. In some embodiments, the patient's cancer is a solid tumor. In some embodiments, the solid tumor can be any of the following: NSCLC, head and neck cancer, prostate cancer, and breast cancer.

In another embodiment, the present invention includes a method for assessing sensitivity of a patient's cancer to treatment with 10-propargyl-10-deazaaminopterin. This method can include the following steps, in any order. One step includes obtaining a sample of the patient's cancer tissue. Another step includes determining the expression level of a polypeptide which may include a member of a folate pathway polypeptide within a cell and may include at least one of RFC-1, DHFR, FPGS, TS, GGH, and GARFT expressed in the sample. Another step includes comparing the determined expression level in the sample with a reference expression level for a member of a folate pathway polypeptide within a cell and to determine whether the expression level for the member of a folate pathway polypeptide within a cell and in the sample is indicative of an expression level that predicts sensitivity to 10-propargyl-10-deazaaminopterin. Another step includes generating a report of the predicted sensitivity of the sample to 10-propargyl-10-deazaaminopterin. In some embodiments, the patient's cancer is a solid tumor. In some embodiments, the solid tumor can be any of the following: NSCLC, head and neck cancer, prostate cancer, and breast cancer.

In another embodiment, the present invention includes a method for assessing sensitivity of a cancer to treatment with 10-propargyl-10-deazaaminopterin. This method includes the following steps, in any order. One step includes obtaining a sample of the lymphoma. Another step includes determining the amount of a member of a folate pathway polypeptide within a cell and expressed by the sample wherein higher levels of expression of a member of a folate pathway polypeptide within a cell and are indicative of sensitivity to 10-propargyl-10-deazaaminopterin; and generating a report of the predicted sensitivity of the sample to 10-propargyl-10-deazaaminopterin.

DETAILED DESCRIPTION OF THE INVENTION

Figure 1:
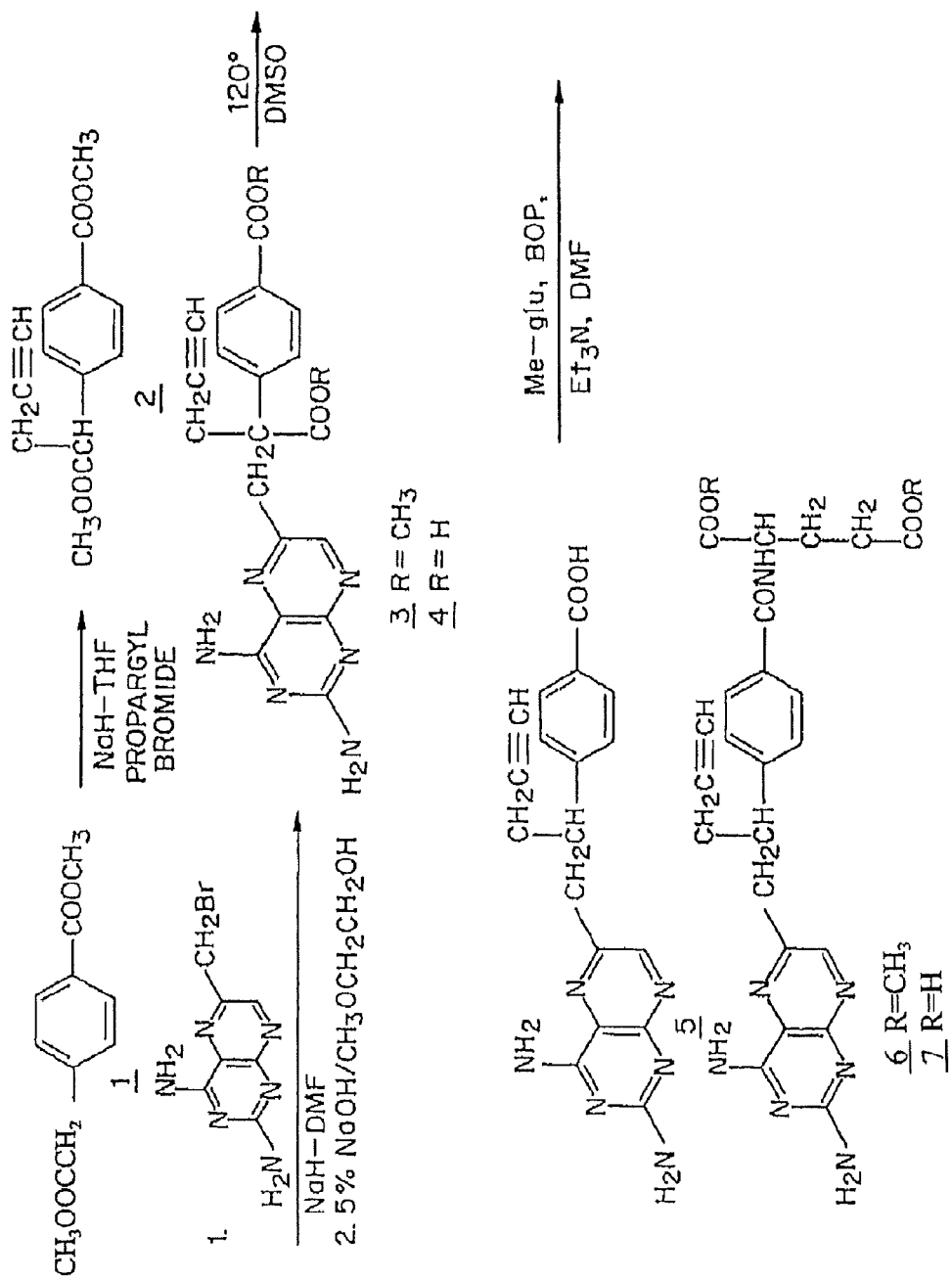
FIG. 1 shows a synthetic scheme useful in preparing 10-propargyl-10-deazaaminopterin.

One of the continued problems with therapy in cancer patients is individual differences in response to therapies. While advances in development of successful cancer therapies progress, only a subset of patients respond to any particular therapy. With the narrow therapeutic index and the toxic potential of many available cancer therapies, such differential responses potentially contribute to patients undergoing unnecessary, ineffective and even potentially harmful therapy regimens. If a designed therapy could be optimized to treat individual patients, such situations could be reduced or even eliminated. Furthermore, targeted designed therapy may provide more focused, successful patient therapy overall. Accordingly, there is a need to identify particular cancer patients who are expected to have a favorable outcome when administered particular cancer therapies as well as particular cancer patients who may have a favorable outcome using more aggressive and/or alternative cancer therapies, e.g., alternative to previous cancer therapies administered to the patient. It would therefore be beneficial to provide for the diagnosis, staging, prognosis, and monitoring of cancer patients, including, e.g., hematological cancer patients (e.g., multiple myeloma, leukemias, lymphoma, etc.) who would benefit from particular cancer inhibition therapies as well as those who would benefit from a more aggressive and/or alternative cancer inhibition therapy, e.g., alternative to a cancer therapy or therapies the patient has received, thus resulting in appropriate preventative measures.

A cancer is "responsive" to a therapeutic agent or there is a "good response" to a treatment if its rate of growth is inhibited as a result of contact with the therapeutic agent, compared to its growth in the absence of contact with the therapeutic agent. Growth of a cancer can be measured in a variety of ways, for instance, the size of a tumor or the expression of tumor markers appropriate for that tumor type may be measured. These criteria define the type of response measured and also the characterization of time to disease progression which is another important measure of a tumor's sensitivity to a therapeutic agent. The quality of being responsive 10-propargyl-10-deazaaminopterin is a variable one, with different cancers exhibiting different levels of "responsiveness" to a given therapeutic agent, under different conditions. Still further, measures of responsiveness can be assessed using additional criteria beyond growth size of a tumor, including patient quality of life, degree of metastases, etc. In addition, clinical prognostic markers and variables can be assessed in applicable situations.

A cancer is "non-responsive" or has a "poor response" to a therapeutic agent such as 10-propargyl-10-deazaaminopterin or there is a poor response to a treatment if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor, including patient quality of life, degree of metastases, etc. In addition, clinical prognostic markers and variables can be assessed in applicable situations.

In most tumor cells, RFC-1 mediates internalization of folate analogs. Once inside the cell, these analogs either bind dihydrofolate reductase (DHFR), thereby depleting intracellular reduced folate pools needed for purine and thymidine biosynthesis, or will be metabolized to a polyglutamates prior to binding to DHFR. Polyglutamylation is catalyzed by folylpolyglutamate synthetase (FPGS). Folyl-poly glutamate hydrolase (FPGH, also known as gamma-glutamyl hydrolase [GGH]) mediates cleavage and thus subsequent clearance of these intracellular polyglutamated anti-folates. Thymidylate synthase (TS) and glycinamide ribonucleotide formyl transferase (GARFT) are also involved in folate metabolism as "recycling" enzymes (thus directly affecting pools of nucleotides available for DNA synthesis). Without intending to be bound by a specific mechanism, it is believed that the correlation between RFC-1 expression levels and 10-propargyl-10-deazaaminopterin sensitivity is a reflection of increased transport of 10-propargyl-10-deazaaminopterin into tumor cells. Without being bound by theory, it is believed that alterations in other folate pathway polypeptides discussed herein also correlate with 10-propargyl-10-deazaaminopterin sensitivity; such as, for example, reduced DHFR levels correlating with a decrease in the amount of intracellular drug required to inhibit this enzyme, reduced GARFT and TS potentially reducing the pools of available nucleotides, increased FPGS increasing the rate of polyglutamylation of 10-propargyl-10-deazaaminopterin and resulting in increased retention within the cell to facilitate ongoing activity against DHFR.

In one aspect, the present invention relates to a method for assessing the sensitivity of a patient's cancer to treatment with 10-propargyl-10-deazaaminopterin and a method for selecting a patient for treatment of cancer with 10-propargyl-10-deazaaminopterin, by determining the amount of a polypeptide which may include a member of a folate pathway polypeptide within a cell and may include at least one of RFC-1, DHFR, FPGS, TS, GGH, and GARFT expressed by the cancer and comparing the amount with the amount of the folate pathway polypeptide expressed by a reference cancer. Sensitivity to 10-propargyl-10-deazaaminopterin is indicated when the amounts of the folate pathway polypeptide are comparable to, or greater than, or less than, or in an amount that is otherwise indicative of sensitivity, compared to the amount in a reference cancer, as discussed more fully below. The reference cancer can include a cancer that is sensitive to 10-propargyl-10-deazaaminopterin.

"Treatment" can mean the use of a therapy to prevent or inhibit further tumor growth, as well as to cause shrinkage of a tumor, and to provide longer survival times. Treatment is also intended to include prevention of metastasis of tumor. A tumor is "inhibited" or "treated" if at least one symptom (as determined by responsiveness/non-responsiveness, time to progression, or indicators known in the art and described herein) of the cancer or tumor is alleviated, terminated, slowed, minimized, or prevented. Any amelioration of any symptom, physical or otherwise, of a tumor pursuant to treatment using a therapeutic regimen (e.g., 10-propargyl-10-deazaaminopterin) as further described herein, is within the scope of the invention.

A folate pathway polypeptide of the present invention can include a folate pathway polypeptide within a cell and may include at least one of RFC-1, DHFR, FPGS, TS, GGH, and GARFT. In one embodiment, the folate pathway polypeptide is RFC-1. In another, it is DHFR. In another, it is FPGS.

In one embodiment of the invention, the composition used for the methods of the instant invention can include 10-propargyl-10-deazaaminopterin, including "highly purified" 10-propargyl-10-deazaaminopterin, and diastereomers of 10-propargyl-10-deazaaminopterin. As used in the specification and claims hereof, compositions which are "highly purified" contain 10-propargyl-10-deazaaminopterin substantially free of other folic acid derivatives, particularly 10-deazaaminopterin, which can interfere with the antitumor activity of the 10-propargyl-10-deazaaminopterin. A composition within the scope of the invention may include carriers or excipients for formulating the 10-propargyl-10-deazaaminopterin into a suitable dosage unit form for therapeutic use, as well as additional, non-folate therapeutic agents.

10-propargyl-10-deazaaminopterin contains asymmetric centers at the carbon 10 (C10) and carbon 19 (C19) position. In one embodiment, 10-propargyl-10-deazaaminopterin includes an approximately 1:1 racemic mixture of the R- and S-configurations at the C10 chiral center, and ≧98.0% of the S-diastereomer at the C19 chiral center. 10-propargyl-10-deazaaminopterin includes the C10 diastereomers PDX-10a [S-configuration] Chemical name (2S)-2-[[4-[(1S)-1-[(2,4-diaminopteridin-6-yl)methyl]but-3-ynyl]benzoyl]amino]pentanedioic acid, a PDX-10b [R-configuration] Chemical name: (2S)-2-[[4-[(1R)-1-[(2,4-diaminopteridin-6-yl)methyl]but-3-ynyl]benzoyl]amino]pentanedioic acid.

10-propargyl-10-deazaaminopterin can be synthesized using the method disclosed in Example 7 of DeGraw et al., U.S. Pat. No. 5,354,751, which is directed to manufacturing 10-propargyl-10-deazaaminopterin, is incorporated by reference herein in its entirety. 10-propargyl-10-deazaaminopterin may also be synthesized by methods presented in U.S. Pat. No. 6,028,071, especially in Example 1, which example is incorporated by reference herein.

In order to generate diastereomers of 10-propargyl-10-deazaaminopterin, 10-propargyl-10-deazaaminopterin may be synthesized as taught herein and elsewhere, and either the final product or an earlier intermediate product may be subsequently used as a starting material to separate the C10 diastereomers. Alternately, a chiral synthesis may be employed where substantially pure PDX-10a and/or PDX-10b is produced directly from any of a number of starting materials. Chiral columns to separate enantiomers or diastereomers, known in the art, may be employed to separate the diastereomers of the final 10-propargyl-10-deazaaminopterin or an earlier intermediate. Suitable chiral columns for separating the diastereomers include the chiral column CHIRAL-PAK AD, available from Daicel Chemical Industries Ltd., Japan, using ethanol as the mobile phase.

10-propargyl-10-deazaaminopterin for use in a 10-propargyl-10-deazaaminopterin-sensitive cancer according to the present invention will typically be administered to the patient in a dose regimen that provides for the most effective treatment (from both efficacy and safety perspectives) for which the patient is being treated, as known in the art. In conducting the treatment method of the present invention, the 10-propargyl-10-deazaaminopterin for use in a 10-propargyl-10-deazaaminopterin-sensitive cancer according to the present invention can be administered in any effective manner known in the art, such as by oral, topical, intravenous, intra-peritoneal, intramuscular, intra-articular, subcutaneous, intranasal, intra-ocular, vaginal, rectal, intracranial, or intradermal routes, depending upon the type of cancer being treated, and the medical judgment of the prescribing physician as based, e.g., on the results of published clinical studies.

10-propargyl-10-deazaaminopterin for use in a 10-propargyl-10-deazaaminopterin-sensitive cancer according to the present invention can be formulated as part of a pharmaceutical preparation. The specific dosage form will depend on the method of administration, but may include tablets, capsules, oral liquids, and injectable solutions for oral, intravenous, intramuscular, intracranial, or intraperitoneal administration, and the like. Dosing may be expressed as mg/m$^2$. Alternatively, dosing may be expressed as mg/kg body weight by any manner acceptable to one skilled in the art. One method for obtaining an equivalent dosing in mg/kg body weight involves applying the conversion factor 0.025 mg/kg, for an average human, as approximately equivalent to 1 mg/m$^2$. According to this calculation, dosing of 150 mg/m$^2$ is approximately equivalent to about 3.75 mg/kg.

Appropriate dosing for oncology for treatment of a 10-propargyl-10-deazaaminopterin-sensitive cancer includes the following dosage regimes. For example, doses on the order of 10 to 120 mg/m$^2$ of body surface area/day (about 0.25 to 3 mg/kg body weight per day) are appropriate. Dosages of 30 mg/m$^2$ (about 0.75 mg/kg) once weekly for 3 weeks followed by a one week rest, 30 mg/m$^2$ (about 0.75 mg/kg) once weekly×6 weeks followed by a one week rest, or gradually increasing doses of 10-propargyl-10-deazaaminopterin on the once weekly×6 week schedule are also suitable. Lower doses may be used as appropriate based on patient tolerance and type of malignancy. Higher doses can be utilized where less frequent administration is used. Thus, in a general sense, dosages of 10 to 275 mg/m$^2$ (about 0.25 to about 6.9 mg/kg) are suitably used with various dosing schedules, for example between about 100 to 275 mg/m$^2$ (about 2.5 to about 6.87 mg/kg) for biweekly dosages, and between about 10 to 150 mg/m$^2$ (about 0.25 to about 3.75 mg/kg), or, more specifically, between about 10 and 60 mg/m$^2$ for once weekly dosages.

The determination of suitable dosages using protocols similar to those described in U.S. Pat. No. 6,323,205 is within the skill in the art. In one embodiment, 10-propargyl-10-deazaaminopterin for use in a 10-propargyl-10-deazaaminopterin-sensitive cancer according to the present invention can be administered in an amount of from about 10 to about 275 mg/m$^2$ (about 0.25 to about 6.87 mg/kg) per dose. Methods of the present invention also include administration of 10-propargyl-10-deazaaminopterin for use in a 10-propargyl-10-deazaaminopterin-sensitive cancer according to the present invention weekly; in a dose of about 10 mg/m$^2$ (0.25 mg/kg) or about 30 mg/m$^2$ (0.75 mg/kg); in an amount of from about 10 to about 150 mg/m$^2$ (about 0.25 to about 3.75 mg/kg) per dose; biweekly; and in a dosage amount of about 100 to about 275 mg/m$^2$ (about 2.5 to about 6.9 mg/kg). In one embodiment, 10-propargyl-10-deazaaminopterin for use in a 10-propargyl-10-deazaaminopterin-sensitive cancer according to the present invention can be administered in an amount of between about 0.25 mg/kg and about 4 mg/kg; between about 0.75 mg/kg and about 3 mg/kg; in an amount between about 1.0 mg/kg and about 2.5 mg/kg; in an amount of about 0.25 mg/kg or about 0.75 mg/kg (or an equivalent amount in body surface area (BSA)).

10-propargyl-10-deazaaminopterin may be used in combinations with other cytotoxic and antitumor compounds, including vinca alkaloids such as vinblastine, navelbine, and vindesine; probenicid, nucleotide analogs such as gemcitabine, 5-fluorouracil, and cytarabine; alkylating agents such as cyclophosphamide or ifosfamide; cisplatin or carboplatin; leucovorin; taxanes such a paclitaxel or docetaxel; anti-CD20 monoclonal antibodies, with or without radioisotopes, and antibiotics such as doxorubicin and mitomycin. Combinations of 10-propargyl-10-deazaaminopterin with several of these other antitumor agents or with growth factor inhibitors and anti-angiogenic agents may also be used.

10-propargyl-10-deazaaminopterin and other agents may be concurrently administered or utilized in combination as part of a common treatment regimen, in which the 10-propargyl-10-deazaaminopterin and the other agent(s) are administered at different times. For example, the other agent may be administered before, immediately afterward or after a period of time (for example 24 hours) relative to the 10-propargyl-10-deazaaminopterin administration. Thus, for purposes of this application, the term administering refers generally to concurrent administration or to sequential administration of the drugs and in either order in a parallel treatment regimen with or without a separation in time between the drugs unless otherwise specified.

10-propargyl-10-deazaaminopterin is suitably used in combination with folic acid and vitamin B 12 supplementation to reduce the side effects of the treatment. For example, patients may be treated with folic acid (1 mg/m$^2$ daily starting 1 week prior to treatment with 10-propargyl-10-deazaaminopterin, or alternatively 1 mg perioral (p.o.) daily not based on body surface area (BSA)); and B12 (1 mg/m$^2$ monthly, or alternatively given intramuscularly (I.M.) every 8-10 weeks as 1 mg (not based on BSA), or alternatively p.o. daily 1 mg (not based on BSA)).

In one embodiment of the present invention, the invention includes a method for selecting a patient for treatment of a cancer with 10-propargyl-10-deazaaminopterin, the method including the following steps (in any order.) One step includes obtaining a sample of the patient's cancer tissue. Another step includes determining the expression level of a folate pathway polypeptide within a cell and may include at least one of RFC-1, DHFR, FPGS, TS, GGH, and GARFT. Another step includes comparing the determined expression level in the sample with a reference expression level for the folate pathway polypeptide. In another step, the instant method includes selecting the patient for treatment with 10-propargyl-10-deazaaminopterin, where the comparison of the expression level in the sample of the folate pathway polypeptide, and the corresponding reference expression level of the same, indicates or predicts sensitivity to 10-propargyl-10-deazaaminopterin.

In another embodiment, the present invention includes a method for assessing the sensitivity of a patient's cancer to treatment with 10-propargyl-10-deazaaminopterin. This method includes the following steps, in any order. One step includes obtaining a sample of the patient's cancer tissue. Another step includes determining the amount of a folate pathway polypeptide, expressed by the sample. Another step optionally includes obtaining a reference expression level for the folate pathway polypeptide, for a cancer having sensitivity to 10-propargyl-10-deazaaminopterin. The sample cancer and the reference cancer may be the same or different. Another step includes comparing the determined expression level in the sample with a reference expression level for the folate pathway polypeptide, to determine whether the expression level for the folate pathway polypeptide in the sample is a match to, is similar to, is greater than, is less than, or is otherwise indicative of an expression level that predicts sensitivity to 10-propargyl-10-deazaaminopterin. Another optional step includes the step of generating a report of predicted sensitivity of the sample to 10-propargyl-10-deazaaminopterin.

In one embodiment of the invention, an expression level of a folate pathway polypeptide that predicts sensitivity to 10-propargyl-10-deazaaminopterin is one that "matches," or is similar to, is greater than, is less than, or is in an amount that otherwise indicates sensitivity, the level of the folate pathway polypeptide of a 10-propargyl-10-deazaaminopterin-sensitive cancer. The cancer type for the reference may be the same or different than the cancer type for the sample, but in one embodiment is the same type of cancer.

In one embodiment, a "match," or a level that is similar to, is greater than, is less than, or in an amount that otherwise indicates sensitivity of the sample expression level of a folate pathway polypeptide indicates the patient's cancer has increased sensitivity to 10-propargyl-10-deazaaminopterin.

Another step includes generating a report of the sensitivity of the sample to 10-propargyl-10-deazaaminopterin. A report may be, without limitation, an oral report, a printed report, or an electronically transmitted report.

A folate pathway polypeptide, which includes RFC-1, FPGS, and DHFR, is also variously referred to herein as a "biomarker of the invention," "biomarker," "marker," "peptide," "selected peptide," or a plural thereof, and the like.

In another embodiment of the present invention, a method of selecting a patient for treatment of a cancer with 10-propargyl-10-deazaaminopterin is provided. The method includes the following steps, in any order. One step includes obtaining a sample of the patient's cancer tissue. Another step includes determining the amount of at least one folate pathway polypeptide or its mRNA expressed by the sample. Another optional step includes obtaining a reference expression level for the at least folate pathway polypeptide or its mRNA for a cancer having sensitivity to 10-propargyl-10-deazaaminopterin. Another step includes comparing the expression data for the folate pathway polypeptide or its mRNA with the reference expression for the same folate pathway polypeptide.

In some steps of the methods of the present invention, the level of expression of the RNA and/or protein products of one or more folate pathway polypeptides of the invention, as measured by the amount or level of RNA or protein, is compared to see if the level of expression is similar to, a match to, or if the sample has significantly greater expression than the reference, or the respective levels is otherwise indicative of sensitivity, to a person of skill in the art. The term "match" indicates that the level of expression of protein or mRNA, and/or one or more spliced variants of mRNA of the biomarker in the sample is compared with the level of expression of the same one or more biomarkers of the invention as measured by the amount or level of protein, or level of RNA, including mRNA and/or one or more spliced variants of mRNA in a reference sample, and is determined to be similar to, a match to, or the sample has significantly greater expression than the reference, or the respective levels are otherwise indicative of sensitivity, to a person of skill in the art and/or in accordance with the discussion herein below.

Determining if the sample is similar to, a match to, a reference, or the sample has significantly greater or lesser expression than the reference, or the respective levels are otherwise indicative of sensitivity, to a person of skill in the art, can also include a measurement of the protein, or one or more protein variants encoded by a folate pathway polypeptide of the invention in the sample as compared with the amount or level of protein expression, including one or more protein variants of the same folate pathway polypeptide of the invention in the reference sample.

Similarity to, a match to, or wherein the sample has significantly greater or less expression than the reference, or the respective levels is otherwise indicative of sensitivity, to a person of skill in the art includes a level of expression (mRNA or protein) in the sample that is less than about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 98%, at least about 100%, at least about 110%, at least about 120%, at least about 130%, at least about 140%, at least about 150%, at least about 160%, at least about 170%, at least about 180%, at least about 200%, at least about three fold, at least about four fold, at least about five fold, at least about ten-fold, of the reference.

In some embodiments, similarity to, or a match with, the reference level is an amount of the folate pathway polypeptide or its mRNA in the sample is an amount that is significantly greater or less than the amount of the folate pathway polypeptide or its mRNA in the reference. In those embodiments, the amount of the selected folate pathway polypeptide or its mRNA may be significantly enhanced or decreased over the reference expression level, such as, ten-fold greater or less, twenty-fold greater or less, fifty-fold greater or lesser, one hundred-fold greater or lesser, or more.

A "normal" amount of a marker may refer to the amount of a "reference sample", (e.g., sample from a healthy subject not having the marker-associated disease), preferably, the average expression level of the marker in several healthy subjects. A reference sample amount may be comprised of an amount of one or more markers from a reference database. Alternatively, a "normal" level of expression of a marker is the amount of the biomarker, in non-tumor cells in a similar environment or response situation from the same patient that the tumor is derived from. The normal amount of DNA copy number is 2 or diploid.

Increased or decreased amount of a biomarker of the invention may refer to cancer- or tumor-specific "over-expression" and "under-expression" of a biomarker, and may indicate that the biomarker of a particular tumor or cancer in a patient is present at a greater or lesser level, respectively, than normal level of expression of the biomarker (e.g. more than three-halves-fold, at least two-fold, at least three-fold, greater or lesser level etc.) in a test sample that is greater than the standard error of the assay employed to assess expression. For example, a decreased level of a particular biomarker in a cancer or tumor, compared to normal tumors or cancers, or resistant tumors or cancers, may be associated with increased sensitivity to 10-propargyl-10-deazaaminopterin. Accordingly, if a patient's cancer or tumor shows decreased levels of expression of that particular biomarker, such a cancer or tumor would be predicted to demonstrate sensitivity to 10-propargyl-10-deazaaminopterin and would be a good candidate for treatment with 10-propargyl-10-deazaaminopterin. Or, for example, an increased level of expression of a particular biomarker in a cancer or tumor, compared to normal tumors or cancers, or resistant tumors or cancers, may be associated with increased sensitivity to 10-propargyl-10-deazaaminopterin. Accordingly, if a patient's cancer or tumor shows increased levels of expression of that particular biomarker, such a cancer or tumor would be predicted to demonstrate sensitivity to 10-propargyl-10-deazaaminopterin and would be a good candidate for treatment with 10-propargyl-10-deazaaminopterin. A "significant" expression level may refer to level which either meets or is above or below a pre-determined score for a biomarker set as determined by methods provided herein.

In one embodiment, the general form of a prediction rule consists in the specification of a function of one biomarker potentially including clinical covariates to predict response or non-response, or more generally, predict benefit or lack of benefit in terms of suitably defined clinical endpoints.

The simplest form of a prediction rule consists of a univariate model without covariates, where the prediction is determined by means of a cutoff or threshold. Such a model is utilized in one embodiment in the present invention. This can be phrased in terms of the Heaviside function for a specific cutoff c and a biomarker measurement x, where the binary prediction A or B is to be made, then If $H(x-c)=0$ then predict A.
If $H(x-c)=1$ then predict B.

This is the simplest way of using univariate biomarker measurements in prediction rules. If such a simple rule is sufficient, it allows for a simple identification of the direction of the effect, i.e. whether high or low expression levels are beneficial for the patient.

The situation can be more complicated if clinical covariates need to be considered and/or if multiple biomarkers are used in multivariate prediction rules. For example, for a biomarker X it may be determined in a clinical trial population that high expression levels are associated with a better prognosis (univariate analysis). A closer analysis shows that there are two tumor types in the population, one of which possess a worse prognosis than the other one and at the same time the biomarker expression for this tumor group is generally lower.

As used herein, the terms "protein" and "polypeptide" and "proteinaceous agent" are used interchangeably to refer to a chain of amino acids linked together by peptide bonds which optionally can comprise natural or non-natural amino acids. Optionally, the protein or peptide can comprise other molecules in addition to amino acids. Said chain can be of any length. Polypeptides of the present invention include polypeptides related to folate pathways in cells including the selected polypeptides, including wherein the polypeptide includes a folate pathway polypeptide. Polypeptides of the present invention include polypeptides related to folate pathways in cells including the selected polypeptides associated with the pathway, including reduced folate carrier-1 enzyme (RFC-1), dihydrofolate reductase (DHFR), thymidylate synthase (TS), γ-glutamyl hydrolase (GGH) (also known as folypolyglutamate hydrolase (FPGH)), folylpoly-gamma-glutamate synthetase (FPGS), and glycinamide ribonucleotide formyltransferase (GARFT). The accession numbers and SEQ ID NOs of the selected polypeptides are as follows:

| Polypeptide | Full name | GenBank Accession Number | SEQ ID NOs |
|---|---|---|---|
| DHFR | dihydrofolate reductase | NM_000791 | 4, 5, 6 |
| FPGS | folylpolyglutamate synthetase | M98045 | 13, 14, 15 |
| GARFT | glycinamide ribonucleotide transformylase | X54199 | 16, 17, 18 |
| GGH | gamma-glutamyl hydrolase | NM_003878 | 10, 11, 12 |
| RFC-1 | reduced folate carrier, member 1 | NM_194255.1 | 1, 2, 3 |
| TS | Thymidylate synthase | NM_001071 | 7, 8, 9 |

As used herein, nucleotide sequences of the gene products of the above identified selected polypeptides include, but are not limited to, the cDNA, genome-derived DNA and synthetic or semi-synthetic DNA or RNA.

The term "polynucleotide" is used to mean a polymeric form of nucleotides of any length, which contain deoxyribonucleotides, ribonucleotides, and/or their analogs. The terms "polynucleotide" and "nucleotide" as used herein are used interchangeably. Polynucleotides can have any three-dimensional structure, and can perform any function, known or unknown. The term "polynucleotide" includes double-stranded, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide can be comprised of modified nucleotides, such as methylated nucleotides and nucleotide analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentynyluracil and 2,6-diaminopurine. The use of uracil as a substitute for thymine in a deoxyribonucleic acid is also considered an analogous form of pyrimidine.

A "fragment" (also called a "region") of a polynucleotide (i.e., a polynucleotide encoding a SNP) is a polynucleotide comprised of at least 9 contiguous nucleotides of the novel genes. Preferred fragments are comprised of a region encoding at least 5 contiguous amino acid residues, more preferably, at least 10 contiguous amino acid residues, and even more preferably at least 15 contiguous amino acid residues.

The term "recombinant" polynucleotide as used herein intends a polynucleotide of genomic, cDNA, semisynthetic, or synthetic in origin which, by virtue of its origin or manipulation: is not associated with all or a portion of a polynucleotide with which it is associated in nature; is linked to a polynucleotide other than that to which it is linked in nature; or does not occur in nature.

As used herein, reference to a selected gene product, protein or polypeptide in the present invention, including a folate pathway polypeptide, includes full-length proteins, fusion proteins, or any fragment or homologue of such a protein. The amino acid sequence for a folate pathway polypeptide from human are described herein as exemplary folate pathway-associated polypeptides and proteins. In addition, and by way of example, a "human a folate pathway polypeptide" refers to a folate pathway polypeptide (generally including a homologue of a naturally occurring a folate pathway polypeptide) from a human (Homo sapiens) or to a folate pathway polypeptide that has been otherwise produced from the knowledge of the structure (e.g., sequence) and perhaps the function of a naturally occurring folate pathway polypeptide from Homo sapiens. In other words, a folate pathway polypeptide includes any folate pathway polypeptide that has substantially similar structure and function of a naturally occurring folate pathway polypeptide from Homo sapiens or that is a biologically active (i.e., has biological activity) homologue of a naturally occurring folate pathway polypeptide from Homo sapiens as described in detail herein. As such, a human folate pathway polypeptide can include purified, partially purified, recombinant, mutated/modified and synthetic proteins. According to the present invention, the terms "modification" and "mutation" can be used interchangeably, particularly with regard to the modifications/mutations to the amino acid sequence of a folate pathway polypeptide (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

According to the present invention, an isolated folate pathway polypeptide, including a biologically active homologue or fragment thereof, has at least one characteristic of biological activity of activity a wild-type, or naturally occurring folate pathway polypeptide (which can vary depending on whether the homologue or fragment is an agonist, antagonist, or mimic of folate pathway polypeptide, and the isoform folate pathway polypeptide).

Homologues of a folate pathway polypeptide, including peptide and non-peptide agonists and antagonists of a folate pathway polypeptide (analogues), can be products of drug design or selection and can be produced using various methods known in the art. Such homologues can be referred to as mimetics.

In one embodiment, a folate pathway polypeptide homologue comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to a naturally occurring a folate pathway polypeptide amino acid sequence. A homologue of a folate pathway polypeptide differs from a reference (e.g., wild-type) a folate pathway polypeptide and therefore is less than 100% identical to the reference a folate pathway polypeptide at the amino acid level.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schaaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art. In general, the design and selection of primers embodied by the instant invention is according to methods that are standard and well known in the art, see Dieffenbach, C. W., Lowe, T. M. J., Dveksler, G. S. (1995) General Concepts for PCR Primer Design. In: PCR Primer, A Laboratory Manual (Eds. Dieffenbach, C. W, and Dveksler, G. S.) Cold Spring Harbor Laboratory Press, New York, 133-155; Innis, M. A., and Gelfand, D. H. (1990) Optimization of PCRs. In: PCR protocols, A Guide to Methods and Applications (Eds. Innis, M. A., Gelfand, D. H., Sninsky, J. J., and White, T. J.) Academic Press, San Diego, 3-12; Sharrocks, A. D. (1994) The design of primers for PCR. In: PCR Technology, Current Innovations (Eds. Griffin, H. G., and Griffin, A. M, Ed.) CRC Press, London, 5-11.

As used herein, the terms "RNA portion" and "a portion thereof" in context of RNA products of a biomarker of the invention refer to an RNA transcript comprising a nucleic acid sequence of at least 6, at least 9, at least 15, at least 18, at least 21, at least 24, at least 30, at least 60, at least 90, at least 99, or at least 108, or more nucleotides of a RNA product of a biomarker of the invention.

Obtaining a sample of the patient's cancer tissue may be done by any methods known in the art. Bone marrow or lymph node biopsies and analysis of peripheral blood samples for cytogenetic and/or immunologic analysis is standard practice. Frozen tissue specimens may be obtained as well. As used herein a "sample" can be from any organism and can further include, but is not limited to, peripheral blood, plasma, urine, saliva, gastric secretion, feces, bone marrow specimens, primary tumors, metastatic tissue, embedded tissue sections, frozen tissue sections, cell preparations, cytological preparations, exfoliate samples (e.g., sputum), fine needle aspirations, amino cells, fresh tissue, dry tissue, and cultured cells or tissue. It is further contemplated that the biological sample of this invention can also be whole cells or cell organelles (e.g., nuclei). The sample can be unfixed or fixed according to standard protocols widely available in the art.

In some embodiments of the present invention, peripheral blood is drawn, or alternatively, if desired, leukocytes may be isolated by differential gradient separation, using, for example, ficoll-hypaque or sucrose gradient solutions for cell separations, followed by ammonium chloride or hypotonic lysis of remaining contaminating erythrocytes ("Cell Biology: A Laboratory Handbook", Volumes I-III Cellis, J. E., ed. (1994); "Current Protocols in Immunology" Volumes I-III Coligan J. E., ed. (1994); Stites et al. (eds)). Bone marrow and lymph node biopsies may be processed by collagenase/dispase treatment of the biopsy material, or by homogenization in order to obtain single cell suspensions ("Cell Biology: A Laboratory Handbook", Volumes I-III Cellis, J. E., ed. (1994); "Current Protocols in Immunology" Volumes I-III Coligan J. E., ed. (1994); Stites et al. (eds)).

The sample can be from a subject or a patient. As utilized herein, the "subject" or "patient" of the methods described herein can be any animal. In a preferred embodiment, the animal of the present invention is a human. In addition, determination of expression patterns is also contemplated for non-human animals which can include, but are not limited to, cats, dogs, birds, horses, cows, goats, sheep, guinea pigs, hamsters, gerbils, mice and rabbits.

The term "cancer," when used herein refers to or describes the pathological condition, preferably in a mammalian subject, that is typically characterized by unregulated cell growth. Non-limiting cancer types include carcinoma (e.g., adenocarcinoma), sarcoma, myeloma, leukemia, and lymphoma, and mixed types of cancers, such as adenosquamous carcinoma, mixed mesodermal tumor, carcinosarcoma, and teratocarcinoma.

In one embodiment, cancers include solid tumors, in particular, non-small cell lung cancer, head and neck cancer, prostate cancer, and breast cancer. Other cancers include but are not limited to, bladder cancer, lung cancer, colon cancer, rectal cancer, endometrial cancer, ovarian cancer; and melanoma. Specifically included are AIDS-related cancers (e.g., Kaposi's Sarcoma, AIDS-related lymphoma), bone cancers (e.g., osteosarcoma, malignant fibrous histiocytoma of bone, Ewing's Sarcoma, and related cancers), and hematologic/blood cancers (e.g., adult acute lymphoblastic leukemia, childhood acute lymphoblastic leukemia, adult acute myeloid leukemia, childhood acute myeloid leukemia, chronic lymphocytic leukemia, chronic myelogenous leukemia, hairy cell leukemia, adult Hodgkin's disease, childhood Hodgkin's disease, Hodgkin's disease during pregnancy, adult non-Hodgkin's lymphoma, childhood non-Hodgkin's lymphoma, non-Hodgkin's lymphoma during pregnancy, primary central nervous system lymphoma, Waldenstrom's macroglobulinemia, multiple myeloma/plasma cell neoplasm, myelodysplastic syndrome, and myeloproliferative disorders), as well as lymphoblastic lymphomas in which the malignancy occurs in primitive lymphoid progenitors from the thymus; mature or peripheral T-cell neoplasms, including T-cell prolymphocytic leukemia, T-cell granular lymphocytic leukemia, aggressive NK-cell leukemia, cutaneous T-cell lymphoma (Mycosis fungoides/Sezary syndrome), anaplastic large cell lymphoma, T-cell type, enteropathy-type T-cell lymphoma, Adult T-cell leukemia/lymphoma including those associated with HTLV-1, and angioimmunoblastic T-cell lymphoma, and subcutaneous panniculitic T-cell lymphoma; and peripheral T-cell lymphomas that initially involve a lymph node paracortex and never grow into a true follicular pattern.

Also included are brain cancers (e.g., adult brain tumor, childhood brain stem glioma, childhood cerebellar astrocytoma, childhood cerebral astrocytoma, childhood ependymoma, childhood medulloblastoma, supratentorial primitive neuroectodermal and pineal, and childhood visual pathway and hypothalamic glioma), digestive/gastrointestinal cancers (e.g., anal cancer, extrahepatic bile duct cancer, gastrointestinal carcinoid tumor, colon cancer, esophageal cancer, gallbladder cancer, adult primary liver cancer, childhood liver cancer, pancreatic cancer, rectal cancer, small intestine cancer, and gastric cancer), musculoskeletal cancers (e.g., childhood rhabdomyosarcoma, adult soft tissue sarcoma, childhood soft tissue sarcoma, and uterine sarcoma), and endocrine cancers (e.g., adrenocortical carcinoma, gastrointestinal carcinoid tumor, islet cell carcinoma (endocrine pancreas), parathyroid cancer, pheochromocytoma, pituitary tumor, and thyroid cancer).

Also included are neurologic cancers (e.g., neuroblastoma, pituitary tumor, and primary central nervous system lymphoma), eye cancers (e.g., intraocular melanoma and retinoblastoma), genitourinary cancers (e.g., bladder cancer, kidney (renal cell) cancer, penile cancer, transitional cell renal pelvis and ureter cancer, testicular cancer, urethral cancer, Wilms' tumor and other childhood kidney tumors), respiratory/thoracic cancers (e.g., non-small cell lung cancer, small cell lung cancer, malignant mesothelioma, and malignant thymoma), germ cell cancers (e.g., childhood extracranial germ cell tumor and extragonadal germ cell tumor), skin cancers (e.g., melanoma, and merkel cell carcinoma), gynecologic cancers (e.g., cervical cancer, endometrial cancer, gestational trophoblastic tumor, ovarian epithelial cancer, ovarian germ cell tumor, ovarian low malignant potential tumor, uterine sarcoma, vaginal cancer, and vulvar cancer), and unknown primary cancers.

In one embodiment, the sample and the reference cancer are both the same cancer sub-type, i.e., the sample cancer is derived from the same type of cell as the reference cancer. In another embodiment, the reference cancer is any one of or a combination of a cancer or cancerous cell line derived from a solid tumor, in particular, non-small cell lung cancer, head and neck cancer, prostate cancer, and breast cancer, T-cell lymphoma or a multiple myeloma, such as, for example, lymphoblastic lymphomas in which the malignancy occurs in primitive lymphoid progenitors from the thymus; mature or peripheral T-cell neoplasms, including T-cell prolymphocytic leukemia, T-cell granular lymphocytic leukemia, aggressive NK-cell leukemia, cutaneous T-cell lymphoma (Mycosis fungoides/Sezary syndrome), anaplastic large cell lymphoma, T-cell type, enteropathy-type T-cell lymphoma, Adult T-cell leukemia/lymphoma including those associated with HTLV-1, and angioimmunoblastic T-cell lymphoma, and subcutaneous panniculitic T-cell lymphoma; and peripheral T-cell lymphomas that initially involve a lymph node paracortex. As used in the specification and claims of this application, the term "lymphomas" refers to Non-Hodgkins Lymphoma (NHL); diffuse large B-cell lymphoma (DLBCL); follicular lymphoma (FL); Hodgkin's Disease; Burkitt's Lymphoma; cutaneous T-cell lymphoma; primary central nervous system lymphoma, and lymphomatous metastases. In one embodiment of the present invention, this application relates to the use of 10-propargyl-10-deazaaminopterin in the treatment of T-cell lymphoma.

In another embodiment of the present invention, the reference cancer or cancerous cell line is a reference cancer or cancerous cell line which is known to have a greater sensitivity to 10-propargyl-10-deazaaminopterin. The term, "greater sensitivity," includes those cancers that are known or are found to have an enhanced response to 10-propargyl-10-deazaaminopterin as compared to methotrexate ("MTX.") Increased sensitivity may be determined by those of skill in the art and may include assessment of effects seen in cell lines derived from that cancer and/or type of cancer, in animal models, such as mouse subcutaneous transplantation models, and therapeutic indicators such as remission or other indicia of reduced tumor burden in patients, such as increased apoptosis, decreased tumor volume, growth inhibition, and other indicia known to those in the art. An enhanced response can include differential effects seen at equivalent doses of, serum concentrations of, or other indicia of equivalence between, MTX and 10-propargyl-10-deazaaminopterin.

The selected polypeptides may be quantitated and/or relative amounts determined by any method known in the art for quantitating and/or deteimining relative amounts of expression levels. The term, "quantitate" or "quantitation" also includes determination of relative amounts of a polypeptide or its transcript. Quantitating transcript RNA or portions thereof of a selected polypeptide is one such method. RNA may be extracted from biological samples via a number of standard techniques (see Current Protocols in Molecular Biology" Volumes I-III Ausubel, R. M., ed. (1994); Ausubel et al., "Current Protocols in Molecular Biology", John Wiley and Sons, Baltimore, Md. (1989)). Guanidium-based methods for cell lysis enabling RNA isolation, with subsequent cesium chloride step gradients for separation of the RNA from other cellular macromolecules, followed by RNA precipitation and resuspension, is an older, less commonly employed method of RNA isolation (Glisin, Ve. et al (1973) *Biochemistry* 13: 2633). Alternatively, RNA may be isolated in a single step procedure (U.S. Pat. No. 4,843,155, and Puissant, C. and Houdebine L. M. (1990) *Biotechniques* 8: 148-149). Single step procedures include the use of Guanidium isothiocyanate for RNA extraction, and subsequent phenol/chloroform/isoamyl alcohol extractions facilitating the separation of total RNA from other cellular proteins and DNA. Commercially available single-step formulations based on the above-cited principles may be employed, including, for example, the use of the TRIZOL reagent (Life Technologies, Gaithersburg, Md.).

According to further features of preferred embodiments of the present invention, monitoring selected polypeptide RNA/gene expression is via a number of standard techniques well described in the art, any of which can be employed to evaluate selected polypeptide expression. These assays comprise Northern blot and dot blot analysis, primer extension, RNase protection, RT-PCR, in-situ hybridization and chip hybridization. Specific selected polypeptide RNA sequences can be readily detected by hybridization of labeled probes to blotted RNA preparations extracted as above. In Northern blot analysis, fractionated RNA is subjected to denaturing agarose gel electrophoresis, which prevents RNA from assuming secondary structures that might inhibit size based separation. RNA is then transferred by capillary transfer to a nylon or nitrocellulose membrane support and may be probed with a labeled oligonucleotide probe complementary to the selected polypeptide sequence (Alwine, et al. (1977). Proc. Natl. Acad. Sci. USA 74: 5350-5354 and Current Protocols in Molecular Biology" Volumes I-III Ausubel, R. M., ed. (1994); Ausubel et al., "Current Protocols in Molecular Biology", John Wiley and Sons, Baltimore, Md. (1989)).

Alternatively, unfractionated RNA may be immobilized on a nylon or nitrocellulose membrane, and similarly probed for selected polypeptide-specific expression, by Slot/Dot blot analysis. RNA slot/dot blots can be prepared by hand, or alternatively constructed using a manifold apparatus, which facilitates comparing hybridization signals by densitometry scanning (Chomczynski P. (1992) Anal. Biochem. 201: 134-139). Primer extension is an additional means whereby quantification of the RNA may be accomplished. Primer extension provides an additional benefit in mapping the 5' terminus of a particular RNA, by extending a primer using the enzyme reverse transcriptase. In this case, the primer is an oligonucleotide (or restriction fragment) complementary to a portion of the selected polypeptide mRNA. The primer is end-labeled, and is allowed to hybridize to template selected polypeptide mRNA. Once hybridized, the primer is extended by addition of reverse transcriptase, and incorporation of unlabeled dexoynucleotides to for a single-stranded DNA complementary to template selected polypeptide mRNA. DNA is then analyzed on a sequencing gel, with the length of extended primer serving to map the 5' position of the mRNA, and the yield of extended product reflecting the abundance of RNA in the sample (Jones et al (1985) Cell 42: 559-572 and Mierendorf R. C. And Pfeffer, D. (1987). Methods Enzymol. 152: 563-566).

RNase protection assays provide a highly sensitive means of quantifying selected polypeptide RNA, even in low abundance. In protection assays, sequence-specific hybridization of ribonucleotide probes complementary to selected polypeptide RNA, with high specific activity are generated, and hybridized to sample RNA. Hybridization reactions are then treated with ribonuclease to remove free probe, leaving intact fragments of annealed probe hybridized to homologous selected polypeptide sequences in sample RNA. Fragments are then analyzed by electrophoresis on a sequencing gel, when appropriately-sized probe fragments are visualized (Zinn K. et al (1983) Cell 34: 865-879 and Melton S. A., et al (1984). Nucl. Acids Res. 12: 7035-7056).

RT-PCR is another means by which selected polypeptide expression is verified. RT-PCR is a particularly useful method for detecting rare transcripts, or transcripts in low abundance. RT-PCR employs the use of the enzyme reverse transcriptase to prepare cDNA from RNA samples, using deoxynucleotide primers complementary to the selected polypeptide mRNA. Once the cDNA is generated, it is amplified through the polymerase chain reaction, by the addition of dexoynucleotides and a DNA polymerase that functions at high temperatures. Through repetitive cycles of primer annealing, incorporation of dexoynucleotides facilitating cDNA extension, followed by strand denaturation, amplification of the desired sequence occurs, yielding an appropriately sized fragment that may be detected by agarose gel electrophoresis. Alternatively, the RT-PCR reaction can be quantified in real-time using techniques known to those skilled in the art. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y.).

In-situ hybridization provides another tool for the detection and localization of cell/tissue specific selected polypeptide RNA expression. Labeled anti-sense RNA probes are hybridized to mRNAs in cells singly, or in processed tissue slices, which are immobilized on microscope glass slides (In Situ Hybridization: Medical Applications (eds. G. R. Coulton and J. de Belleroche), Kluwer Academic Publishers, Boston (1992); In Situ Hybridization: In Neurobiology; Advances in Methodology (eds. J. H. Eberwine, K. L. Valentino, and J. D. Barchas), Oxford University Press Inc., England (1994); and In Situ Hybridization: A Practical Approach (ed. D. G. Wilkinson), Oxford University Press Inc., England (1992)). Numerous non-isotopic systems have been developed to visualize labeled DNA probes including; a) fluorescence-based direct detection methods, b) the use of digoxigenin- and biotin-labeled DNA probes coupled with fluorescence detection methods, and c) the use of digoxigenin- and biotin-labeled DNA probes coupled with antibody-enzyme detection methods. When fluorescence-labeled anti-sense RNA probes are hybridized to cellular RNA, the hybridized probes can be viewed directly using a fluorescence microscope. Direct fluorochrome-labeling of the nucleic acid probes eliminate the need for multi-layer detection procedures (e.g., antibody-based-systems), which allows fast processing and also reduces non-specific background signals, hence providing a versatile and highly sensitive means of identifying selected polypeptide gene expression.

Chip hybridization utilizes selected polypeptide-specific oligonucleotides attached to a solid substrate, which may consist of a particulate solid phase such as nylon filters, glass slides or silicon chips [Schena et al. (1995) Science 270:467-470] designed as a microarray. Microarrays are known in the art and consist of a surface to which probes that correspond in sequence to gene products (such as cDNAs) can be specifically hybridized or bound at a known position for the detection of selected polypeptide gene expression. Quantification of the hybridization complexes is well known in the art and may be achieved by any one of several approaches. These approaches are generally based on the detection of a label or marker, such as any radioactive, fluorescent, biological or enzymatic tags or labels of standard use in the art. A label can be applied to either the oligonucleotide probes or the RNA derived from the biological sample.

In general, mRNA quantification is preferably effected alongside a calibration curve so as to enable accurate mRNA determination. Furthermore, quantifying transcript(s) originating from a biological sample is preferably effected by comparison to a normal sample, which sample is characterized by normal expression pattern of the examined transcript(s).

Selected polypeptide expression may also be evaluated at the level of protein expression, either by demonstration of the presence of the protein, or by its activity, with activity herein referring to the enzymatic activity of the selected polypeptide enzyme. Methods for monitoring specific polypeptide protein expression include but are not limited to the following methods discussed below. Anti-folate pathway polypeptide selected polypeptide-antibodies for use in selected polypeptide-specific protein detection are readily generated by methods known in the art and include both polyclonal and monoclonal antibodies. The antibodies preferably bind to both native and denatured selected polypeptides and may be detected by several well-known assays in the art, including ELISA, RIA, light emission immunoassays, Western blot analysis, immunofluorescence assays, immunohistochemistry and FACS analysis.

Enzyme linked immunosorbant (ELISA) assays and radio-immunoassays (RIA) follow similar principles for detection of specific antigens, in this case, selected polypeptides. In RIA a selected polypeptide-specific antibody is radioactively labeled, typically with $^{125}$I. In ELISA assays a selected polypeptide-specific antibody is chemically linked to an enzyme. Selected polypeptide-specific capturing antibody is immobilized onto a solid support. Unlabelled specimens, e.g., protein extracts from biopsy or blood samples are then incubated with the immobilized antibody under conditions where non-specific binding is blocked, and unbound antibody and/or protein removed by washing. Bound selected polypeptide is detected by a second selected polypeptide-specific labeled antibody. Antibody binding is measured directly in RIA by measuring radioactivity, while in ELISA binding is detected by a reaction converting a colorless substrate into a colored reaction product, as a function of linked-enzyme activity. Changes can thus readily be detected by spectrophotometry (Janeway C. A. et al (1997). "Immunbiology" 3rd Edition, Current Biology Ltd., Garland Publishing Inc.; "Cell Biology: A Laboratory Handbook", Volumes I-III Cellis, J. E., ed. (1994); "Current Protocols in Immunology" Volumes I-III Coligan J. E., ed. (1994); Stites et al. (eds)). Both assays therefore provide a means of quantification of selected polypeptide protein content in a biological sample.

Selected polypeptide protein expression may also be detected via light emission immunoassays. Much like ELISA and RIA, in light emission immunoassays the biological sample/protein extract to be tested is immobilized on a solid support, and probed with a specific label, labeled anti-selected polypeptide antibody. The label, in turn, is luminescent, and emits light upon binding, as an indication of specific recognition. Luminescent labels include substances that emit light upon activation by electromagnetic radiation, electro chemical excitation, or chemical activation and may include fluorescent and phosphorescent substances, scintillators, and chemiluminescent substances. The label can be a part of a catalytic reaction system such as enzymes, enzyme fragments, enzyme substrates, enzyme inhibitors, coenzymes, or catalysts; part of a chromogen system such as fluorophores, dyes, chemiluminescers, luminescers, or sensitizers; a dispersible particle that can be non-magnetic or magnetic, a solid support, a liposome, a ligand, a receptor, a hapten radioactive isotope, and so forth (U.S. Pat. No. 6,410,696, U.S. Pat. No. 4,652,533 and European Patent Application No. 0,345,776), and provide an additional, highly sensitive method for detection of selected polypeptide protein expression.

Western blot analysis is another means of assessing selected polypeptide content in a biological sample. Protein extracts from biological samples of, for example, hematopoietic cells, are solubilized in a denaturing ionizing environment, and aliquots are applied to polyacrylamide gel matrixes. Proteins separate based on molecular size properties as they migrate toward the anode. Antigens are then transferred to nitrocellulose, PVDF or nylon membranes, followed by membrane blocking to minimize non-specific binding. Membranes are probed with antibodies directly coupled to a detectable moiety, or are subsequently probed with a secondary antibody containing the detectable moiety. Typically the enzymes horseradish peroxidase or alkaline phosphatase are coupled to the antibodies, and chromogenic or luminescent substrates are used to visualize activity (Harlow E. et al (1998) Immunoblotting. In Antibodies: A Laboratory Manual, pp. 471-510 CSH Laboratory, cold Spring Harbor, N.Y. and Bronstein I. Et al. (1992) Biotechniques 12: 748-753). Unlike RIA, ELISA, light emission immunoassays and immunblotting, which quantify selected polypeptide content in whole samples, immunofluorescence/immunocytochemistry may be used to detect proteins in a cell-specific manner, though quantification is compromised.

In another embodiment, the present invention includes a method to modulate the expression of a folate pathway polypeptide in a patient's cancer comprising administering to a patient an effective amount of 10-propargyl-10-deazaaminopterin. In one embodiment, the patient's cancer is a solid tumor, in particular, non-small cell lung cancer, head and neck cancer, prostate cancer, and breast cancer, or a lymphoma; in one embodiment, the patient's cancer is a T-cell lymphoma; in another embodiment, the patient's cancer is NSCLC. The modulation can occur in vitro and/or in vivo. Modulation includes both up-regulation and down-regulation. As used herein, the term "up regulated" or "increased level of expression" in the context of this invention refers to a sequence corresponding to a folate pathway polypeptide which is expressed wherein the measure of the quantity of the sequence demonstrates an increased level of expression of the gene in the patient as compared to prior to administration of 10-propargyl-10-deazaaminopterin, and can be observed at any point in treatment with 10-propargyl-10-deazaaminopterin. An "increased level of expression" according to the present invention, is an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. "Down regulation" or "decreased level of expression" in the context of this invention refers to a sequence corresponding to a gene which is expressed wherein the measure of the quantity of the sequence demonstrates a decreased level of expression of the gene in the patient as compared to prior to administration of 10-propargyl-10-deazaaminopterin, and can be observed at any point in treatment with 10-propargyl-10-deazaaminopterin. A "decreased level of expression" according to the present invention, is a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. In one embodiment, the 10-propargyl-10-deazaaminopterin is substantially free of 10-deazaaminopterin.

In one embodiment, kits are provided for measuring a RNA product of a folate pathway polypeptide which comprise materials and reagents that are necessary for measuring the expression of the RNA product. For example, a microarray or RT-PCR kit may be used and contain only those reagents and materials necessary for measuring the levels of RNA products of any number of up to at least 1, at least 2, at least 3, at least 4, at least 5, at least 6, all or any combination of the folate pathway polypeptides. Alternatively, in some embodiments, the kits can comprise materials and reagents that are not limited to those required to measure the levels of RNA products of any number of up to 1, 2, 3, 4, 5, 6, all or any combination of the folate pathway polypeptides. For example, a microarray kit may contain reagents and materials necessary for measuring the levels of RNA products any number of up to 1, 2, 3, 4, 5, 6, all or any combination of the folate pathway polypeptide s, in addition to reagents and materials necessary for measuring the levels of the RNA products of any number of up to at least 1, at least 2, at least 3, at least 4, at least 5, at least 6, or more genes other than the folate pathway polypeptides. In a specific embodiment, a microarray or RT-PCR kit contains reagents and materials necessary for measuring the levels of RNA products of any number of up to at least 1, at least 2, at least 3, at least 4, at least 5, at least 6, all or any combination of the folate pathway polypeptides, and any number of up to 1, 2, 3, 4, 5, 10 or more genes that are not folate pathway polypeptides.

For nucleic acid microarray kits, the kits generally comprise probes attached to a support surface. The probes may be labeled with a detectable label. In a specific embodiment, the probes are specific for the 5' region, the 3' region, the internal coding region, an exon(s), an intron(s), an exon junction(s), or an exon-intron junction(s), of any number of up to 1, 2, 3, 4, 5, 6, all or any combination of the folate pathway polypeptides. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For RT-PCR kits, the kits generally comprise pre-selected primers specific for particular RNA products (e.g., an exon(s), an intron(s), an exon junction(s), and an exon-intron junction(s)) of any number of up to 1, 2, 3, 4, 5, 6, all or any combination of folate pathway polypeptides. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for any number of up to 1, 2, 3, 4, 5, 6, all or any combination of the folate pathway polypeptides. The probes may or may not be labeled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the perfoimance of the assay.

For antibody based kits, the kit can comprise, for example: (1) a first antibody (which may or may not be attached to a support) which binds to protein of interest (e.g., a protein product of any number of up to 1, 2, 3, 4, 5, 6, all or any combination of the folate pathway polypeptides); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

The following examples are provided for illustrative purposes only and are not intended to limit the scope of the invention.

Example 1

FIG. 1 shows a synthetic scheme useful in preparing 10-propargyl-10-deazaaminopterin. A mixture of 60% NaH in oil dispersion (1.06 g, 26.5 mmol) in 18 mL of sieve-dried THF was cooled to 0° C. The cold mixture was treated with a solution of homoterephthalic acid dimethyl ester (5.0 g, 24 mmol. compound 1 in FIG. 1) in dry THF (7 mL), and the mixture was stirred for 1 hour at 0° C. Propargyl bromide (26.4 mmol) was added, and the mixture was stirred at 0° C. for an additional 1 hour, and then at room temperature for 16 hours. The resulting mixture was treated with 2.4 mL of 50% acetic acid and then poured into 240 mL of water. The mixture was extracted with ether (2×150 mL). The ether extracts were combined, dried over $Na_2SO_4$, and concentrated to an orange-yellow oil. Chromatography on silica gel (600 mL of 230-400 mesh) with elution by cyclohexane-EtOAc (8:1) gave the product α-propargylhomoterephthalic acid dimethyl ester (compound 2) as a white solid (4.66) which appeared by TLC (cyclohexane-EtOAc, 3:1) to be homogeneous. Mass spectral data on this product, however, showed it to be a mixture of the desired product 2, and the di-propargylated compound. No starting material 1 was detected. HPLC shows the ratio of mono- to di-propargylated products to be about 3:1. Since the dipropargylated product, unlike compound 1, cannot produce an unwanted coproduct in the next step of the reaction, this material was suitable for conversion to compound 3. Absence of starting compound 1 in the product used to proceed in the synthesis is very important in order to avoid the sequential formation of 10-dAM during the transformations lading to the final product, because complete removal from 10-dAM from 10-propargyl-10-deazaaminopterin is very difficult.

A mixture was formed by combining 0.36 g of a 60% NaH (9 mmol) in oil dispersion with 10 mL of dry DMF and cooled to 0-5° C. The cold mixture was treated drop-wise with a solution of the product of the first reaction (compound 2) (2.94 g, 12 mmol) in 10 mL dry DMF and then stirred at 0° C. for 30 minutes. After cooling to −25° C., a solution of 2,4, diamino-6-(bromomethyl)-pteridine hydrobromide-0.2 2-propanol (1.00 g, 2.9 mmol) in 10 mL dry DMF was added drop-wise while the temperature was maintained near −25° C. The temperature of the stirred mixture was allowed to rise to −10° C. over a period of 2 hours. After an additional 2 hours at −10° C., the temperature was allowed to rise to 20° C., stirring at room temperature was continued for 2 hours longer. The reaction was then adjusted to pH 7 by addition of solid $CO_2$, After concentration in vacuo to remove solvent, the residue was stirred with diethyl ether and the ether insoluble material was collected, washed with water, and dried in vacuo to give 1.49 g of a crude product. This crude product was dissolved in $CHCl_3$-MeOH (10:1) for application to a silica gel column. Elution by the same solvent system afforded 10-propargyl-10-carbomethoxy-4-deoxy-4-a-mino-10-deazapteroic acid methyl ester (compound 3) which was homogenous to TLC in 40% yield (485 mg).

A stirred suspension of compound 3 (400 mg, 0.95 mmol) in 2-methoxyethanol (5 mL) was treated with water (5 mL) and then 10% sodium hydroxide solution (3.9 mL). The mixture was stirred as room temperature for 4 hours, during which time solution occurred. The solution was adjusted to pH 8 with acetic acid and concentrated under high vacuum. The resulting residue was dissolved in 15 mL of water and acidified to pH 5.5-5.8 resulting in formation of a precipitate. The precipitate was collected, washed with water and dried in vacuo to recover 340 mg of compound 4 (91% yield). HPLC analysis indicated a product purity of 90%.

Compound 4 (330 mg) was decarboxylated by heating in 15 mL DMSO at 115-120° C. for 10 minutes. A test by HPLC after 10 minutes confirmed that the conversion was essentially complete. DMSO was removed by distillation in vacuo (bath at 40° C.). The residue was stirred with 0.5 N NaOH to give a clear solution, Acidification to pH 5.0 with 1N HCl gave 10-propargyl-4-deoxy-4-amino-10-deazapteroic acid (compound 5) as a yellow solid in 70% yield. HPLC indicated product purity at this stage as 90%.

Compound 5 (225 mg, 0.65 mmol) was coupled with dimethyl L-glutamate hydrochloride (137 mg, 0.65 mmol) using BOP reagent (benzotriazole-1-yloxytris(dimethylamino) phosphonium hexafluorophosphate (287 mg, 0.65 mmol, Aldrich Chemical Co.) in DMF (10 mL) containing triethylamine (148 mg, 1.46 mmol). The mixture was stirred for 3 hours at 20-25° C. and then evaporated to dryness. The residue was stirred with water, and the water-insoluble crude product was collected and dried in vacuo. The crude product (350 mg) was purified by silica gel chromatography with elution by $CHCl_3$-MeOH (10:1) containing triethylamine (0.25% by volume) to recover 165 mg of 10-propargyl-10-deazaaminopterin dimethyl ester (compound 6, 50% yield) which was homogeneous to TLC ($CHCl_3$-MeOH 5:1).

Compound 6 (165 mg, 0.326 mmol) was suspended in 10 mL stirred MeOH to which 0.72 mL (0.72 meq) 1N NaOH was added. Stirring at room temperature was continued until solution occurred after a few hours. The solution was kept at 20-25°. for 8 hours, then diluted with 10 mL water. Evaporation under reduced pressure removed the methanol, and the concentrated aqueous solution was left at 20-25° C. for another 24 hours. HPLC then showed the ester hydrolysis to be complete. The clear aqueous solution was acidified with acetic acid to pH 4.0 to precipitate 10-propargyl-10-deazaaminopterin as a pale yellow solid, The collected, water washed and dried in vacuo product weighed 122 mg (79% yield). Assay by elemental analysis, proton NMR and mass spectroscopy were entirely consistent with the assigned structure. HPLC analysis indicated purity of 98% and established the product to be free of 10-deazaaminopterin.

In this case, the amount of 10-propargyl-10-deazaaminopterin (as determined by HPLC peak area) approaches 98%, and the peak corresponding to 10-deazaaminopterin is not detected by the processing software although there is a minor baseline ripple in this area.

Example 2

To explore the activity of pralatrexate across different solid tumor types, 15 human solid tumor cell lines were investigated for their sensitivity to the cytotoxic activity of pralatrexate.

Materials and Methods: Cell Lines

A panel of colon (HT29, HCT116, COLO205, HCC2998), breast (MCF7, MDA-MB-435), lung (HOP62, HOP92), ovarian (OVCAR3, IGROV1), prostate (DU145, PC3), and head and neck (SCC61, HEP2, SQ20B) human cancer cell lines was purchased from the ATCC (Rockville, Md.) and National Cancer Institute collections. Cells were grown as monolayers in RPMI medium supplemented with 10% fetal calf serum, 2 mM glutamine, 100 units $ml^{-1}$ penicillin and 100 μM $ml^{-1}$ streptomycin.

Cell Cytotoxicity Assays

All the data generated was the result of three separate experiments performed in duplicate. Cell viability was determined using the MTT assay, which was carried out as described previously (Hansen, 1989). Briefly, cells were seeded in 96-well plates at a density of $2 \times 10^3$ cells $well^{-1}$. Cells were incubated for 120 hours and then 0.4 mg $ml^{-1}$ of MTT dye (3-[4,5-dimethylthiazol-2-yl]-2,5-diphenyltetrazolium bromide was added for 4 hours at 37° C. The monolayer was suspended in 0.1 ml of DMSO and the absorbance at 560 nm was measured using a microplate reader. Positive and negative controls included wells with untreated cells or medium containing MTT with no cells, respectively. The conversion of yellow water-soluble tetrazolium MTT into purple insoluble formazan is catalyzed by mitochondrial dehydrogenases and is used to estimate the number of viable cells. The control value corresponding to untreated cells was taken as 100% and the viability of treated samples was expressed as a percentage of the control. $IC_{50}$ values were determined as concentrations that reduced cell viability by 50%.

For single agent studies, cells were seeded and allowed to settle for 24 hours prior to treatment with increasing concentrations of 10-propargyl-10-deazaaminopterin for 72 h. After incubation, the cells were allowed to recover in compound-free medium for 48 h, prior to determination of growth inhibition using the MTT assay.

Figure 2:
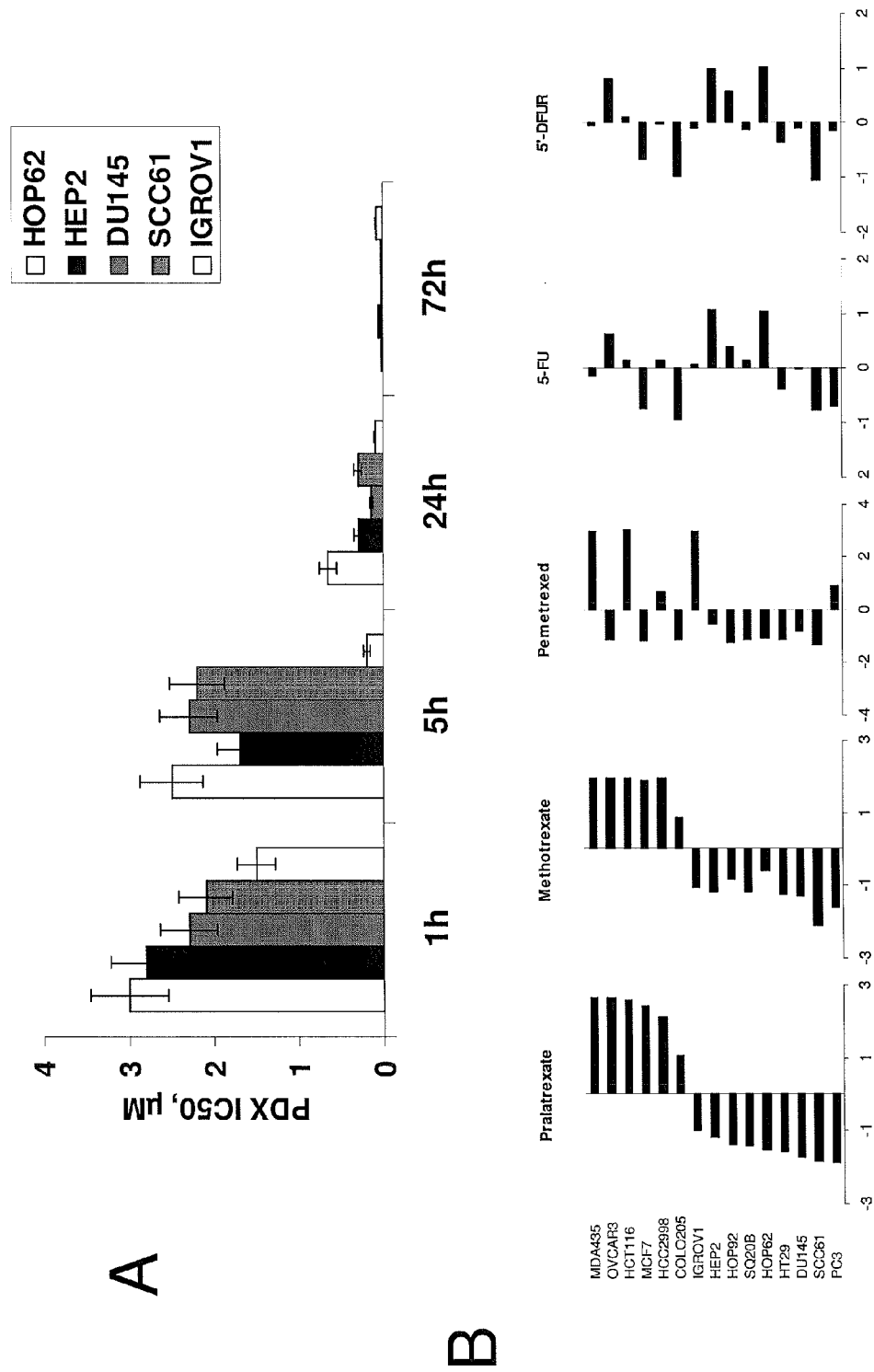
FIGS. 2A and B show sensitivity of 10-propargyl-10-deazaaminopterin and other folate inhibitors to 15 cancer cell lines tested; A: 10-propargyl-10-deazaaminopterin and methotrexate time-course ($IC_{50}$s, 1, 5, 24 and 72 hour drug exposure) cytotoxicity in sensitive cell lines. B—Comparative analysis of 72 h cytotoxicity of 10-propargyl-10-deazaaminopterin, methotrexate, pemetrexed, 5-FU and 5'-DFUR in a panel of cancer cell lines. The indicated values are calculated as follows: log ($IC_{50}$ individual cell line)–mean (log $IC_{50}$). Negative values indicate that the cell line is more sensitive than the average, where as positive values indicate that the cell line is more resistant than the average.

FIG. 2B shows the relative sensitivity to pralatrexate of the 15 human cancer cell lines tested. Nine of the cell lines were found to be sensitive to the cytotoxic activity of pralatrexate ($IC_{50} < 0.1$ μM), whereas 6 of the cell lines were found to be relatively resistant ($IC_{50} > 9$ μM). Concentrations of pralatrexate required to achieve an $IC_{50}$ ranged from $0.01 \pm 0.002$ μM for the prostate cancer cell line PC3 to $350 \pm 78$ μM for the MDA-MB-435 cell line. Interestingly, two groups of cell lines with more than 100-fold difference in $IC_{50}$ were observed: One group including PC3, SCC61, DU145, HT29, HOP62, SQ20B, HOP92, HEP2, and IGROV1 cells displayed $IC_{50} < 0.1$ μM while another group including Colo205, HCC2998, MCF7, HCT116, OVCAR3, and MDA-MB-435 cells showed $IC_{50}$ values higher than 9 μM.

Example 3

In order to establish potential correlations of pralatrexate sensitivity and resistance with expression of genes involved in apoptosis, cell cycle regulation and folate pathway signaling, mRNA expression of genes of interest were analyzed using real-time polymerase chain reaction (RT-PCR).

RT-PCR.

The theoretical and practical aspects of quantitative RT-PCR using the ABI Prism 7900 Sequence Detection System (Perkin-Elmer Applied Biosystems, Foster City, Calif., USA) are known to those skilled in the art. Results were expressed as n-fold differences in target gene expression relative to the TBP gene (an endogenous RNA control) and relative to a calibrator (1× sample), consisting of the cell line sample from the tested series that contained the smallest amount of target gene mRNA. Experiments were performed in duplicate.

The antiproliferative effects of pralatrexate were compared to those of methotrexate and several commonly used antimetabolites such as pemetrexed, 5-FU, and 5'-DFUR, the active capecitabine metabolite. Results are shown in FIG. 2B. Pralatrexate displayed cytotoxic effects with $IC_{50}$s that were on average almost 10-fold lower than those observed for methotrexate. The cytotoxicity profiles of these two antifolates were similar with the same distinct groups of sensitive and resistant cell lines. The cytotoxicity profile of pralatrexate was different from that of 5-FU, 5'-DFUR, and pemetrexed suggesting differences in the metabolism, mechanism of action and/or resistance between pralatrexate and these other antimetabolites. Interestingly, limited cross-sensitivity was observed between pralatrexate and pemetrexed, a multi-targeted antifolate (MTA) that is believed to be primarily a thymidylate synthetase (TS) inhibitor.

Figure 3:
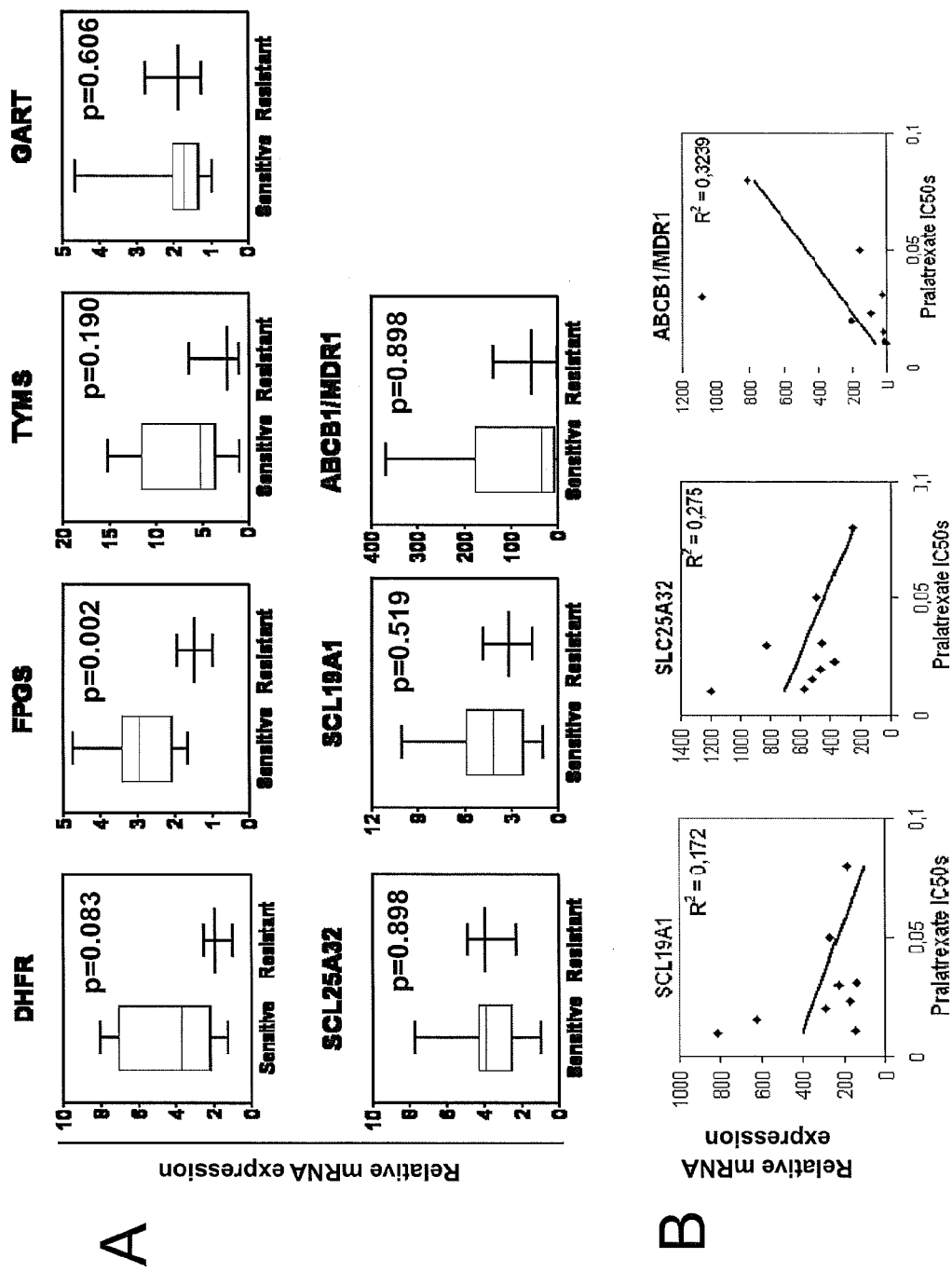
FIGS. 3A and B show relative mRNA expression of folate genes in 10-propargyl-10-deazaaminopterin sensitive and resistant cell lines. A: expression level of DHFR, FPGS, TS, GART, SLC25A32, SCL19A1/RFC1 and ABCB1/MDR1 genes in sensitive and resistant groups. B: correlation between 10-propargyl-10-deazaaminopterin sensitivity and mRNA expression of SCL19A1/RFC1, SLC25A32, and ABCB1/MDR1 transporters in 9 10-propargyl-10-deazaaminopterin sensitive cell lines.

The transcription profiles of genes known to be involved in the resistance to antifolates were analyzed in the panel of cancer cell lines. DHFR (dehydrofolate reductase), FPGS (folyl-polyglutamate synthetase), TS (thymidylate synthetase), SCL19A1 (reduced folate carrier [RFC-1]), GARFT (phosphoribosylglycinamide formyltransferase), SLC25A32 (mitochondrial folate transporter/carrier), and ABC transporter B1 (ABCB1 or MDR1) mRNA expressions were tested by qRT-PCR in the panel of 15 cell lines (FIGS. 3A and B). The group of pralatrexate-sensitive cells expressed relatively higher levels of DHFR, a target of pralatrexate, than the "resistant" group (FIG. 3A). The cell lines sensitive to pralatrexate expressed higher levels of FPGS mRNA than resistant cells (t-test, p=0.002). Overall, a trend toward a correlation between the mRNA expression levels of FPGS and pralatrexate sensitivity ($IC_{50}$s) was found in the panel of cell lines used in this study ($R^2$=0.47, p<0.01), suggesting an important role of polyglutamation in pralatrexate antiproliferative activity.

To determine the potential role of folate transporters in pralatrexate activity, we correlated the $IC_{50}$ values obtained after 72 h drug exposure with the level of mRNA expression of SCL19A1, SLC25A32, and MDR1 genes in the nine-pralatrexate sensitive cell lines (FIG. 3B). Cells that expressed a high level of SCL19A1 and SLC25A32 mRNA displayed higher sensitivity to pralatrexate. Conversely, cells with low MDR1 expression were more sensitive to pralatrexate. These data suggest potential roles of SCL19A1/RFC-1 and SLC25A32 in cellular uptake and MDR1 in efflux of pralatrexate.

Example 4

Western Blot Analysis.

Cells were lysed in buffer containing 50 mM HEPES (pH 7.6), 150 mM NaCl, 1% Triton X-100, 2 mM sodium vanadate, 100 mM NaF, and 0.4 mg/ml phenylmethylsulfonyl fluoride. Equal amounts of protein (20-50 µg/lane) were subjected to SDS-PAGE and transferred to nitrocellulose membranes. Membranes were blocked with 5% milk in 0.01% Tween 20/phosphate-buffered saline and then incubated with the primary antibody overnight. Membranes were then washed and incubated with the secondary antibody conjugated to horseradish peroxidase. Bands were visualized by using the enhanced chemiluminescence Western blotting detection system. Densitometric analysis was performed under conditions that yielded a linear response. The following antibodies were used: anti-cleaved PARP (Cell Signaling, Saint Quentin Yvelines, France), anti-DHFR (Abcam, France), anti-β-actin (Sigma Aldrich, Saint-Quentin Fallavier, France).

To characterize the predictive factors of pralatrexate antiproliferative effects, the cell lines DU-PDX and HEP-PDX were developed from parental DU145 and HEP2 cells, respectively, by exposure to stepwise increasing concentrations of pralatrexate over a period of 6 months. Resulting DU-PDX and HEP-PDX cells were at least 200- and 500-fold less sensitive to pralatrexate than parental cells. After 5 passages in drug-free medium the resistant cells retained their drug resistance, suggesting stability of these cell lines.

To compare the mechanisms of pralatrexate and methotrexate resistance, the cell lines DU-MTX and HEP-MTX were developed from parental DU145 and HEP2 cells by exposure to stepwise increasing concentrations of methotrexate. DU-MTX and HEP-MTX displayed resistance to methotrexate and pralatrexate compared to parental cells. See FIG. 4A. However, the activity of pralatrexate still remained superior (approximately 10-fold lower $IC_{50}$) to that of methotrexate (Data not shown) in DU-MTX and HEP-MTX cancer cells.

Genetic Changes Associated with Acquired Pralatrexate Resistance.

Figure 4:
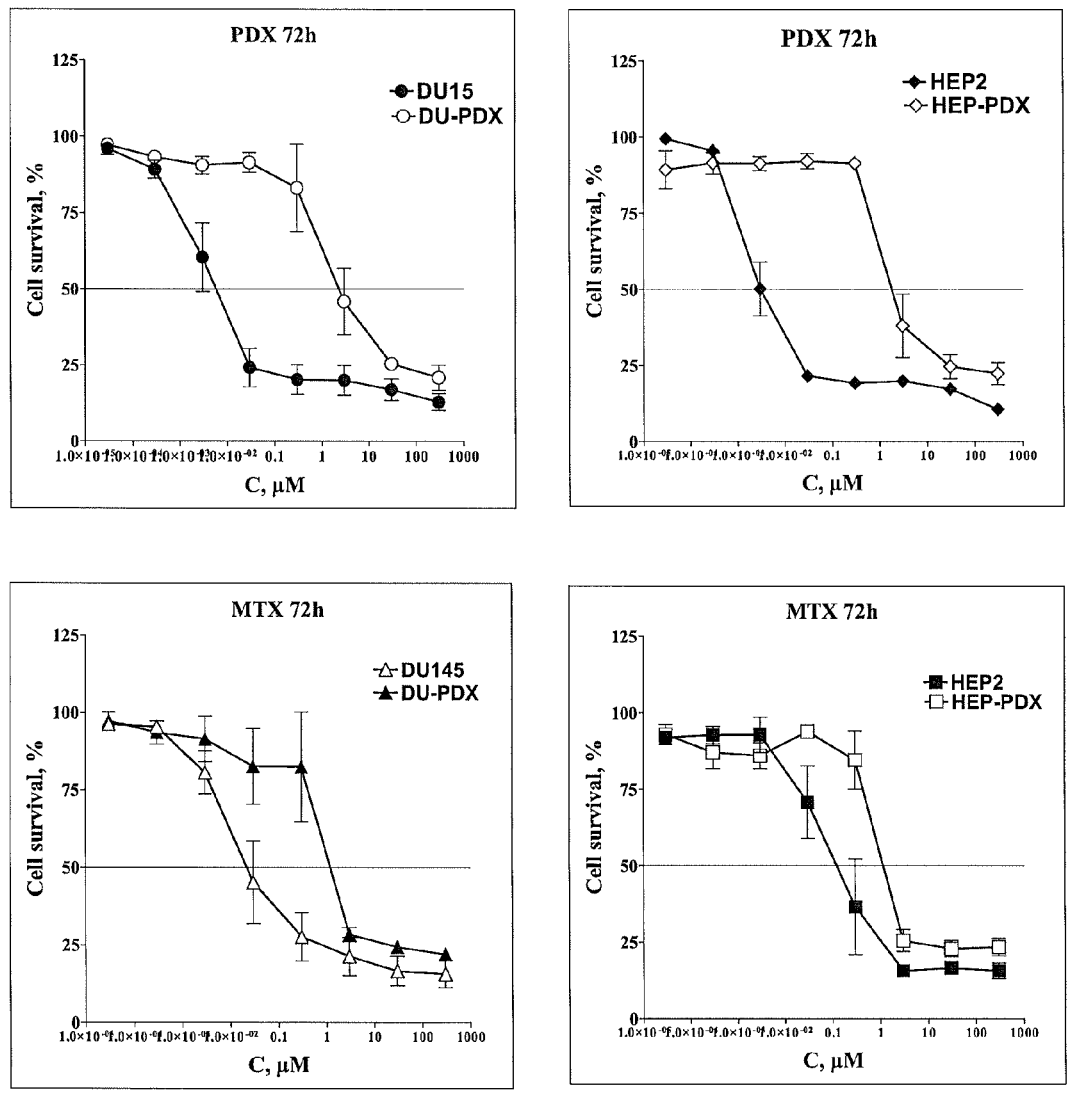
FIG. 4A-C show characterization of 10-propargyl-10-deazaaminopterin-resistant cell lines. A—10-propargyl-10-deazaaminopterin (top panel) and methotrexate (bottom panel) cytotoxicity in DU-PDX and HEP-PDX cell lines comparing to their parental counterparts DU145 and HEP2. B—relative mRNA expression of folate genes in 10-propargyl-10-deazaaminopterin-resistant cell lines. C—Western blot of DHFR protein in DU145 and HEP2 sensitive and DU-PDX, DU-MTX, HEP-PDX and HEP-MTX 10-propargyl-10-deazaaminopterin- and methotrexate-resistant cell lines.
Figure 4:
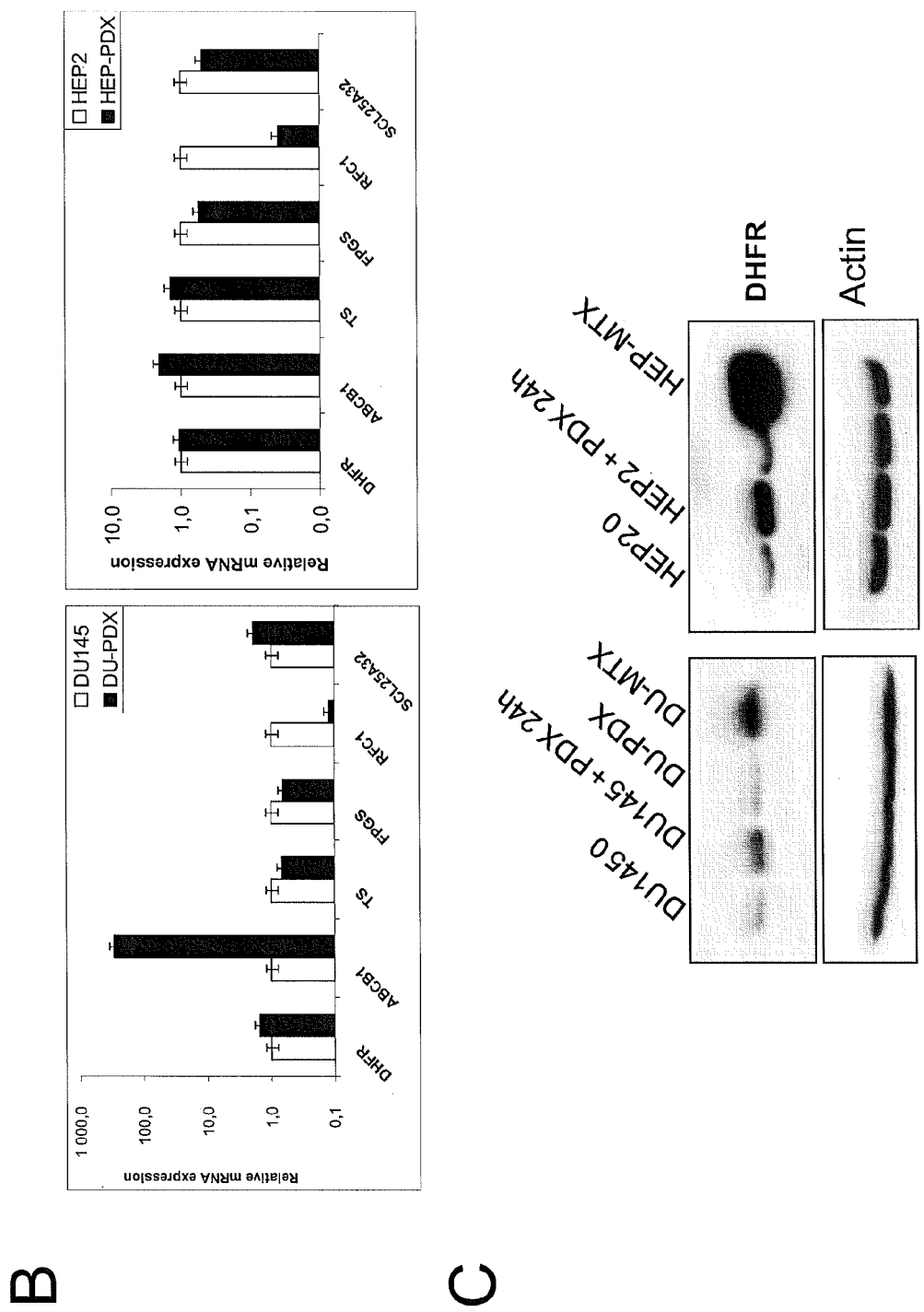

To determine possible mechanisms of anti-folate resistance, we evaluated the mRNA expression of several genes implicated in metabolism of folates including DHFR, TS, FPGS, RFC1/SCL19A1, SLC25A32 and ABCB1/MDR1 in parental and resistant cells. As shown in FIG. 4B, mRNA expression of DHFR, TS, and SLC25A32 was not significantly changed in pralatrexate-resistant cells. A slight decrease in FPGS mRNA expression was observed in DU-PDX and HEP-PDX cells compared with their parental counterparts. In contrast, RFC1/SCL19A1 expression was >10-fold decreased in the two pralatrexate-resistant cell lines. mRNA levels of ABCB1/MDR1 was 40- and 2-fold higher in DU-PDX and HEP-PDX, respectively, compared with DU145 and HEP2. These data suggest an important role of transporters in pralatrexate antiproliferative activity and acquired resistance. Verapamil, a calcium channel blocker, reverses resistance by functioning as a competitive substrate of MDR1, regardless of its innate pharmacological function. Various clinical studies also showed that drugs such as verapamil could reverse resistance to anticancer drugs. To study the role of MDR1 in pralatrexate resistance, DU-PDX and HEP-PDX cells were incubated with 30 µM verapamil and 3 µM cyclosporin A concomitantly with pralatrexate for 72 hours. No changes were observed in pralatrexate cytotoxicity with and without verapamil and cyclosporine A, suggesting no significant role of MDR1 overexpression in acquired resistance in these cell lines.

Analysis of expression of DHFR, a target of pralatrexate and methotrexate, showed significant increases in mRNA (data not shown) and protein in HEP-MTX cells compared with parental HEP2 cells suggesting possible gene amplification FIG. 4C). DHFR protein expression was slightly increased after short (24 hour) exposure to pralatrexate, but not after prolonged (6 months) exposure to pralatrexate, suggesting that the molecular mechanism of acquired resistance to pralatrexate in HEP-PDX cells may differ from methotrexate resistance in HEP-MTX cells.

Analysis of Cross-Resistance to Other Antifolates and Antimetabolites

To evaluate the cross-resistance of pralatrexate-resistant cells to other drugs, DU145, DU-PDX, HEP2 and HEP-PDX cells were exposed to pemetrexed and 5-FU for 72 h at concentrations ranging 30 pM-300 µM and the cytotoxicity was evaluated by MTT after 48 h washout. No significant difference between parental and PDX-resistant cells was observed for 5-FU cytotoxicity. Pemetrexed 72 h exposure was slightly less cytotoxic in DU-PDX and HEP-PDX cells comparing to their parental counterparts (data not shown). These data suggest the mechanism of pralatrexate resistance different from pemetrexed and 5-FU.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed is:

1. A method of selecting a patient for treatment of a cancer with 10-propargyl-10-deazaaminopterin, the method comprising the steps of:
   (a) obtaining a sample of the patient's cancer tissue;
   (b) determining the expression level of a polypeptide comprising a member of a folate pathway polypeptide within a cell comprising least one of reduced folate carrier-1 enzyme (RFC-1), dihydrofolate reductase (DHFR), folylpoly-gamma-glutamate synthetase (FPGS), thymidylate synthase (TS), γ-glutamyl hydrolase (GGH), and glycinamide ribonucleotide formyltransferase (GARFT) in the sample;
   (c) comparing the determined expression level in the sample with a reference expression level for the polypeptide comprising a member of a folate pathway polypeptide within a cell; and
   (d) selecting the patient for treatment 10-propargyl-10-deazaaminopterin where the comparison of the expression level in the sample of the polypeptide comprising a member of a folate pathway polypeptide within a cell and the corresponding reference expression level indicate sensitivity of patient's cancer tissue to 10-propargyl-10-deazaaminopterin.

2. The method of claim 1, wherein the patient's cancer is a solid tumor or a lymphoma.

3. The method of claim 2, wherein the solid tumor is selected from the group consisting of NSCLC, head and neck cancer, prostate cancer, and breast cancer.

4. A method for assessing sensitivity of a patient's cancer to treatment with 10-propargyl-10-deazaaminopterin comprising the steps of:
   (a) obtaining a sample of the patient's cancer tissue;
   (b) determining the expression level of at least one member of a folate pathway polypeptide within a cell comprising least one of reduced folate carrier-1 enzyme (RFC-1), dihydrofolate reductase (DHFR), folylpoly-gamma-glutamate synthetase (FPGS), thymidylate synthase (TS), -glutamyl hydrolase (GGH), and glycinamide ribonucleotide formyltransferase (GARFT) expressed in the sample;
   (c) comparing the determined expression level in the sample with a reference expression level for the polypeptide comprising a member of a folate pathway polypeptide within a cell of a reference cancer to determine whether the expression level for the polypeptide comprising a member of a folate pathway polypeptide within a cell in the sample is indicative of an expression level that predicts sensitivity to 10-propargyl-10-deazaaminopterin; and
   (d) generating a report of the predicted sensitivity of the sample to 10-propargyl-10-deazaaminopterin.

5. The method of claim 4, wherein the reference cancer is a solid tumor or a lymphoma.

6. The method of claim 5, wherein the solid tumor is selected from the group consisting of NSCLC, head and neck cancer, prostate cancer, and breast cancer.

7. A method for assessing sensitivity of a cancer to treatment with 10-propargyl-10-deazaaminopterin comprising the steps of
   (a) obtaining a sample of the lymphoma;
   (b) determining the amount of a member of a folate pathway polypeptide within a cell comprising least one of reduced folate carrier-1 enzyme (RFC-1), dihydrofolate reductase (DHFR), folylpoly-gamma-glutamate synthetase (FPGS), thymidylate synthase (TS), γ-glutamyl hydrolase (GGH), and glycinamide ribonucleotide formyltransferase (GARFT) expressed by the sample wherein higher levels of expressed polypeptide comprising a member of a folate pathway polypeptide within a cell are indicative of sensitivity to 10-propargyl-10-deazaaminopterin; and
   (c) generating a report of the predicted sensitivity of the sample to 10-propargyl-10-deazaaminopterin.

* * * * *

UNITED STATES PATENT AND TRADEMARK OFFICE
CERTIFICATE OF CORRECTION

| | | Page 1 of 1 |
|---|---|---|
| PATENT NO. | : 8,263,354 B2 | |
| APPLICATION NO. | : 12/815321 | |
| DATED | : September 11, 2012 | |
| INVENTOR(S) | : Owen O'Connor et al. | |

It is certified that error appears in the above-identified patent and that said Letters Patent is hereby corrected as shown below:

In The Specification

In column 1, beginning at line 29 please insert:

--This invention was made with government support under grant numbers CA092074 awarded by National Institutes of Health. The government has certain rights in the invention.--

Signed and Sealed this
Twenty-ninth Day of March, 2016

Michelle K. Lee
*Director of the United States Patent and Trademark Office*